United States Patent
Chen et al.

(10) Patent No.: US 10,487,076 B2
(45) Date of Patent: *Nov. 26, 2019

(54) COMPOSITIONS AND METHODS FOR TREATING DISEASES AND CONDITIONS

(71) Applicants: University of Pittsburgh—Of the Commonwealth System of Higher Education, Pittsburgh, PA (US); The United States Government as represented by the Department of Veterans Affairs, Washington, DC (US)

(72) Inventors: Beibei Chen, Wexford, PA (US); Rama K. Mallampalli, Sewickley, PA (US)

(73) Assignees: University of Pittsburgh—Of the Commonwealth System of Higher Education, Pittsburgh, PA (US); The United States Government, as represented by the Department of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/533,978

(22) PCT Filed: Dec. 10, 2015

(86) PCT No.: PCT/US2015/065000
§ 371 (c)(1),
(2) Date: Jun. 7, 2017

(87) PCT Pub. No.: WO2016/094659
PCT Pub. Date: Jun. 16, 2016

(65) Prior Publication Data
US 2018/0134693 A1 May 17, 2018

Related U.S. Application Data

(60) Provisional application No. 62/090,309, filed on Dec. 10, 2014.

(51) Int. Cl.
*A61K 31/505* (2006.01)
*C07D 239/26* (2006.01)
(Continued)

(52) U.S. Cl.
CPC .......... *C07D 413/12* (2013.01); *A61K 31/495* (2013.01); *A61K 31/496* (2013.01);
(Continued)

(58) Field of Classification Search
None
See application file for complete search history.

(56) References Cited

U.S. PATENT DOCUMENTS 4,010,282 A 3/1977 Binning et al.
9,359,284 B2 6/2016 Chen et al.
(Continued)

FOREIGN PATENT DOCUMENTS

EP 1 127 883 8/2001
EP 1 159 261 12/2001
(Continued)

OTHER PUBLICATIONS

Azadbakht et al., "Synthesis and Characterization of Bis-quinazolines from Linear Tetra-amines Involving 2-(Aminomethyl)benzenamine with Aldehydes," *J. Heterocyclic Chem.*, vol. 50, pp. 979-981, Jul. 2, 2013.
Chen et al., U.S. Appl. No. 15/816,963, filed Nov. 17, 2017.
Extended European Search Report issued by European Patent Office for EPC Application No. 15867872.2 dated Jun. 26, 2018.
Hall et al., "Factors influencing mononuclear *versus* multinuclear coordination in a series of potentially hexadentate acyclic $N_6$ ligands: the roles of flexibility and chelate ring size," *Dalton Transactions*, vol. 40, pp. 12075-12082, 2011.
Non-Final Office Action issued for U.S. Appl. No. 15/138,120 dated Dec. 21, 2017.
(Continued)

*Primary Examiner* — Samantha L Shterengarts
(74) *Attorney, Agent, or Firm* — Klarquist Sparkman, LLP

(57) ABSTRACT

A compound of Formula II, or a salt, ester, solvate, hydrate or prodrug thereof:

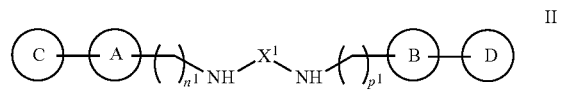

where:
$X^1$ is a branched or unbranched $C_{1-10}$ alkyl, $(CH_2)_s$—NH—$(CH_2)_t$, $(CH_2)_s$—O—$(CH_2)_t$, or $(CH_2)_s$—C(NH$_2$)—$(CH_2)_v$—NH—$(CH_2)_t$, where s, t and v are each, independently an integer from 1 to 5;

A and B are each, independently, $C_{6-10}$aryl, $C_{6-10}$aryl-$C_{1-6}$alkyl, $C_{3-9}$ heteroaryl, or $C_{3-9}$heteroaryl-$C_{1-6}$alkyl, each optionally substituted with 1, 2 or 3 independently selected $R^g$ groups;

C and D are each, independently, $C_{3-7}$ cycloalkyl, $C_{3-7}$ cycloalkyl-$C_{1-6}$alkyl, $C_{3-7}$ heterocycloalkyl, $C_{3-7}$ heterocycloalkyl-$C_{1-6}$ alkyl, $C_{6-10}$aryl, $C_{6-10}$aryl-$C_{1-6}$alkyl, $C_{3-9}$ heteroaryl, or $C_{3-9}$heteroaryl-$C_{1-6}$alkyl, each optionally substituted with 1, 2 or 3 independently selected $R^g$ groups;

each $R^g$ is, independently, halogen, $C_{1-6}$ alkyl, $C_{1-6}$ haloalkyl, hydroxyl, $C_{1-6}$ alkoxy, $C_{1-6}$ haloalkoxy, amino, $C_{1-6}$ alkylamino, or di-$C_{1-6}$alkylamino; and $n^1$ and $p^1$ are each, independently, integers from 1 to 10.

14 Claims, 14 Drawing Sheets

(51) Int. Cl.
| | |
|---|---|
| C07D 413/12 | (2006.01) |
| A61K 31/495 | (2006.01) |
| A61K 31/496 | (2006.01) |
| A61K 31/497 | (2006.01) |
| C07C 211/27 | (2006.01) |
| C07C 211/49 | (2006.01) |
| C07C 211/54 | (2006.01) |
| C07C 217/08 | (2006.01) |
| C07C 217/58 | (2006.01) |
| C07D 413/14 | (2006.01) |
| C07D 241/12 | (2006.01) |
| A61P 17/06 | (2006.01) |
| A61P 9/10 | (2006.01) |
| A61P 31/00 | (2006.01) |
| A61P 11/06 | (2006.01) |
| A61P 17/00 | (2006.01) |
| A61P 19/02 | (2006.01) |
| A61P 37/08 | (2006.01) |
| A61P 3/10 | (2006.01) |
| A61P 13/02 | (2006.01) |
| A61P 1/00 | (2006.01) |
| A61P 11/00 | (2006.01) |
| A61P 27/00 | (2006.01) |

(52) U.S. Cl.
CPC .......... *A61K 31/497* (2013.01); *A61K 31/505* (2013.01); *A61P 1/00* (2018.01); *A61P 3/10* (2018.01); *A61P 9/10* (2018.01); *A61P 11/00* (2018.01); *A61P 11/06* (2018.01); *A61P 13/02* (2018.01); *A61P 17/00* (2018.01); *A61P 17/06* (2018.01); *A61P 19/02* (2018.01); *A61P 27/00* (2018.01); *A61P 31/00* (2018.01); *A61P 37/08* (2018.01); *C07C 211/27* (2013.01); *C07C 211/49* (2013.01); *C07C 211/54* (2013.01); *C07C 217/08* (2013.01); *C07C 217/58* (2013.01); *C07D 239/26* (2013.01); *C07D 241/12* (2013.01); *C07D 413/14* (2013.01); *C07C 2601/14* (2017.05)

(56) References Cited

U.S. PATENT DOCUMENTS

| | | |
|---|---|---|
| 9,849,098 B2 | 12/2017 | Chen et al. |
| 2003/0013772 A1 | 1/2003 | Murphy et al. |
| 2006/0148904 A1 | 7/2006 | Protopopova et al. |
| 2015/0152041 A1 | 6/2015 | Chen et al. |
| 2016/0235747 A1 | 8/2016 | Chen et al. |
| 2016/0237040 A1 | 8/2016 | Chen et al. |
| 2016/0310447 A1 | 10/2016 | Chen et al. |
| 2018/0071232 A1 | 3/2018 | Chen et al. |

FOREIGN PATENT DOCUMENTS

| | | |
|---|---|---|
| JP | 2001-278869 | 10/2001 |
| WO | WO 1999/024395 | 5/1999 |
| WO | WO 2001/072685 | 10/2001 |
| WO | WO 03/096989 | 11/2003 |
| WO | WO 2008/027932 | 3/2008 |
| WO | WO 2008/142623 | 11/2008 |
| WO | WO 2013/184202 | 12/2013 |
| WO | WO 2015/089087 | 6/2015 |

OTHER PUBLICATIONS

Non-Final Office Action issued for U.S. Appl. No. 15/138,137 dated Dec. 14, 2017.
Tolpygin et al., "Chemosensor Activity of 2-(Anthracen-9-yl)-Substituted Imidazolines and Hexahydropyrimidines," *Russian Journal of Organic Chemistry*, 48(1): 104-408, 2012.
Albano, et al., "Novel chiral diamino-oligothiophenes as valuable ligands in Pd-catalyzed allylic alkylations. On the primary role of secondary interactions in asymmetric catalysis," *Advanced Synthesis & Catalysis*, vol. 347, 1507-1512, Oct. 19, 2005.
Caterina et al. "Imidazolidines are new anti-Trypanosoma cruzi agents: Biological evaluation and structure-activity relationships", *Bioorganic & Medicinal Chemistry*, 16: 2226-2234, 2008.
Chen et al., "A combinatorial F box protein directed pathway controls TRAF adaptor stability to regulate inflammation," *Nature Immunology*, 14(5): 470-479, May 2013.
Chen et al., "Calmodulin Antagonizes a Calcium-Activated SCF Ubiquitin E3 Ligase Subunit, FBXL2, To Regulate Surfactant Homeostasis," *Molecular and Cellular Biology*, 31(9): 1905-1920, May 1, 2011.
Cisneros et al., "Efficacy of moxifloxacin monotherapy versus gatifloxacin monotherapy, piperacillin-tazobactam combination therapy, and clindamycin plus gentamicin combination therapy: an experimental study in a rat model of intra-abdominal sepsis induced by fluoroquinolone-resistant *Bacteroides fragilis*," *Current Therapeutic Research*, 48(6): 1021-1029, 1990.
Examination Report issued for EPC application No. 13800256.3 issued by the European Patent Office dated Aug. 29, 2016.
Gakhar et al., "Anti-tumor effect of primaquine compounds in human breast cancer cells," *Proceedings of the American Association for Cancer Research Annual Meeting—98th Annual Meeting of the American Association for Cancer Research*, 67(9), May 2007.
Grabenko et al., "Synthesis and study of p-substituted toluoyl derivatives of ethylenediamine and piperzine," *Ukrainskii Khimicheskii Zhurnal*, 47(9): 956-959, 1981 (English translation).
Hagers Handbuch der Pharmazeutischen Praxis, vol. 2, p. 828, 1998.
Huang et al., "Syntheses, crystal structures and properties of silver (I) and copper (II) complexes with an oxazoline-containing tetradentate ligand," *New Journal of Chemistry*, No. 34, pp. 2436-2444, Jun. 3, 2010.
International Search Report and Written Opinion from International application No. PCT/US2013/030995, dated Jun. 13, 2013.
International Search Report and Written Opinion from International application No. PCT/US2014/069368, dated Mar. 17, 2015.
International Search Report and Written Opinion issued for International Application No. PCT/US2015/065000 dated Apr. 11, 2016.
Kauffmann, et al., "A heterocyclohexaaromatic compound with 'face-to-face' arrangement of two benzene rings," *Angewandte Chemie*, 90(10): 804-805, 1978. (English abstract only).
Khan et al., "Synthesis, anti-inflammatory and analgesic activity of new hexahydro-pyrimidine derivatives", *Pharmazie*, 57:377-383, 2002.
Kraml et al., "Agents Affecting Lipid Metabolism. VIII. N,N-Dibenzylethylenediamine, the Key to a Novel Class of Cholesterol Biosynthesis Inhibitors," *J. Med. Chem.*, vol. 7, pp. 500-503, 1964.
Lakatos et al., "Two pyridine derivatives as potential Cu(II) and Zn(II) chelators in therapy for Alzheimer's disease," *The International Journal for Inorganic, Organometallic and Bioinorganic Chemistry*, vol. 39, 1302-1315, Jan. 1, 2010.
Lexy et al, "Heterocyclopolyaromatics. X. The first cyclohexaaromatic compound with 'face-to-face' arrangement of two aromatic ring members," *Chemiste Berichte*, 113(8): 2749-2754, 1980. (English abstract only).
Mallampalli, et al., "Targeting F box protein Fbxo3 to control cytokine-driven inflammation," *The Journal of Immunology*, 191(10): 5247-5255, Oct. 11, 2013.
Official Action issued by Japan Patent Office dated Sep. 29, 2016, for Japanese Application No. 2015-516008 (English translation).
PubChem, SID 103190923, Dec. 22, 2010, http://pubchem.ncbi.nlm.nih.gov/substance/103190923.
PubChem, SID 103191203, Dec. 22, 2010, https://pubchem.ncbi.nlm.nih.gov/substance/1031911203.
Sharma et al., "Synthesis, antimicrobial activity and structure-activity relationship study of N, N-dibenzyl-cyclohexane-1,2-diamine derivatives", *European Journal of Medicinal Chemistry*, 46:480-487, 2011.
STN Registry No. 1209629-41-3, entered Mar. 14, 2010.

(56) References Cited

OTHER PUBLICATIONS

Sundaravel et al., "Synthesis, structure, spectra and reactivity of iron(III) complexes of facially coordinating and sterically hindering 3N ligands as models for catechol dioxygenases," *Dalton Transactions*, pp. 7012-7025, Nov. 3, 2008.
U.S. Appl. No. 15/138,120, filed Apr. 25, 2016.
U.S. Appl. No. 15/138,137, filed Apr. 25, 2016.
Valcke et al., "Penetration of Ampicillin and Sulbactam in the Lower Airways during Respiratory Infections," *Antimicrobial Agents and Chemotherapy*, pp. 958-962, Jun. 1990.
Yigit, "The Synthesis of Some Perhydrobenzimidazolimium Salts and Their Application Pd-Carbene Catalyzed Heck and Suzuki Reactions," *Molecules*, vol. 14, pp. 2032-2042, Jun. 5, 2009.

FIG. 1A
| | Structure |
|---|---|
| BC-1301 | 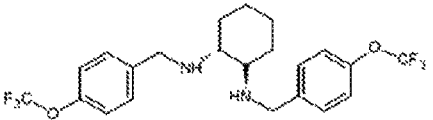 |
| BC-1303 | 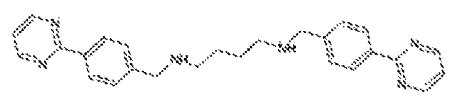 |
| BC-1304 | 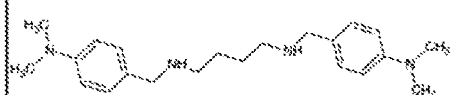 |
| BC-1305 | 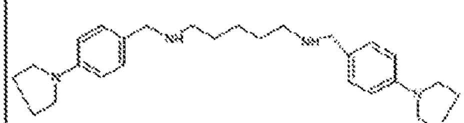 |

FIG. 2A
BC-1421
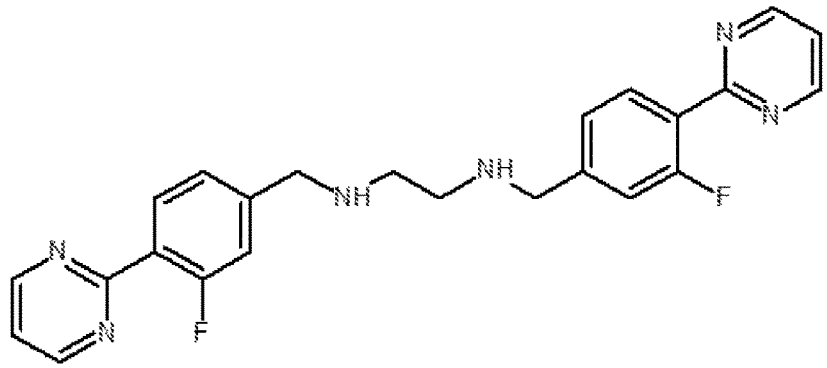
BC-1422
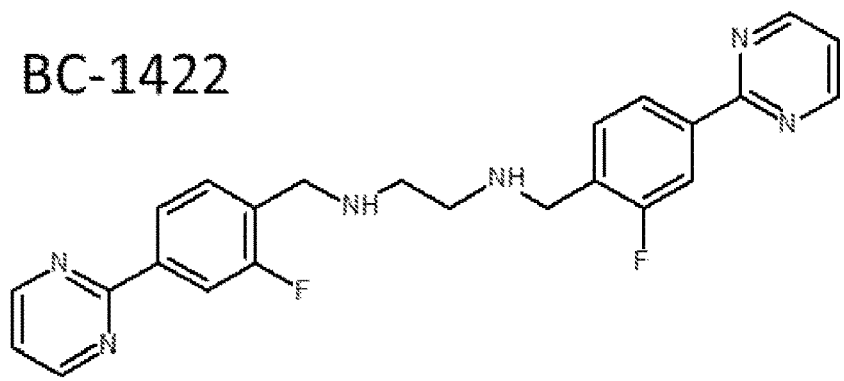
BC-1423
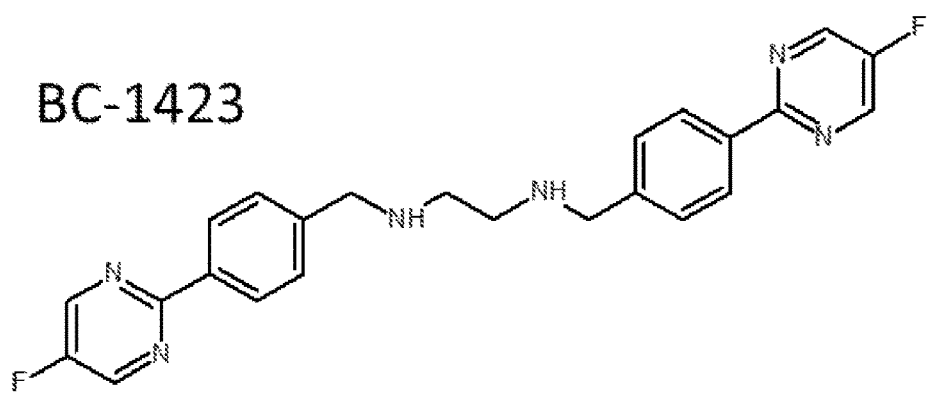

COMPOSITIONS AND METHODS FOR TREATING DISEASES AND CONDITIONS

This is the U.S. National Stage of International Application No. PCT/US2015/065000, filed Dec 10, 2015, which was published in English under PCT Article 21(2), which in turn claims the benefit of U.S. Provisional Application No. 62/090,309, filed Dec 10, 2014 The provisional application is incorporated herein in its entirety.

ACKNOWLEDGMENT OF GOVERNMENT SUPPORT

This invention was made with government support under HL116472, UH2HL123502, HL081784, HL068135, HL096376, HL098174, and HL097376 awarded by the National Institutes of Health. The government has certain rights in the invention.

BACKGROUND

Secretion of pro-inflammatory cytokines after infection with virulent pathogens, in response to host cell injury, or related irritants that activate receptors on immune effector cells (T-cells, macrophages, etc.) underlies numerous diseases including various respiratory diseases. For example, acute and chronic bronchitis, emphysema, respiratory infections (pneumonia, pleurisy), flu (including influenza), post-lung transplant rejection including acute and chronic rejection and bronchiolitis obliterans, acute lung injury or the acute respiratory distress syndrome, pulmonary fibrosis, asthma, cystic fibrosis, and bronchiectasis are all linked to activation of injurious cytokines. Efforts to block cytokine release and circulation have focused on administration of systemic corticosteroids or targeted anti-inflammatory agents to specific cytokines such as TNFα and IL-1p.

TNF receptor associated factors (TRAFs) are a family of proteins primarily involved in the regulation of inflammation, antiviral responses, and apoptosis. Six well-characterized TRAF proteins (TRAF1-6) exist and a newer homologue TRAF7 was recently identified. All TRAF members share a highly conserved C-terminal domain that mediates interactions with transmembrane TNF receptors. Identification of TRAF proteins has contributed significantly to the elucidation of the molecular mechanisms of signal transduction emanating from the TNFR superfamily and the Toll like/interleukin-1 receptor (TLR/IL-1R) family TRAF family proteins interact with the IL-1 receptor, TLRs, CD40, RANK, I-TAC, p'75 NGF receptor, etc. Specifically, TRAF2, TRAF5, and TRAF6 serve as adapter proteins that link cell surface receptors with downstream kinase cascades, which in turn activate key transcription factors, such as nuclear factor kB (NFkB), resulting in cytokine gene expression. With an exaggerated immune response, TRAF-mediated cytokine release leads to profound effects of edema, multi-organ failure and shock. The TRAF proteins, however, have a central role as they mediate signal transduction to elicit transcriptional activation of several downstream cytokines. These findings suggest that maneuvers designed to selectively modulate the abundance of TRAF proteins might serve as a novel strategy for therapeutic intervention. However, to date, very little is known regarding the molecular regulation of the TRAF family at the level of protein stability. Strategies directed at modulation of TRAF protein concentrations in cells might serve as the basis for the design of a new class of anti-inflammatory agents.

Ubiquitination of proteins brands them for degradation, either by the proteasome or via the lysosome, and regulates diverse processes. The conjugation of ubiquitin to a target protein is orchestrated by a series of enzymatic reactions involving an E1 ubiquitin-activating enzyme, ubiquitin transfer from an El-activating enzyme to an E2-conjugating enzyme, and last, generation of an isopeptide bond between the substrate's e-amino lysine and the c-terminus of ubiquitin catalyzed by a E3-ubiquitin ligase. Of the many E3 ligases, the Skp-Cullin1-F box (SCF) superfamily is among the most studied. The SCF complex has a catalytic core complex consisting of Skp1, Cullin1, and the E2 ubiquitin-conjugating (Ubc) enzyme. The SCF complex also contains an adaptor receptor subunit, termed F-box protein, that targets hundreds of substrates through phosphospecific domain interactions. F-box proteins have two domains: an NH2-terminal F-box motif and a C-terminal leucine-rich repeat (LRR) motif or WD repeat motif. The SCF complex uses the F-box motif to bind Skpl, whereas the leucine-rich/WD repeat motif is used for substrate recognition.

Ubiquitin E3 ligase subunit, FBXO3, has been found to be sufficient to ubiquitinate and mediate proteasomal degradation of another relatively recently-identified ubiquitin E3 ligase subunit, FBXL2. Further, FBXL2 appears to act as a "break" on inflammation, by targeting the TRAF family of proteins for their disposal in epithelia and monocytes. Thus, activation of FBXO3 results in FBXL2 ubiquitination and degradation increasing immunoreactive TRAFs and cytokine production, and impairing lung function. Bronchitis and other respiratory diseases and respiratory injury cause increased FBXO3 activity. Therefore, small molecule inhibitors of FBXO3 function may be useful in the prophylaxis and treatment of these respiratory diseases and injuries.

SUMMARY

Various embodiments of the invention are directed to compounds of general Formula I:

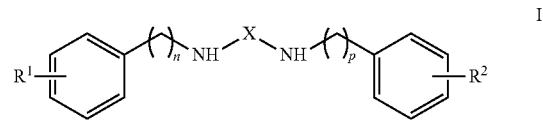

or salts, esters, solvates, hydrates, or prodrugs thereof; wherein X is $C_{1-10}$ alkyl, $(CH_2)_s$—NH—$(CH_2)_t$, $(CH_2)_s$—O—$(CH_2)_t$, or $(CH_2)_s$—C(NH_2)—$(CH_2)_v$—NH—$(CH_2)_t$, wherein s, t and v are each, independently, an integer from 1 to 5; $R^1$ and $R^2$ are each, independently, amine, $C_{1-10}$ alkyl, $C_{1-10}$ alkenyl, $C_{1-10}$ alkynyl, $C_{3-7}$ cycloalkyl, $C_{3-7}$ cycloalkyl-$C_{1-6}$ alkyl, $C_{3-7}$ heterocycloalkyl, or $C_{3-7}$ heterocycloalkyl-$C_{1-6}$ alkyl; and n and p are each, independently, integers from 1 to 10.

In some embodiments, $R^1$ and $R^2$ can be the same, and in certain embodiments, $R^1$ and $R^2$ can be in para configuration. In particular embodiments, $R^1$ and $R^2$ can each, independently, be selected from 6-membered cycloalkyl, 6-membered heterocycloalkyl, 5-membered cycloalkyl, 5-membered heterocycloalkyl, and the like, and in various embodiments, $R^1$ and $R^2$ can each, independently, be substituted with at least one Rg group selected from halogen, $C_{1-6}$ alkyl, $C_{1-6}$ haloalkyl, hydroxyl, $C_{1-6}$ alkoxy, $C_{1-6}$ haloalkoxy, amino, $C_{1-6}$alkylamino, or di-$C_{1-6}$alkylamino. In some embodiments, $R^1$ and $R^2$ can each, independently, include a linker heteroatom. For example, $R^1$ and $R^2$ can each, independently, be selected from:

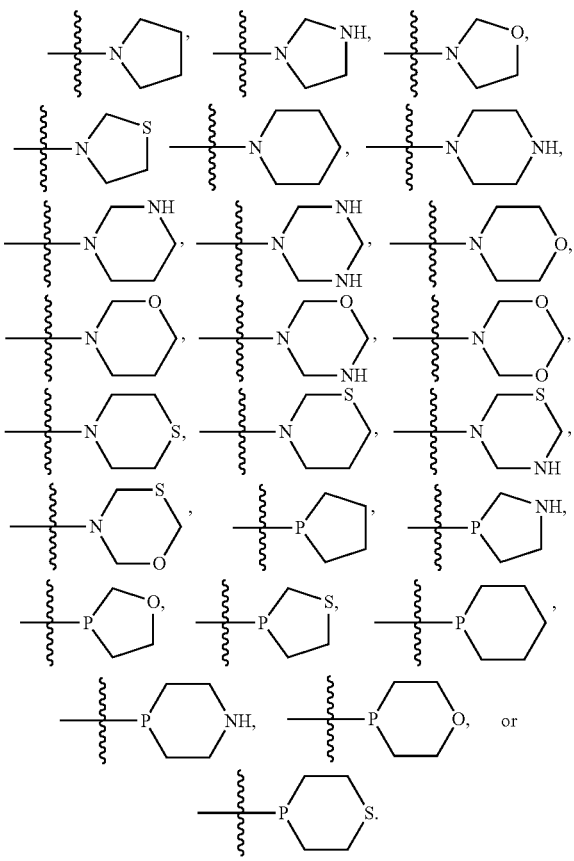

In certain embodiments, each $R^1$ and $R^2$ can, independently, be selected from pyrrolidine and piperidine.

In some embodiments, each $R^1$ and $R^2$ can, independently, be a tertiary amine For example, each $R^1$ and $R^2$ may, independently, be of formula $-NR^3R^4$ where each $R^3$ and $R^4$ is, independently, selected from $C_{1-10}$ alkyl, $C_{1-10}$ alkenyl, or $C_{1-10}$ alkynyl. In some embodiments, $R^3$ and $R^4$ can each, independently, be substituted with at least one substituent selected from halogen, $C_{1-6}$ alkyl, $C_{1-6}$ haloalkyl, hydroxyl, $C_{1-6}$ alkoxy, $C_{1-6}$ haloalkoxy, amino, $C_{1-6}$alkylamino, or di-$C_{1-6}$alkylamino In further embodiments, each $R^1$ and $R^2$ can, independently, be a secondary amine, and in some embodiments, the secondary amine may include a branched $C_{1-10}$ alkyl, $C_{1-10}$ alkenyl, or $C_{1-10}$ alkynyl. In certain embodiments, the branched $C_{1-10}$ alkyl, $C_{1-10}$ alkenyl, or $C_{1-10}$ alkynyl is substituted with at least one substituent selected from the group consisting of halogen, $C_{1-6}$ alkyl, $C_{1-6}$ haloalkyl, hydroxyl, $C_{1-6}$ alkoxy, $C_{1-6}$ haloalkoxy, amino, $C_{1-6}$alkylamino, and di-$C_{1-6}$alkylamino In various embodiments, described above X may be selected from $CH_2)_s$—NH—$(CH_2)_t$— or —$(CH_2)_s$—O—$(CH_2)_t$—, wherein s and t are each, independently an integer from 1 to 3, and in certain embodiments, X may be —$CH_2$—NH—$CH_2$— or —$CH_2$—O—$CH_2$—. In some embodiments, X may be a branched $C_{1-10}$ alkyl. For example, X may be selected from —$CH(CH_3)CH_2$—, —$CH(CH_3)CH(CH_3)$—, —$CH_2C(CH_3)(CH_3)CH_2$—, —$C(CH_3)(CH_3)$—, —$CH_2C(CH_3)(CH_3)$—, or —$(CH_2)_2C(NH_2)CH_2NHCH_2$—.

In some embodiments, the compounds of the invention may be of Formula Ia:

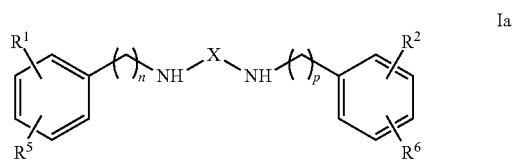

or salts, esters, solvates, hydrates, or prodrugs thereof; wherein X is $C_{1-10}$ alkyl, $(CH_2)_s$—NH—$(CH_2)_t$, $(CH_2)_s$—O—$(CH_2)_t$, or $(CH_2)_s$—C(NH_2)—$(CH_2)_v$—NH—$(CH_2)_t$, wherein s, t and v are each, independently, an integer from 1 to 5; $R^1$ and $R^2$ are each, independently, amine, $C_{1-10}$ alkyl, $C_{1-10}$ alkenyl, $C_{1-10}$ alkynyl, $C_{3-7}$ cycloalkyl, $C_{3-7}$ cycloalkyl-$C_{1-6}$alkyl, $C_{3-7}$ heterocycloalkyl, or $C_{3-7}$ heterocycloalkyl-$C_{1-6}$ alkyl; and n and p are each, independently, integers from 1 to 10; and $R^5$ and $R^6$ are each, independently, selected from the group consisting of halogen, $C_{1-6}$ alkyl, $C_{1-6}$ haloalkyl, hydroxyl, $C_{1-6}$ alkoxy, $C_{1-6}$ haloalkoxy, amino, $C_{1-6}$alkylamino, and di-$C_{1-6}$alkylamino Any of the various descriptions for $R^1$, $R^2$, and X above may be applied to the compounds of Formula Ia.

Certain embodiments are directed to pharmaceutical compositions including compounds of general Formula I:

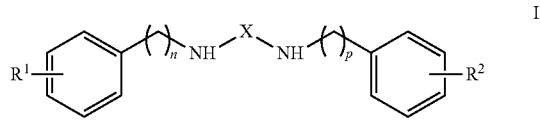

or salts, esters, solvates, hydrates, or prodrugs thereof; wherein X is $C_{1-10}$ alkyl, $(CH_2)_s$—NH—$(CH_2)_t$, $(CH_2)_s$—O—$(CH_2)_t$, or $(CH_2)_s$—C(NH_2)—$(CH_2)_v$—NH—$(CH_2)_t$, where s, t and v are each, independently, an integer from 1 to 5; $R^1$ and $R^2$ are each, independently, amine, $C_{1-10}$ alkyl, $C_{1-10}$ alkenyl, $C_{1-10}$ alkynyl, $C_{3-7}$ cycloalkyl, $C_{3-7}$ cycloalkyl-$C_{1-6}$alkyl, $C_{3-7}$ heterocycloalkyl, or $C_{3-7}$ heterocycloalkyl-$C_{1-6}$ alkyl; and n and p are each, independently, integers from 1 to 10; and a pharmaceutically acceptable carrier, excipient, or diluent.

In some embodiments, $R^1$ and $R^2$ can be the same, and in certain embodiments, $R^1$ and $R^2$ can be in para configuration. In particular embodiments, $R^1$ and $R^2$ can each, independently, be selected from 6-membered cycloalkyl, 6-membered heterocycloalkyl, 5-membered cycloalkyl, 5-membered heterocycloalkyl, or the like, and in various embodiments, $R^1$ and $R^2$ can each, independently, be substituted with at least one $R^g$ group selected from halogen, $C_{1-6}$ alkyl, $C_{1-6}$ haloalkyl, hydroxyl, $C_{1-6}$ alkoxy, $C_{1-6}$ haloalkoxy, amino, $C_{1-6}$alkylamino, or di-$C_{1-6}$alkylamino.

In some embodiments, $R^1$ and $R^2$ can each, independently, include a linker heteroatom. For example, $R^1$ and $R^2$ can each, independently, be selected from:

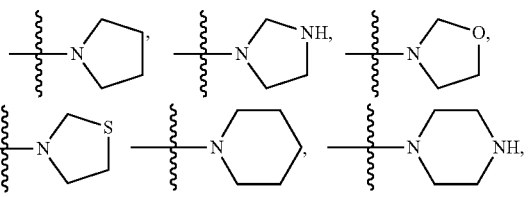

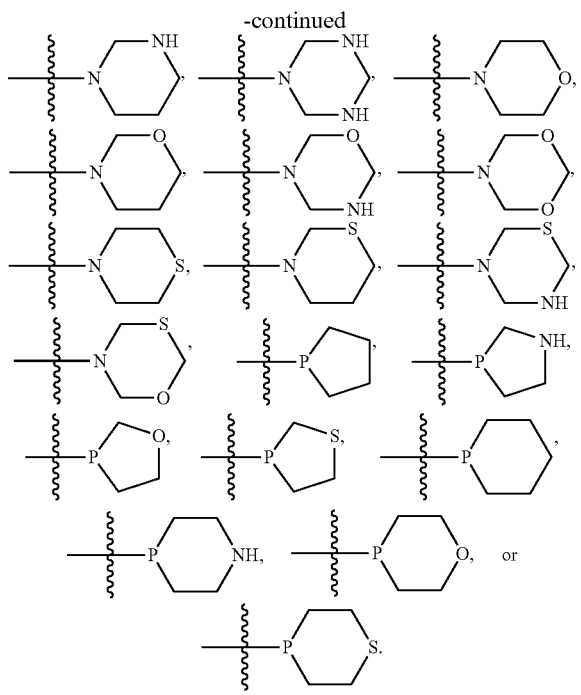

In certain embodiments, each $R^1$ and $R^2$ can, independently, be selected from pyrrolidine and piperidine.

In some embodiments, each $R^1$ and $R^2$ can, independently, be a tertiary amine For example, each $R^1$ and $R^2$ may, independently, be of formula —$NR^3R^4$ where each $R^3$ and $R^4$ is, independently, selected from $C_{1-10}$ alkyl, $C_{1-10}$ alkenyl, or $C_{1-10}$ alkynyl. In some embodiments, $R^3$ and $R^4$ can each, independently, be substituted with at least one substituent selected from halogen, $C_{1-6}$ alkyl, $C_{1-6}$ haloalkyl, hydroxyl, $C_{1-6}$ alkoxy, $C_{1-6}$ haloalkoxy, amino, $C_{1-6}$alkylamino, or di-$C_{1-6}$alkylamino In further embodiments, each $R^1$ and $R^2$ can, independently, be a secondary amine, and in some embodiments, the secondary amine may include a branched $C_{1-10}$ alkyl, $C_{1-10}$ alkenyl, or $C_{1-10}$ alkynyl. In certain embodiments, the branched $C_{1-10}$ alkyl, $C_{1-10}$ alkenyl, and $C_{1-10}$ alkynyl is substituted with at least one substituent selected from the group consisting of halogen, $C_{1-6}$ alkyl, $C_{1-6}$ haloalkyl, hydroxyl, $C_{1-6}$ alkoxy, $C_{1-6}$ haloalkoxy, amino, $C_{1-6}$ alkylamino, and di-$C_{1-6}$alkylamino In various embodiments, described above X may be selected from $CH_2)_s$—NH—$(CH_2)_t$— or —$(CH_2)_s$—O—$(CH_2)_t$—, wherein s and t are each, independently an integer from 1 to 3, and in certain embodiments, X may be —$CH_2$—NH—$CH_2$— or —$CH_2$—O—$CH_2$—. In some embodiments, X may be a branched $C_{1-10}$ alkyl. For example, X may be selected from —$CH(CH_3)CH_2$—, —$CH(CH_3)CH(CH_3)$—, —$CH_2C(CH_3)(CH_3)CH_2$—, —$C(CH_3)(CH_3)$—, or —$CH_2C(CH_3)(CH_3)$—.

In some embodiments, the compounds of the invention may be of Formula Ia:

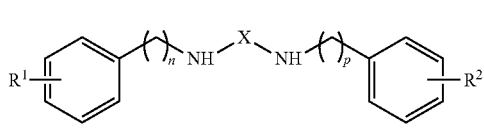

or salts, esters, solvates, hydrates, or prodrugs thereof; wherein X is $C_{1-10}$ alkyl, $(CH_2)_s$—NH—$(CH_2)_t$, $(CH_2)_s$—O—$(CH_2)_t$, or $(CH_2)_s$—C(NH_2)—(CH_2)_v—NH—(CH_2)_t$, wherein s, t and v are each, independently, an integer from 1 to 5; $R^1$ and $R^2$ are each, independently, amine, $C_{1-10}$ alkyl, $C_{1-10}$ alkenyl, $C_{1-10}$ alkynyl, $C_{3-7}$ cycloalkyl, $C_{3-7}$ cycloalkyl-$C_{1-6}$alkyl, $C_{3-7}$ heterocycloalkyl, or $C_{3-7}$ heterocycloalkyl-$C_{1-6}$ alkyl; and n and p are each, independently, integers from 1 to 10; and $R^5$ and $R^6$ are each, independently, selected from the group consisting of halogen, $C_{1-6}$ alkyl, $C_{1-6}$haloalkyl, hydroxyl, $C_{1-6}$ alkoxy, $C_{1-6}$ haloalkoxy, amino, $C_{1-6}$alkylamino, and di-$C_{1-6}$alkylamino Any of the various descriptions for $R^1$, $R^2$, and X above may be applied to the compounds of Formula Ia.

In some embodiments, the carrier may be selected from water, ethanol, polyol, glycerol, propylene glycol, liquid polyethylene glycol, vegetable oils, nut oils, and mixtures thereof. In particular embodiments, the pharmaceutical compositions may further include at least one flavoring agent, binding agent, lubricant, disintegrant, surface modifying agent, surfactant, suspending agent, stabilizing agent, fillers, glidant, compression aid, disintegrating agent, encapsulating material, and the like or combinations thereof. In further embodiments, the pharmaceutical compositions may also include at least one anti-inflammatory agents, antimicrobial agents, matrix metalloprotease inhibitors, lipoxygenase inhibitors, cytokine antagonists, immunosuppressants, anti-cancer agents, anti-viral agents, cytokines, growth factors, immunomodulators, prostaglandins, anti-vascular hyperproliferation compounds, and the like and combinations thereof. In certain embodiments, the compound of Formula I or salt, ester, solvate, hydrate, or prodrug thereof may be about 15 wt. % to about 95 wt. % of a total weight of the pharmaceutical composition. In some embodiments, the pharmaceutical compositions may be in unit dose form, and in particular embodiments, each unit dose may include about 0.5 mg to about 500 mg of the compound of Formula I or salt, ester, solvate, hydrate, or prodrug thereof.

Further embodiments are directed to methods for treating a disease or condition including the steps of administering to a patient in need of treatment a pharmaceutical composition comprising a compound of general Formula I:

I or salts, esters, solvates, hydrates, or prodrugs thereof; wherein X is $C_{1-10}$ alkyl, $(CH_2)_s$—NH—$(CH_2)_t$, or $(CH_2)_s$—O—$(CH_2)_t$, where s and t are each, independently, an integer from 1 to 5; $R^1$ and $R^2$ are each, independently, amine, $C_{1-10}$ alkyl, $C_{1-10}$ alkenyl, $C_{1-10}$ alkynyl, $C_{3-7}$ cycloalkyl, $C_{3-7}$ cycloalkyl-$C_{1-6}$alkyl, $C_{3-7}$ heterocycloalkyl, or $C_{3-7}$ heterocycloalkyl-$C_{1-6}$ alkyl; and n and p are each, independently, integers from 1 to 10; and a pharmaceutically acceptable carrier, excipient, or diluent.

In some embodiments, $R^1$ and $R^2$ can be the same, and in certain embodiments, $R^1$ and $R^2$ can be in para configuration. In particular embodiments, $R^1$ and $R^2$ can each, independently, be selected from 6-membered cycloalkyl, 6-membered heterocycloalkyl, 5-membered cycloalkyl, or 5-membered heterocycloalkyl, and the like, and in various embodiments, $R^1$ and $R^2$ can each, independently, be substituted with at least one Rg group selected from halogen, $C_{1-6}$ alkyl, $C_{1-6}$ haloalkyl, hydroxyl, $C_{1-6}$ alkoxy, $C_{1-6}$ haloalkoxy, amino, $C_{1-6}$alkylamino, or di-$C_{1-6}$alkylamino. In some embodiments, $R^1$ and $R^2$ can each, independently, include a linker heteroatom. For example, $R^1$ and $R^2$ can each, independently, be selected from:

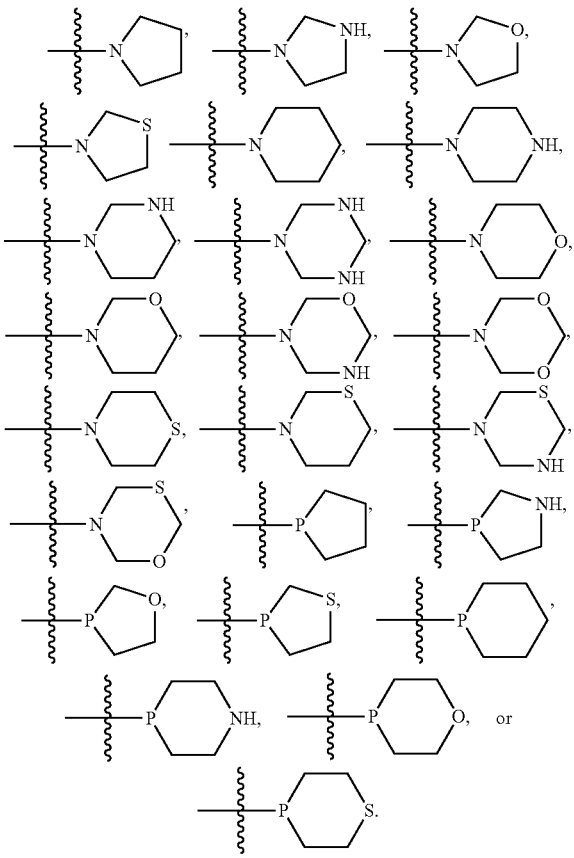

In certain embodiments, each $R^1$ and $R^2$ can, independently, be selected from pyrrolidine and piperidine.

In some embodiments, each Rl and $R^2$ can, independently, be a tertiary amine For example, each $R^1$ and $R^2$ may, independently, be of formula —$NR^3R^4$ where each $R^3$ and $R^4$ is, independently, selected from $C_{1-10}$ alkyl, $C_{1-10}$ alkenyl, or $C_{1-10}$ alkynyl. In some embodiments, $R^3$ and $R^4$ can each, independently, be substituted with at least one substituent selected from halogen, $C_{1-6}$ alkyl, $C_{1-6}$ haloalkyl, hydroxyl, $C_{1-6}$ alkoxy, $C_{1-6}$ haloalkoxy, amino, $C_{1-6}$alkylamino, or di-$C_{1-6}$alkylamino In further embodiments, each $R^1$ and $R^2$ can, independently, be a secondary amine, and in some embodiments, the secondary amine may include a branched $C_{1-10}$ alkyl, $C_{1-10}$ alkenyl, or $C_{1-10}$ alkynyl. In certain embodiments, the branched $C_{1-10}$ alkyl, $C_{1-10}$ alkenyl, or $C_{1-10}$ alkynyl is substituted with at least one substituent selected from the group consisting of halogen, $C_{1-6}$ alkyl, $C_{1-6}$haloalkyl, hydroxyl, $C_{1-6}$ alkoxy, $C_{1-6}$haloalkoxy, amino, $C_{1-6}$alkylamino, and di-$C_{1-6}$alkylamino In various embodiments, described above X may be selected from $CH_2)_s$—NH—$(CH_2)_t$— or —$(CH_2)_s$—O—$(CH_2)_t$—, wherein s and t are each, independently an integer from 1 to 3, and in certain embodiments, X may be —$CH_2$—NH—$CH_2$— or —$CH_2$—O—$CH_2$—. In some embodiments, X may be a branched $C_{1-10}$ alkyl. For example, X may be selected from —$CH(CH_3)CH_2$—, —$CH(CH_3)CH(CH_3)$—, —$CH_2C(CH_3)(CH_3)CH_2$—, —$C(CH_3)(CH_3)$—, or —$CH_2C(CH_3)(CH_3)$—.

In some embodiments, the compounds of the invention may be of Formula Ia:

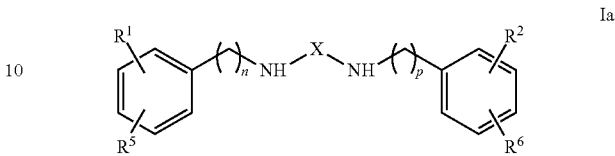

or salts, esters, solvates, hydrates, or prodrugs thereof; wherein X is $C_{1-10}$ alkyl, $(CH_2)_s$—NH—$(CH_2)_t$, or $(CH_2)_s$—O—$(CH_2)_t$, wherein s and t are each, independently, an integer from 1 to 5; $R^1$ and $R^2$ are each, independently, amine, $C_{1-10}$ alkyl, $C_{1-10}$ alkenyl, $C_{1-10}$ alkynyl, $C_{3-7}$ cycloalkyl, $C_{3-7}$ cycloalkyl-$C_{1-6}$alkyl, $C_{3-7}$ heterocycloalkyl, or $C_{3-7}$ heterocycloalkyl-$C_{1-6}$ alkyl; and n and p are each, independently, integers from 1 to 10; and $R^5$ and $R^6$ are each, independently, selected from the group consisting of halogen, $C_{1-6}$ alkyl, $C_{1-6}$ haloalkyl, hydroxyl, $C_{1-6}$ alkoxy, $C_{1-6}$ haloalkoxy, amino, $C_{1-6}$ alkylamino, and di-$C_{1-6}$ alkylamino Any of the various descriptions for $R^1$, $R^2$, and X above may be applied to the compounds of Formula Ia.

Also disclosed herein is a compound of Formula II, or a salt, ester, solvate, hydrate or prodrug thereof:

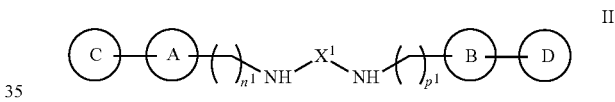

where:

$X^1$ is a branched or unbranched $C_{1-10}$ alkyl, $(CH_2)_s$—NH—$(CH_2)_t$, $(CH_2)_s$—O—$(CH_2)_t$, or $(CH_2)_s$—C(NH_2)—$(CH_2)_v$—NH—$(CH_2)_t$, where s, t and v are each, independently an integer from 1 to 5;

A and B are each, independently, $C_{6-10}$aryl, $C_{6-10}$aryl-$C_{1-6}$alkyl, $C_{3-9}$ heteroaryl, or $C_{3-9}$heteroaryl-$C_{1-6}$alkyl, each optionally substituted with 1, 2 or 3 independently selected $R^g$ groups;

C and D are each, independently, $C_{3-7}$ cycloalkyl, $C_{3-7}$ cycloalkyl-$C_{1-6}$alkyl, $C_{3-7}$ heterocycloalkyl, $C_{3-7}$ heterocycloalkyl-$C_{1-6}$ alkyl, $C_{6-10}$aryl, $C_{6-0}$aryl-$C_{1-6}$alkyl, $C_{3-9}$ heteroaryl, or $C_{3-9}$heteroaryl-$C_{1-6}$alkyl, each optionally substituted with 1, 2 or 3 independently selected $R^g$ groups;

each $R^g$ is, independently, halogen, $C_{1-6}$ alkyl, $C_{1-6}$ haloalkyl, hydroxyl, $C_{1-6}$ alkoxy, $C_{1-6}$ haloalkoxy, amino, $C_{1-6}$alkylamino, or di-$C_{1-6}$alkylamino; and $n^1$ and $p^1$ are each, independently, integers from 1 to 10.

In various embodiments, the compound of Formula I, II or III, or salt, ester, solvate, hydrate, or prodrug, thereof may be administered in an effective amount. In some embodiments, an effective amount may be from about 0.5 mg to about 500 mg of the Formula I or salt, ester, solvate, hydrate, or prodrug thereof, and in certain embodiments, an effective amount may be from about 0.5 mg/kg to about 500 mg/kg of compound per kg of patient body weight. In particular embodiments, administering may include oral administration, administration via implants, parenteral injection, intravenous injection, intraperitoneal injection, subcutaneous injection, bolus injection, infusion, rectal administration, vaginal administration, transdermal administration, inhalation, and the like and combinations thereof. In certain embodiments, the methods may further include the step of administrating at least one anti-inflammatory agents, anti-microbial agents, matrix metalloprotease inhibitors, lipoxygenase inhibitors, cytokine antagonists, immunosuppressants, anti-cancer agents, anti-viral agents, cytokines, growth factors, immunomodulators, prostaglandins, antivascular hyperproliferation compounds, and combinations thereof either concurrently with the compound of Formula I or Ia, II or III or in the same course of treatment.

The foregoing will become more apparent from the following detailed description, which proceeds with reference to the accompanying figures.

BRIEF DESCRIPTION OF THE DRAWINGS

For a better understanding of the disclosure and to show how the same may be carried into effect, reference will now be made to the accompanying drawings. It is stressed that the particulars shown are by way of example only and for purposes of illustrative discussion of the preferred embodiments of the present disclosure only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

FIGS. 1A-1I are a table showing compounds presently disclosed herein.

FIGS. 2A-2B show additional compounds presently disclosed herein.

FIG. 4 shows assay results. 100K viable PBMC per well (96 well format) were seeded in 300 ul media (10% RPMI). Cells were pretreated with compound (1421, 1261, 1563, or 1568) for 4 h (10 pg/ml-10000 pg/ml), before exposed to LPS (10 ng/ml) for additional 2 h. 50 ul of media were collected and diluted to 250 ul and TNF concentration were measured by ELISA (n=6). Compound 1261 has a structure of:

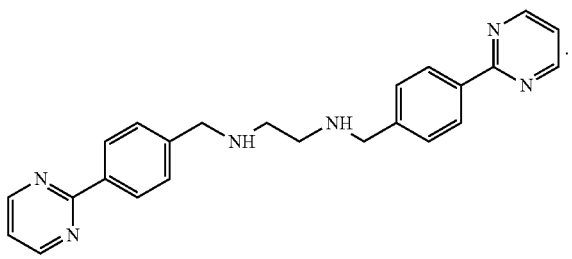 [SMILES: c1cnc(-c2ccc(CNCCNCc3ccc(-c4ncccn4)cc3)cc2)nc1]

Figure 5:
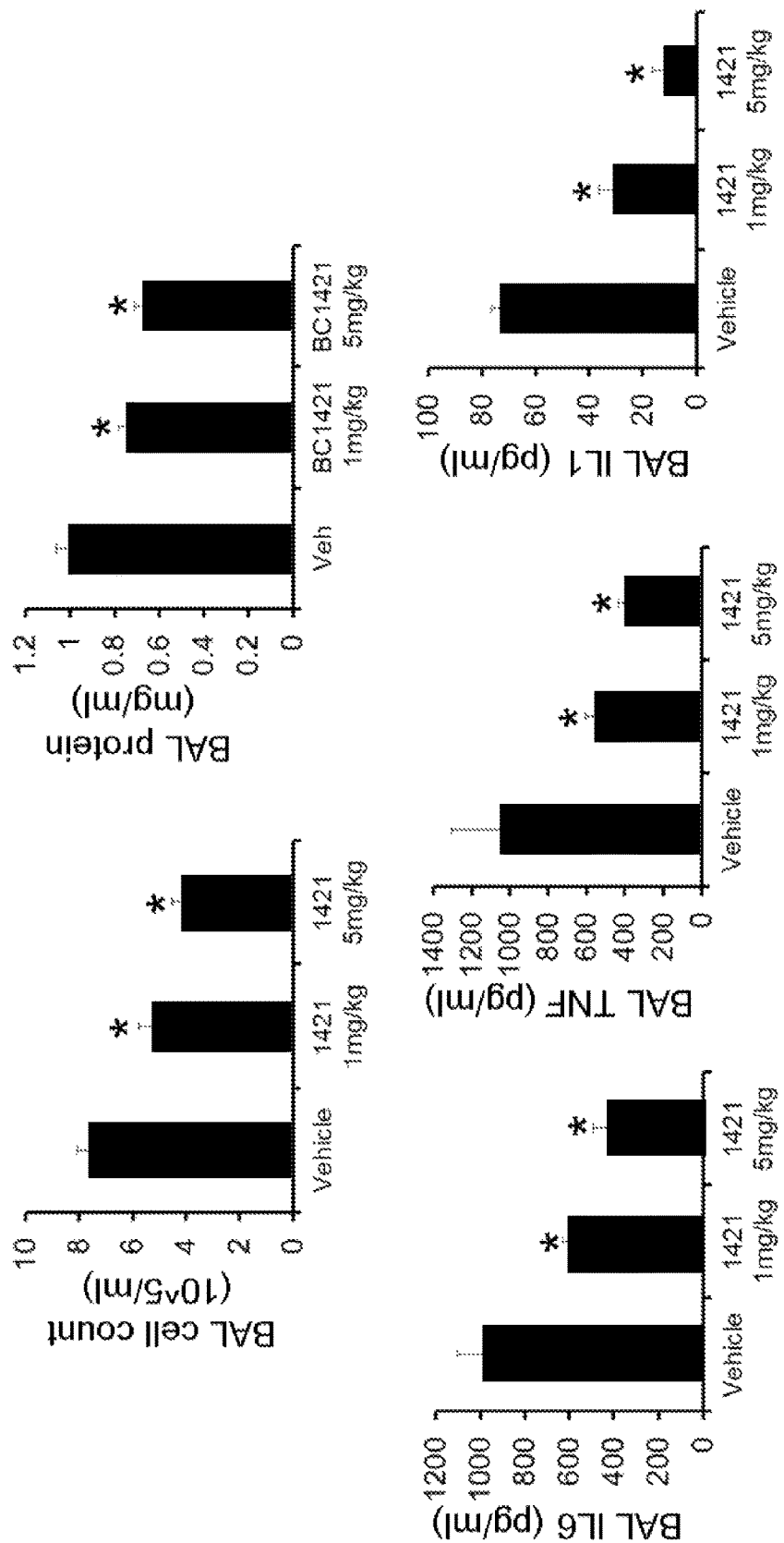

FIG. 5 shows assay results. Compound BC-1421 reduces LPS induced lung inflammation. BC-1421 was administered to mice though P.O., and mice were then immediately challenged with LPS (3 mg/kg, i.t.) for an additional 18 h. Mice were then euthanized and lungs were lavaged with saline, harvested, and then homogenized. Lavage protein, cell counts and cytokine secretion were measured in. The data represent n=4-5 mice/group, *P<0.05 versus Vehicle.

DETAILED DESCRIPTION

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a," "an," and "the" include plural reference unless the context clearly dictates otherwise.

As used herein, the term "about" means plus or minus 10% of the numerical value of the number with which it is being used. Therefore, about 50% means in the range of 45%-55%.

"Optional" or "optionally" may be taken to mean that the subsequently described structure, event or circumstance may or may not occur, and that the description includes instances where the event occurs and instances where it does not.

"Administration" as used herein is inclusive of administration by another person to the subject or self-administration by the subject.

The term "alkyl" by itself or as part of another group refers to a straight and branched saturated carbon chain radical having a having from 1 to 10 carbon atoms. Unless the chain length is otherwise limited, such "alkyl groups" include, but are not limited to, methyl, ethyl, propyl, isopropyl, butyl, s-butyl, t-butyl, isobutyl, pentyl, hexyl, isohexyl, heptyl, 4,4-dimethylpentyl, octyl, 2,2,4-trimethylpentyl, nonyl, and decyl.

The term "alkoxy" or "alkyloxy" refers to any of the above alkyl groups linked to an oxygen atom, represented by the formula —OR where R is an alkyl group. Typical examples of "alkoxy groups" or "alkyloxy groups" include methoxy, ethoxy, n-propyloxy, isopropyloxy, n-butoxy, i-butoxy, sec-butyloxy, and t-butyloxy.

The term "alkoxycarbonyl" refers to an alkoxy substituted carbonyl radical, —C(O)OR, wherein R represents an optionally substituted alkyl, aryl, aralkyl, cycloalkyl, cycloalkylalkyl or similar moiety.

The term "alkenyl" by itself or as part of another group refers to a straight or branched unsaturated carbon chain radical having from 2 to 10 carbon atoms and having at least one double bond between two of the carbon atoms in the chain. Unless the chain length is otherwise limited, such "alkenyl groups" include, but are not limited to, ethenyl, 1-propenyl, 2-propenyl, 2-methyl-1-propenyl, 1-butenyl, 2-butenyl, and the like.

The term "alkynyl" by itself or as part of another group refers to a straight or branched unsaturated carbon chain radical having 2 to 10 carbon atoms and having at least one triple bond between two of the carbon atoms in the chain.

Unless the chain length is otherwise limited, such "alkynyl groups" include, but not limited to, ethynyl, 1-propynyl, 2-propynyl, and the like.

In all instances herein where there is an alkenyl or alkynyl moiety as a substituent group, the unsaturated linkage, i.e., the vinyl or ethenyl linkage, is, generally, not directly attached to a nitrogen, oxygen, or sulfur moiety.

The term "aryl" by itself or as part of another group refers to monocyclic or bicyclic aromatic groups containing from 6 to 12 carbons in the ring portion. Typical examples include phenyl, biphenyl, naphthyl or tetrahydronaphthyl.

The term "aralkyl" or "arylalkyl" by itself or as part of another group refers to $C_{1-6}$ alkyl groups as discussed above having an aryl substituent, such as benzyl, phenylethyl or 2-naphthylmethyl.

"Aryloxy" or "heteroaryloxy" refers to a group of the formula —OAr, wherein Ar is an aryl group or a heteroaryl group, respectively.

"Heteroaryl" as employed herein refers to groups having 5 to 14 ring atoms; 6, 10, or 14 pi electrons shared in a cyclic array; and containing carbon atoms and 1, 2, 3, or 4 oxygen, nitrogen, or sulfur heteroatoms. Examples of heteroaryl groups include, but are not limited to, thienyl, benzo[b]thienyl, naphthol2,3-blthienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, (β-carbolinyl, phenanthridinyl, acridinyl, perimidinyl, phenanthrolinyl, phenazinyl, isothiazolyl, phenothiazinyl, isoxazolyl, furazanyl, phenoxazinyl, and tetrazolyl groups). The aryl or heteroaryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl or heteroaryl group can be unsubstituted.

The terms "heteroarylalkyl" or "heteroaralkyl" as employed herein both refer to a heteroaryl group attached to an alkyl group. Typical examples include 2-(3-pyridyl)ethyl, 3-(2-furyl)-n-propyl, 3-(3-thienyl)-n-propyl, and 4-(1-isoquinolinyl)-n-butyl.

The term "cycloalkyl," by itself or as part of another group, refers to any saturated or partially unsaturated ringed structure containing 3 to 9 carbon atoms. Typical examples are cyclopropyl, cyclobutyl, cyclopentyl, cyclohexyl, cycloheptyl, cyclooctyl and cyclononyl.

The term "cycloalkylalkyl" or "cycloalkyl(alkyl)," by itself or as part of another group, refers to a cycloalkyl group attached to an alkyl group. Typical examples are 2-cyclopentylethyl, cyclohexylmethyl, cyclopentylmethyl, 3-cyclohexyl-n-propyl, and 5-cyclobutyl-n-pentyl.

The term "cycloalkenyl," by itself or as part of another group, refers to a partially unsaturated ringed structure containing 3 to 9 carbon atoms and 1 to 3 carbon-carbon double bonds. Typical examples include cyclopropenyl, cyclobutenyl, cyclopentenyl, cyclohexenyl, cyclohexadienyl, cycloheptenyl, cycloheptadienyl, cyclooctenyl, cyclooctadienyl, cyclooctatrienyl, cyclononenyl, and cyclononadienyl.

The term "heterocycle" or "heterocycloalkyl," by itself or as part of another group, refers to any saturated or partially unsaturated ring system having 5 to 14 ring carbon atoms and 1, 2, 3, or 4 oxygen, nitrogen, or sulfur ring heteroatoms. Typical examples include pyrrolidinyl, imidazolidinyl, pyrazolidinyl, tetrahydrofuranyl, tetrahydropyranyl, piperidyl, piperazinyl, quinuclidinyl, morpholinyl, and dioxacyclohexyl. Typical partially unsaturated examples include pyrrolinyl, imidazolinyl, pyrazolinyl, dihydropyridinyl, tetrahydropyridinyl, and dihydropyranyl. The term "heteroatom" is used to mean an oxygen atom ("O"), a sulfur atom ("S") or a nitrogen atom ("N") that is incorporated into an aliphatic or ringed carbon chain, which may or may not include one or more double bonds. For example, when the heteroatom is nitrogen, it may form an $NR^aR^b$ moiety, where $R^a$ and $R^b$ are, independently, hydrogen or $C_1$ to $C_8$ alkyl, or together with the nitrogen to which they are bound form a saturated or unsaturated 5-, 6-, or 7-membered ring.

"Substituted" or "substitution" refer to replacement of a hydrogen atom of a molecule or an R-group with one or more additional R-groups.

An "R-group" or "substituent" refers to a single atom (for example, a halogen atom) or a group of two or more atoms that are covalently bonded to each other, which are covalently bonded to an atom or atoms in a molecule to satisfy the valency requirements of the atom or atoms of the molecule, typically in place of a hydrogen atom. Examples of R-groups/substituents include, for example, from $C_{1-6}$alkyl, $C_{2-6}$alkenyl, $C_{2-6}$alkynyl, $C_{3-8}$cycloalkyl, hydroxyl, oxo, $C_{1-6}$alkoxy, aryloxy, acyloxy groups, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, mercapto groups, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, ar$C_{1-6}$alkyl, heterocyclyl and heteroaryl wherein each alkyl, alkenyl, alkynyl, cycloalkyl, aryl and heterocyclyl and groups containing them may be further optionally substituted.

Unless otherwise defined, the term "optionally-substituted" or "optional substituent" as used herein refers to a group which may or may not be further substituted with 1, 2, 3, 4 or more groups. Optional substituents in the case N-heterocycles may also include but are not limited to $C_{1-6}$alkyl, i.e., N—$C_{1-3}$alkyl, more preferably methyl particularly N-methyl.

The term "carboxylate" or "carboxyl" refers to the group —COO⁻ or —COOH.

The term "ester" refers to a carboxyl group having the hydrogen replaced with, for example, a $C_{1-6}$alkyl group ("carboxyl$C_{1-6}$alkyl" or "alkylester"), an aryl or aralkyl group ("arylester" or "aralkylester") and so on. CO2C1-3alkyl groups are preferred, such as for example, methylester (CO 2Me), ethylester (CO2Et) and propylester (CO$_2$Pr) and includes reverse esters thereof (e.g. —OCOMe, —OCOEt and —OCOPr).

The term "halogen" refers to fluoro, bromo, chloro and iodo substituents.

The terms "halogenated alkyl" or "haloalkyl group" refer to an alkyl group as defined above with one or more hydrogen atoms present on these groups substituted with a halogen (F, Cl, Br, I).

"Nitro" refers to an R-group having the structure —$NO_2$.

The terms "hydroxyl" and "hydroxyl" are used interchangeably to refer to the radical —OH.

The terms "carbamoyl" and "aminocarbonyl" are used interchangeably to refer to the radical $NH_2$—C(O)—.

"Acyl" refers to a group having the structure —C(O)R, where R may be, for example, optionally substituted alkyl, optionally substituted aryl, or optionally substituted heteroaryl.

"Acyloxy" refers to a group having the structure —OC(O)R—, where R may be, for example, optionally substituted alkyl, optionally substituted aryl, or optionally substituted heteroaryl.

The term "amine" or "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group. For example, an "alkylamino" or "alkylated amino" refers to —NRR', wherein at least one of R or R' is an alkyl.

"Aminocarbonyl" alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —N(R)—C(O)—R (wherein R is a substituted group or H).

The term "amide" or "amido" is represented by the formula —C(O)NRR', where R and R' independently can be a hydrogen, alkyl, alkenyl, alkynyl, aryl, aralkyl, cycloalkyl, halogenated alkyl, or heterocycloalkyl group described above.

An "analog" is a molecule that differs in chemical structure from a parent compound, for example a homolog (differing by an increment in the chemical structure or mass, such as a difference in the length of an alkyl chain or the inclusion of one of more isotopes), a molecular fragment, a structure that differs by one or more functional groups, or a change in ionization. An analog is not necessarily synthesized from the parent compound. A derivative is a molecule derived from the base structure.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

The term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

"Inhibiting" refers to inhibiting the full development of a disease or condition.

"Inhibiting" also refers to any quantitative or qualitative reduction in biological activity or binding, relative to a control.

The term "co-administration" or "co-administering" refers to administration of a compound or composition disclosed herein with at least one other therapeutic agent within the same general time period, and does not require administration at the same exact moment in time (although co-administration is inclusive of administering at the same exact moment in time). Thus, co-administration may be on the same day or on different days, or in the same week or in different weeks. The additional therapeutic agent may be included in the same composition as the compound disclosed herein.

A "therapeutically effective amount" refers to a quantity of a specified agent sufficient to achieve a desired effect in a subject being treated with that agent. For example, a therapeutically amount of a compound disclosed herein is an amount sufficient to inhibit inflammation in a subject. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease, for example, in a subject who is at risk for a disease such as cancer. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition. In certain embodiments disclosed herein, the treatment inhibits inflammation in a subject.

Embodiments of the invention are directed to benzathine based compounds and pharmaceutical compositions that include these benzathine based compounds for treating, for example, lung related injury and disease, or inflammation related injury, disease or condition. Other embodiments are directed to methods for treating lung related injuries or diseases, or inflammation related injury, disease or conditions, using these compounds and compositions, and methods for making compounds and pharmaceutical compositions including the benzathine based compounds. In certain embodiments, the compounds disclosed herein are FBXO3 inhibitors.

The compounds of some embodiments may be of general Formula I:

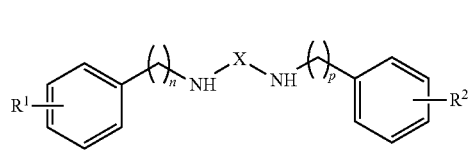

I where:

X is a branched or unbranched $C_{1-10}$ alkyl, $(CH_2)_s$—NH—$(CH_2)_t$, or $(CH_2)_s$—O—$(CH_2)_t$, where s and t are each, independently an integer from 1 to 5;

$R^1$ and $R^2$ are each, independently, $C_{1-10}$ alkyl, $C_{1-10}$ alkenyl, $C_{1-10}$ alkynyl, $C_{3-7}$ cycloalkyl, $C_{3-7}$ cycloalkyl-$C_{1-6}$alkyl, $C_{3-7}$ heterocycloalkyl, or $C_{3-7}$ heterocycloalkyl-$C_{1-6}$ alkyl, each of which can be optionally substituted with 1, 2 or 3 independently selected $R^g$ groups;

each $R^g$ is, independently, halogen, $C_{1-6}$ alkyl, $C_{1-6}$ haloalkyl, hydroxyl, $C_{1-6}$ alkoxy, $C_{1-6}$ haloalkoxy, amino, $C_{1-6}$alkylamino, or di-$C_{1-6}$alkylamino; and n and p are each, independently, integers from 1 to 10.

In various embodiments, $R^1$ and $R^2$ can be the same or different. Each of $R^1$ and $R^2$ can be substituted at any position on each phenyl ring. For example, $R^1$ and $R^2$ can be positioned in the ortho (o), meta (m), or para (p) position relative to the diamine connector portion of the molecule. In certain embodiments, each of $R^1$ and $R^2$ may be in para position.

In some embodiments, $R^1$, $R^2$, or both $R^1$ and $R^2$ 6-membered cycloalkyl, 6-membered heterocycloalkyl, 5-membered cycloalkyl, or 5-membered heterocycloalkyl. In certain embodiments, these cycloalkyl and heterocycloalkyl can be saturated, i.e., unsubstituted, and in other embodiments, each of $R^1$ and $R^2$ may be substituted with one or more $R^g$ groups. When $R^1$ or $R^2$ are heterocycloalkyl the heteroatom may be positioned anywhere on the cyclic ring, and in some embodiments, the heteroatom may form a bond to the phenyl on the base structure. For example, the nitrogen of a pyrrolidine may bond to a carbon of the phenyl ring of the based structure as well as bonding to the 2 position and 5 position carbons of the pyrrolidine ring. Such heteroatoms that form a bond to the phenyl of the base structure will be referred to herein as a "linker heteroatom." Examples, of linker heteroatom containing $R^1$ and $R^2$ groups include, but are not limited to:

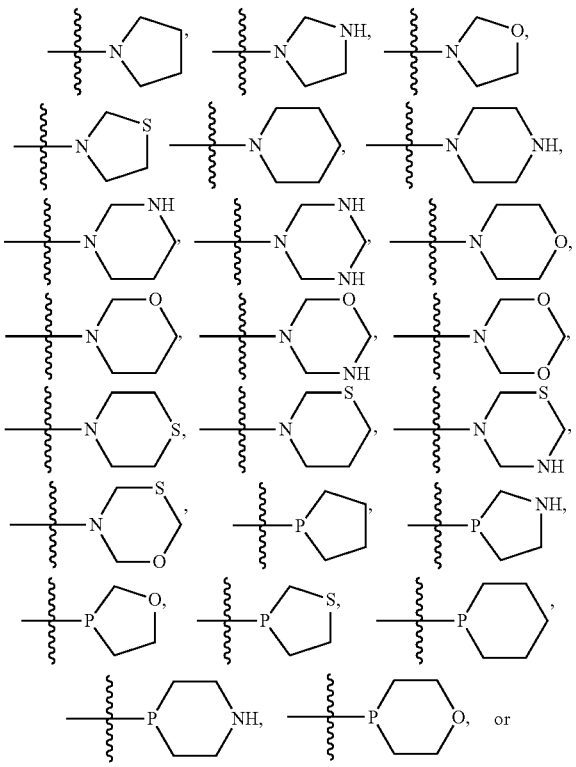

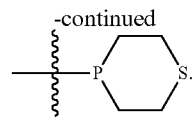

In particular embodiments, each of $R^1$ and $R^2$ may be pyrrolidine or piperidine, and in certain embodiments, both $R^1$ and $R^2$ may be either pyrrolidine or piperidine.

In some embodiments, $R^1$, $R^2$, or both $R^1$ and $R^2$ can be a tertiary amine. For example, in particular embodiments, $R^1$, $R^2$, or both $R^1$ and $R^2$ can be or general structure —$NR^3R^4$ where each of $R^3$ and $R^4$ can each, independently, be a $C_{1-10}$ alkyl, $C_{1-10}$ alkenyl, $C_{1-10}$ alkynyl $C_{3-10}$ aryl, $C_{3-10}$ aryl-$C_{1-6}$alkyl, $C_{3-10}$ heteroaryl, $C_{3-10}$ heteroaryl-$C_{1-6}$alkyl, $C_{3-7}$ cycloalkyl, $C_{3-7}$ cycloalkyl-$C_{1-6}$alkyl, $C_{3-7}$ heterocycloalkyl, or $C_{3-7}$ heterocycloalkyl-$C_{1-6}$ alkyl each of which can be unsubstituted or substituted with one or more halogen, $C_{1-6}$ alkyl, $C_{1-6}$haloalkyl, hydroxyl, $C_{1-6}$ alkoxy, $C_{1-6}$ haloalkoxy, amino, $C_{1-6}$alkylamino, or di-$C_{1-6}$alkylamino In certain embodiments, $R^3$ and $R^4$ can each, independently, be an unsubstituted $C_{1-10}$ alkyl, $C_{2-6}$ alkyl, or a $C_4$ alkyl, and in some embodiments, $R^3$ and $R^4$ can each, independently, be an unsubstituted $C_{6-8}$ aryl, or $C_{6-8}$ heteroaryl.

In certain embodiments, $R^1$, $R^2$, or both $R^1$ and $R^2$ can be a secondary amine having a branched or unbranched $C_{1-10}$ alkyl, $C_{1-10}$ alkenyl, or $C_{1-10}$ alkynyl that can be unsubstituted or substituted with one or more halogen, $C_{1-6}$ alkyl, $C_{1-6}$ haloalkyl, hydroxyl, $C_{1-6}$ alkoxy, $C_{1-6}$ haloalkoxy, amino, $C_{1-6}$alkylamino, or di-$C_{1-6}$alkylamino In particular embodiments, $R^3$ and $R^4$ may be, for example, 3-aminononane, 4-aminononane, 5-aminononane, 3-aminooctane, 4-aminooctane, 2-aminoheptane, 3-aminoheptane, 4-aminoheptane, 2-aminohexane, 3-aminohexane, 2-aminopentane, 3-aminopentane, and the like and substituted versions thereof.

In some embodiments, $R^1$, $R^2$, or both $R^1$ and $R^2$ can be a branched $C_{1-10}$ alkyl, $C_{1-10}$ alkenyl, $C_{1-10}$ alkynyl that can be unsubstituted or substituted with one or more halogen, $C_{1-6}$ alkyl, $C_{1-6}$ haloalkyl, hydroxyl, $C_{1-6}$ alkoxy, $C_{1-6}$ haloalkoxy, amino, $C_{1-6}$alkylamino, or di-$C_{1-6}$alkylamino In certain embodiments, $R^1$, $R^2$, or both $R^1$ and $R^2$ can be a branched $C_{1-10}$ alkyl. For example, in particular embodiments, each $R^1$, $R^2$, or both $R^1$ and $R^2$ can be 2-nonane, 4-nonane, 5-nonane, 3-octane, 4-octane, 2-heptane, 3-heptane, 4-heptane, 2-hexane, 3-hexane, 2-pentane, 3-aminopentane, or the like and substituted versions thereof.

Various embodiments include any combination of different $R^1$ and $R^2$ described above. For example, in some embodiments, $R^1$ can be a cycloalkyl or heterocycloalkyl, and $R^2$ can be a tertiary amine, secondary amine, or branched $C_{1-10}$ alkyl. In other embodiments, $R^1$ can be a tertiary amine or secondary amine, and $R^2$ can be a branched $C_{1-10}$ alkyl. Embodiments of the invention embrace all combinations of $R^1$ and $R^2$ described above.

In certain embodiments, X may —$(CH_2)_s$—NH—$(CH_2)_t$— or —$(CH_2)_s$—O—$(CH_2)_t$—, where s and t are each, independently an integer from 1 to 3, and in particular embodiments, s and t may be 1 or 2. Thus, in some embodiments, X may be —$CH_2$—NH—$CH_2$— or —$CH_2$—O—$CH_2$—.

Where X is $C_{1-10}$ alkyl, the $C_{1-10}$ alkyl may be branched or unbranched, and in certain embodiments, the $C_{1-10}$ alkyl may be branched. While the size and character of the branches may vary among embodiments, in certain embodiments, each branch point may include be a methyl, ethyl, propyl, or butyl. Such branches may occur at one or more places on the alkyl chain linking the amines of the diamine linker. For example, a $C_3$-alkyl, $C_4$-alkyl, or a $C_5$-alkyl chain connecting the amines may include two separate methyl, ethyl, or propyl branches on adjacent or non-adjacent carbons, and in other embodiments, two methyl, ethyl, or propyl branches may extend from a single carbon on a $C_3$-alkyl, $C_4$-alkyl, or a $C_5$-alkyl chain connecting the amines. Examples of X encompassed by the definition above include, but are not limited to, —CH($CH_3$)$CH_2$—, —CH($CH_3$)CH($CH_3$)—, —$CH_2$C($CH_3$)($CH_3$)$CH_2$—, —C($CH_3$)($CH_3$)—, —$CH_2$C($CH_3$)($CH_3$)—, and the like. Thus, in various embodiments, X may be $C_{1-8}$ alkyl, $C_{1-6}$ alkyl, $C_{1-5}$ alkyl, or $C_{1-6}$ alkyl.

In various embodiments, n and p may be the same or different. For example, in some embodiments, n and p may, independently be integers from 1 to 8, 1 to 6, or 2 to 10. In particular embodiment, n and p may be the same and may be 1 to 3, and in certain embodiments, n and p may be 1.

In other embodiments, each phenyl ring may be additionally substituted with at least one substituent other than those encompassed by $R^1$ and $R^2$. Thus, embodiments encompass compounds of Formulae Ia:

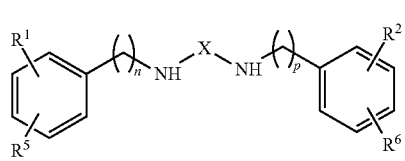

Ia where $R^1$, $R^2$, X, n, and p are defined as described in the various embodiments described above, and $R^5$ and $R^6$ are each, independently, halogen, $C_{1-6}$ alkyl, $C_{1-6}$ haloalkyl, hydroxyl, $C_{1-6}$ alkoxy, $C_{1-6}$ haloalkoxy, amino, $C_{1-6}$alkylamino, or di-$C_{1-6}$alkylamino In particular embodiments, $R^5$ and $R^6$ may each, independently, be halogen or methyl. In some embodiments, the phenyl rings of compounds of Formula Ia may be substituted with one $R^5$, $R^6$, or both $R^5$ and $R^6$, and in other embodiments, the compounds of Formula Ia may be substituted with two or three $R^5$, $R^6$, or both $R^5$ and $R^6$.

The various embodiments described above encompass all stereoisomers and optical isomers of the compounds described above including all individual enantiomers, any mixtures of enantiomers, and diastereomers that can arise as a consequence of structural asymmetry of atoms. Embodiments further include purified enantiomers that may or may not contain residual non-selected enantiomer or diastereomer. Accordingly, compounds and compositions may be provided as individual pure enantiomers or as stereoisomeric mixtures, including racemic mixtures. In certain embodiments, the compounds disclosed herein are synthesized in or are purified to be in substantially pure form such as in a 90% enantiomeric excess, a 95% enantiomeric excess, a 97% enantiomeric excess or even in greater than a 99% enantiomeric excess, such as in enantiopure form.

Examples of the compounds encompassed by the Formulae I and Ia are provided in TABLE 1:

TABLE 1

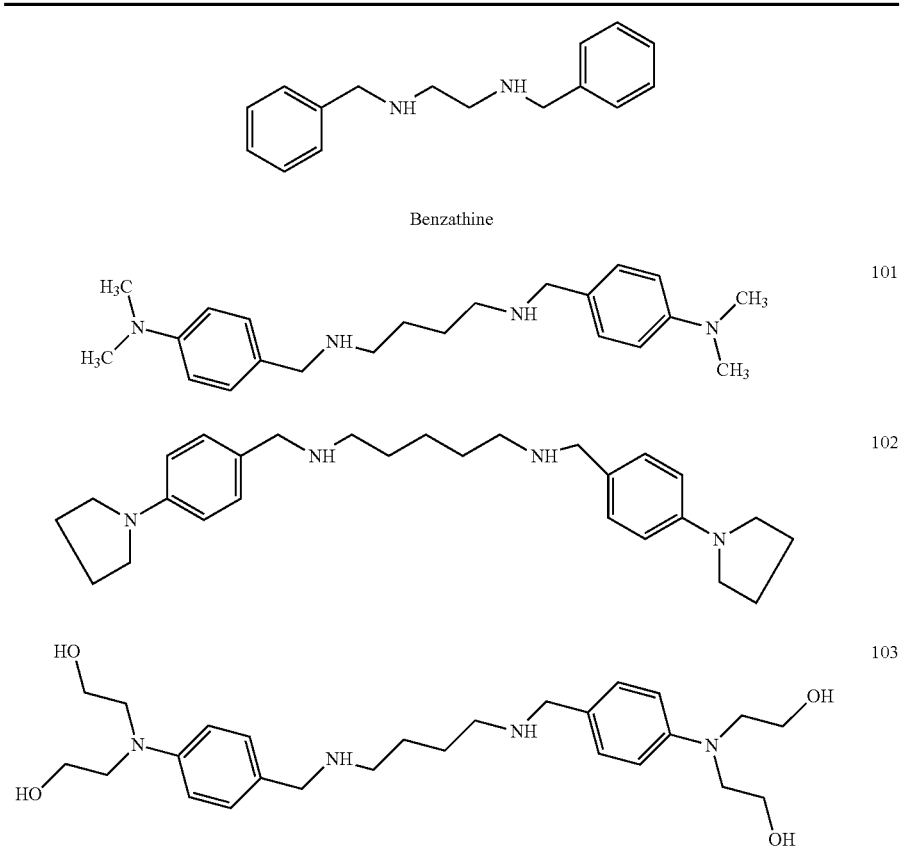

TABLE 1-continued
| | |
|---|---|
| 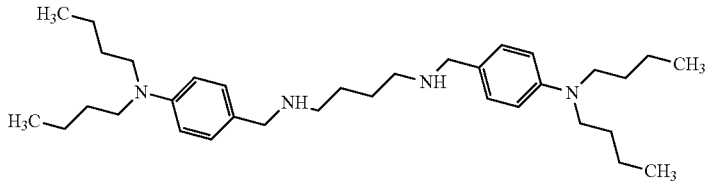 [SMILES: CCCCN(CCCC)c1ccc(CNCCCCNCc2ccc(N(CCCC)CCCC)cc2)cc1] | 104 |
| 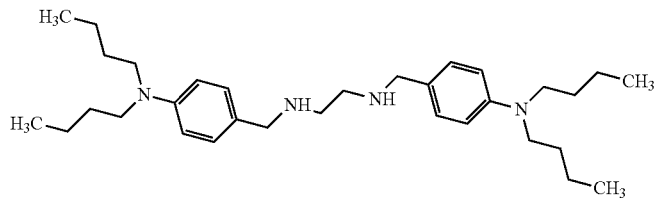 [SMILES: CCCCN(CCCC)c1ccc(CNCCNCc2ccc(N(CCCC)CCCC)cc2)cc1] | 105 |
| 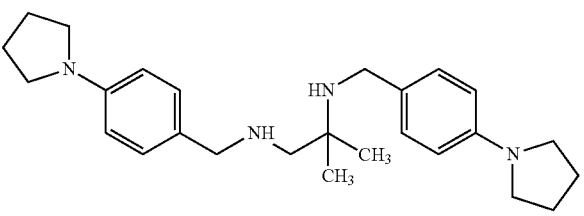 [SMILES: CC(C)(CNCc1ccc(N2CCCC2)cc1)NCc1ccc(N2CCCC2)cc1] | 106 |
| 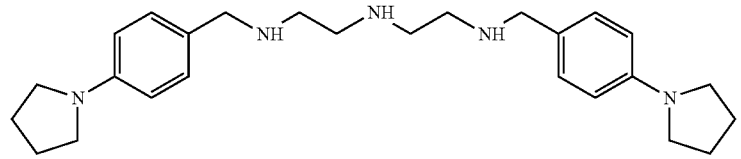 [SMILES: c1cc(N2CCCC2)ccc1CNCCNCCNCc1ccc(N2CCCC2)cc1] | 107 |
| 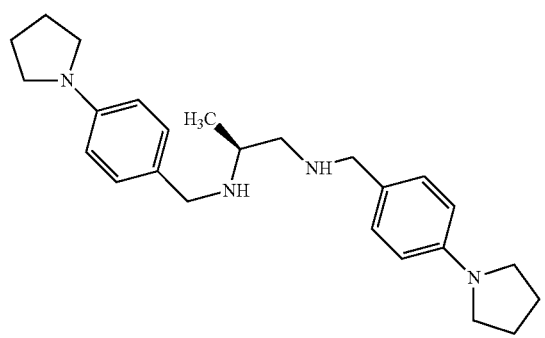 [SMILES: C[C@@H](CNCc1ccc(N2CCCC2)cc1)NCc1ccc(N2CCCC2)cc1] | 108 |
| 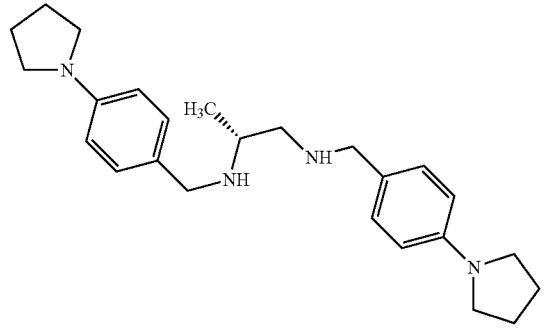 [SMILES: C[C@H](CNCc1ccc(N2CCCC2)cc1)NCc1ccc(N2CCCC2)cc1] | 109 |

TABLE 1-continued
| | |
|---|---|
| 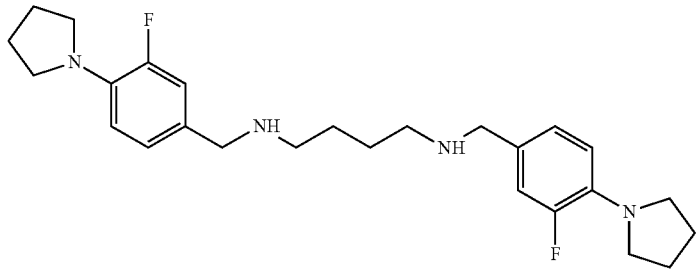 [SMILES: Fc1cc(CNCCCCNCc2ccc(N3CCCC3)c(F)c2)ccc1N1CCCC1] | 110 |
| 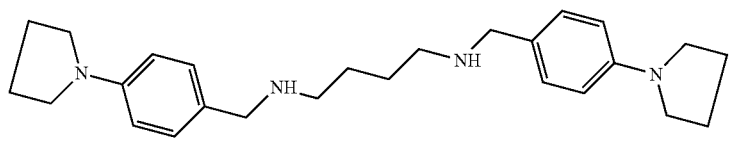 [SMILES: c1cc(N2CCCC2)ccc1CNCCCCNCc1ccc(N2CCCC2)cc1] | 111 |
| 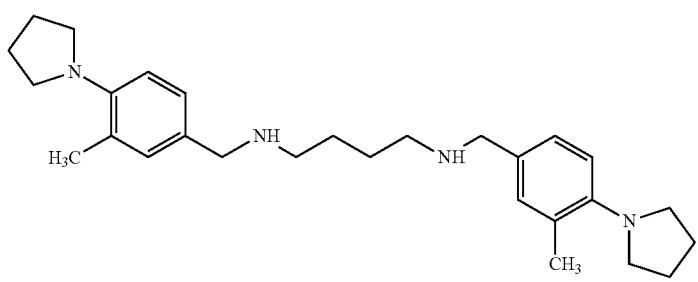 [SMILES: Cc1cc(CNCCCCNCc2ccc(N3CCCC3)c(C)c2)ccc1N1CCCC1] | 112 |
| 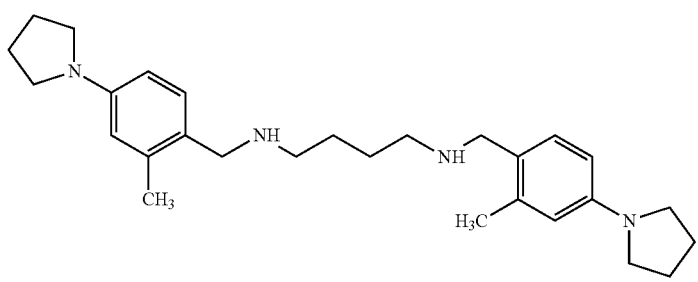 [SMILES: Cc1cc(N2CCCC2)ccc1CNCCCCNCc1ccc(N2CCCC2)cc1C] | 113 |
| 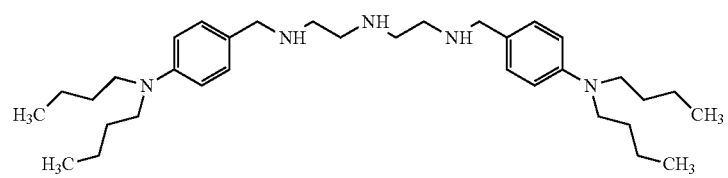 | 114 |
| 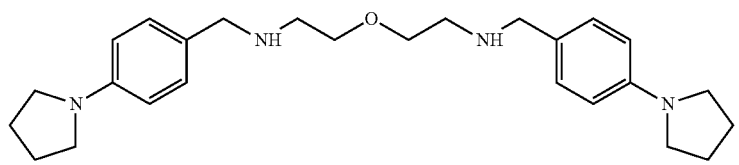 [SMILES: c1cc(N2CCCC2)ccc1CNCCOCCNCc1ccc(N2CCCC2)cc1] | 115 |
| 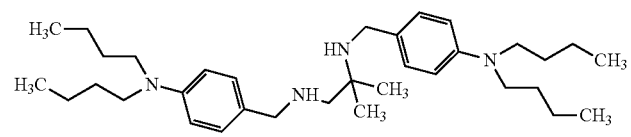 [SMILES: CCCCN(CCCC)c1ccc(CNCC(C)(C)NCc2ccc(N(CCCC)CCCC)cc2)cc1] | 116 |

TABLE 1-continued

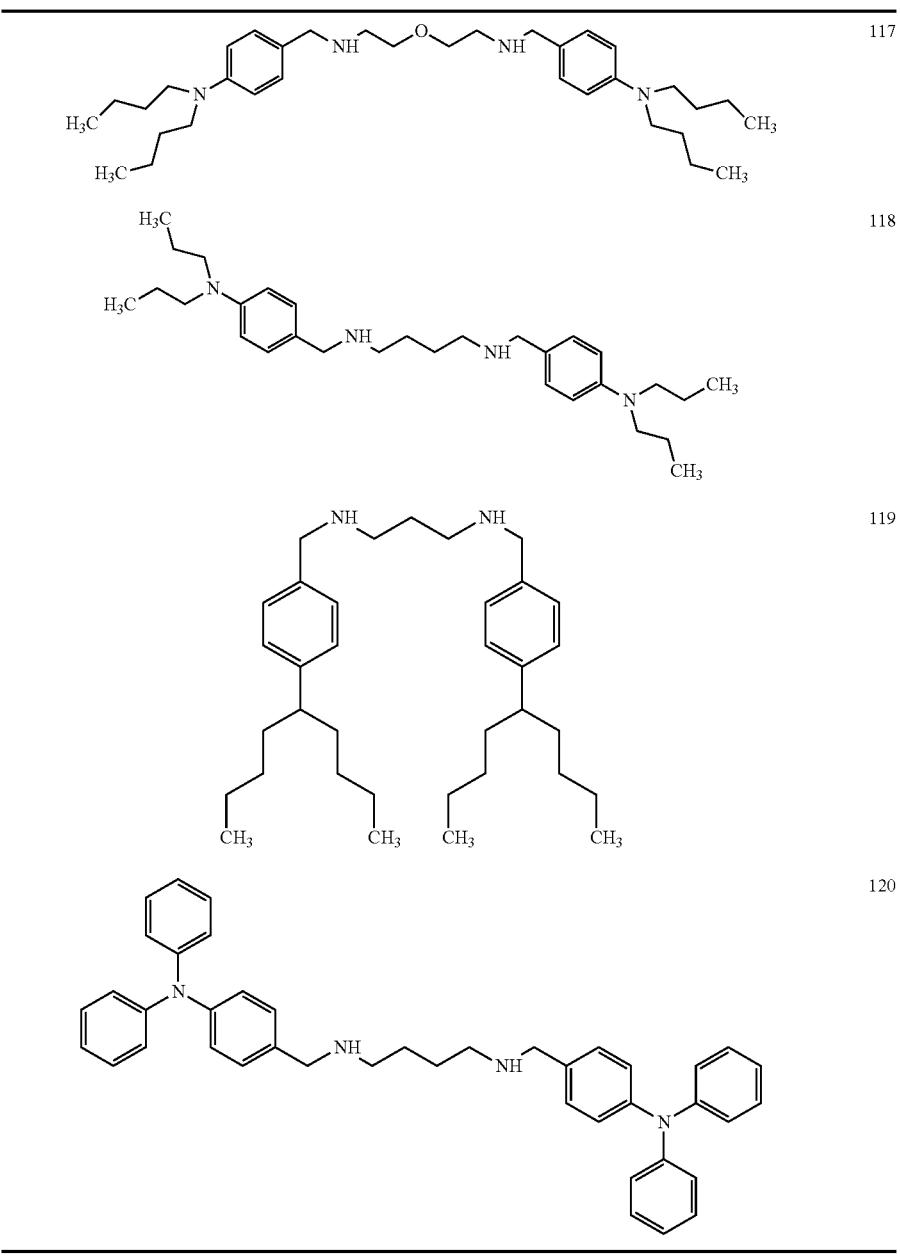

Additional embodiments are directed to compounds of Formula II, or a salt, ester, solvate, hydrate or prodrug thereof:

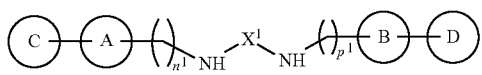

II where:

$X^1$ is a branched or unbranched $C_{1-10}$ alkyl, $(CH_2)_s$—NH—$(CH_2)_t$, $(CH_2)_s$—O—$(CH_2)_t$, or $(CH_2)_s$—C(NH$_2$)—$(CH_2)_v$—NH—$(CH_2)_t$, where s, t and v are each, independently an integer from 1 to 5;

A and B are each, independently, $C_{6-10}$aryl, $C_{6-10}$aryl-$C_{1-6}$alkyl, $C_{3-9}$ heteroaryl, or $C_{3-9}$heteroaryl-$C_{1-6}$alkyl, each optionally substituted with 1, 2 or 3 independently selected $R^g$ groups;

C and D are each, independently, $C_{3-7}$ cycloalkyl, $C_{3-7}$ cycloalkyl-$C_{1-6}$alkyl, $C_{3-7}$ heterocycloalkyl, $C_{3-7}$ heterocycloalkyl-$C_{1-6}$ alkyl, $C_{6-10}$aryl, $C_{6-10}$aryl-$C_{1-6}$alkyl, $C_{3-9}$ heteroaryl, or $C_{3-9}$heteroaryl-$C_{1-6}$alkyl, each optionally substituted with 1, 2 or 3 independently selected $R^g$ groups;

each $R^g$ is, independently, halogen, $C_{1-6}$ alkyl, $C_{1-6}$haloalkyl, hydroxyl, $C_{1-6}$ alkoxy, $C_{1-6}$haloalkoxy, amino, $C_{1-6}$alkylamino, or di-$C_{1-6}$alkylamino; and $n^1$ and $p^1$ are each, independently, integers from 1 to 10.

In various embodiments, A and B can be the same or different. In some embodiments, each A and B may, independently, be a cyclohexyl, phenyl, 6-membered heteroaryl, 6-membered heterocycloalkyl, cyclopentyl, cyclopentene, cyclopentadiene, 5-membered heteroaryl, or 5-membered heterocycloalkyl each of which may be substituted with one or more $R^g$ groups. In certain embodiments, $R^g$ is halogen, particularly fluorine. Various examples of 6-membered heteroaryl, 6-membered heterocycloalkyl, 5-membered heteroaryl, and 5-membered heterocycloalkyl are provided above with reference to the term "heterocycle." In certain embodiments, A and B may each, independently, be 6-membered heteroaryl, 6-membered heterocycloalkyl, 5-membered heteroaryl, or 5-membered heterocycloalkyl such as, but not limited to, pyrrolyl, H-pyrrolyl, pyrrolinyl, pyrrolidinyl, oxazolyl, oxadiazolyl, (including 1,2,3; 1,2,4; and 1,3,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), dithiazolyl, pyridyl, pyrimidinyl, pyridazinyl, pyrazinyl, pyranyl, thiopyranyl, piperidinyl, morpholinyl, thiomorpholinyl, piperazinyl, and triazinyl. In particular embodiments, each A and B may, independently, be imidazolyl, pyridyl, pyrazolyl, oxadiazolyl or pyrimidinyl.

C and D can be the same or different and can be any ringed structure. For example, in some embodiments, each A and B may, independently, be a cyclohexyl, phenyl, 6-membered heteroaryl, 6-membered heterocycloalkyl, cyclopentyl, cyclopentene, cyclopentadiene, 5-membered heteroaryl, or 5-membered heterocycloalkyl each of which may be substituted with one or more $R^g$ groups. Various examples of 6-membered heteroaryl, 6-membered heterocycloalkyl, 5-membered heteroaryl, and 5-membered heterocycloalkyl are provided above with reference to the term "heterocycle." In certain embodiments, A and B may each, independently, be 6-membered heteroaryl, 6-membered heterocycloalkyl, 5-membered heteroaryl, and 5-membered heterocycloalkyl such as, but not limited to, pyrrolyl, H-pyrrolyl, pyrrolinyl, pyrrolidinyl, oxazolyl, oxadiazolyl, (including 1,2,3; 1,2,4; and 1,3,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), dithiazolyl, pyridyl, pyrimidinyl, pyridazinyl, pyrazinyl, pyranyl, thiopyranyl, piperidinyl, morpholinyl, thiomorpholinyl, piperazinyl, and triazinyl. In particular embodiments, each A and B may, independently, be imidazolyl, pyridyl, pyrazolyl, oxadiazolyl or pyrimidinyl.

Each of C and D can be substituted at any position on A and B, respectively. For example, C and D can be positioned in the ortho (o), meta (m), or para (p) position on A and B relative to the diamine connector portion of the molecule. In certain embodiments, each of C and D may be in para position.

In particular embodiments, when A and B are phenyl C and D may be 6-membered heteroaryl or 5-membered heteroaryl each of which may be substituted with one or more Rg groups, and in certain embodiments, C and D may be 6-membered heteroaryl or 5-membered heteroaryl having two or more heteroatoms when A and B are phenyl. In certain embodiments, Rg is halogen, particularly fluorine, or $C_{1-6}$ alkyl. For example, in some embodiments, when A and B are phenyl, C and D may be C and D may be triazole, oxadiazole, pyrimidine, or triazine with heteroatoms in any configuration, and in particular embodiments, C and D may be:

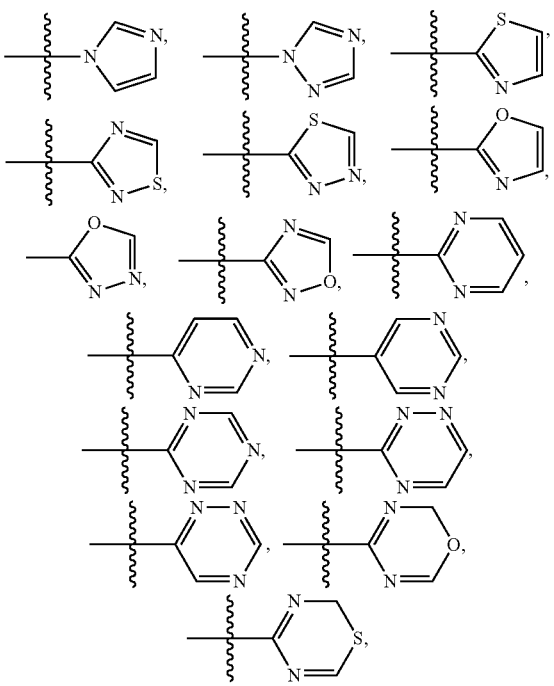

and the like.

In some embodiments, A and B each, independently, may be a 6-membered heteroaryl and C and D may each, independently, be any ringed structure such as, for example, cyclohexyl, phenyl, 6-membered heteroaryl, 6-membered heterocycloalkyl, cyclopentyl, cyclopentene, cyclopentadiene, 5-membered heteroaryl, or 5-membered heterocycloalkyl each of which may be substituted with one or more Rg groups. In such embodiments, A and B may be any pyridine or pyrimidine with heteroatoms in any configuration. In embodiments in which A and B are 6-membered heteroaryl, C and D can be any of the ringed structures described above including for example, phenyl, cyclopentyl, cyclohexyl, pyrrolyl, H-pyrrolyl, pyrrolinyl, pyrrolidinyl, oxazolyl, oxadiazolyl, (including 1,2,3; 1,2,4; and 1,3,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), dithiazolyl, pyridyl, pyrimidinyl, pyridazinyl, pyrazinyl, pyranyl, thiopyranyl, piperidinyl, morpholinyl, thiomorpholinyl, piperazinyl, or triazinyl.

In certain embodiments, $X^1$ may $—(CH_2)_s—NH—(CH_2)_t—$ or $—(CH_2)_s—O—(CH_2)_t—$, where s and t are each, independently an integer from 1 to 3, and in particular embodiments, s and t may be 1 or 2. Thus, in some embodiments, $X^1$ may be $—CH_2—NH—CH_2—$ or $—CH_2—O—CH_2—$.

Where $X^1$ is $C_{1-10}$ alkyl, the $C_{1-10}$ alkyl may be branched or unbranched, and in certain embodiments, the $C_{1-10}$ alkyl may be branched. While the size and character of the branches may vary among embodiments, in certain embodiments, each branch point may include be a methyl, ethyl, propyl, or butyl. Such branches may occur at one or more places on the alkyl chain linking the amines of the diamine linker. For example, a $C_3$-alkyl, $C_4$-alkyl, or a $C_5$-alkyl chain connecting the amines may include two separate methyl, ethyl, or propyl branches on adjacent or non-adjacent carbons, and in other embodiments, two methyl, ethyl, or propyl branches may extend from a single carbon on a $C_3$-alkyl, $C_4$-alkyl, or a $C_5$-alkyl chain connecting the amines. Examples of $X^1$ encompassed by the definition above include, but are not limited to, —CH(CH$_3$)CH$_2$—, —CH(CH$_3$)CH(CH$_3$)—, —CH$_2$C(CH$_3$)(CH$_3$)CH$_2$—, —C(CH$_3$)(CH$_3$)—, —CH$_2$C(CH$_3$)(CH$_3$)—, and the like. Thus, in various embodiments, $X^1$ may be $C_{1-8}$ alkyl, $C_{1-6}$ alkyl, $C_{1-5}$ alkyl, or $C_{1-6}$ alkyl.

In various embodiments, $n^1$ and $p^1$ may be the same or different. For example, in some embodiments, $n^1$ and $_1)^1$ may, independently be integers from 1 to 8, 1 to 6, or 2 to 10. In particular embodiment, $n^1$ and $p^1$ may be the same and may be 1 to 3, and in certain embodiments, $n^1$ and $p^1$ may be 1.

In certain embodiments, A and B are each phenyl, each optionally substituted with 1, 2 or 3 independently selected Rg groups, preferably halogen, more preferably fluorine.

In certain embodiments, A and B are each phenyl, each independently substituted with 1 R$^g$ groups, preferably halogen, more preferably fluorine.

In certain embodiments, C and D are each, independently $C_{3-9}$ heteroaryl, each optionally substituted with 1, 2 or 3 independently selected R$^g$ groups.

In certain embodiments, C and D are each, independently pyrimidinyl, each optionally substituted with 1, 2 or 3 independently selected R$^g$ groups.

In certain embodiments, C and D are each, independently pyrimidinyl, substituted with 1, 2 or 3 independently selected R$^g$ groups, wherein R$^g$ is halogen.

Also disclosed herein are compounds of Formula IV, or a salt, ester, solvate, hydrate or prodrug thereof:

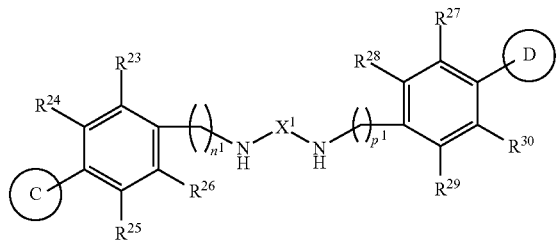

wherein $R^{23}$-$R^{30}$ are each independently hydrogen, halogen, or $C_{1-6}$ haloalkyl; and C, D, $n^1$, $X^1$, and $p^1$ are as described in connection with formula II. In certain embodiments, at least one of $R^{23}$-$R^{30}$ is halogen, preferably fluorine. In particular, $R^{25}$ and $R^{30}$ are fluorine. For example, $R^{25}$ and $R^{30}$ are fluorine and $R^{23}$, $R^{24}$, $R^{26}$, $R^{27}$, $R^{28}$ and $R^{29}$ are hydrogen. In certain embodiments, $R^{25}$ is fluorine. In certain embodiments, $R^{26}$ and $R^{29}$ are fluorine. For example, $R^{26}$ and $R^{29}$ are fluorine and $R^{23}$, $R^{24}$, $R^{25}$, $R^{27}$, $R^{28}$ and $R^{30}$ are hydrogen. In certain embodiments, $n^1$ and $p^1$ are each one. In certain embodiments, $X^1$ is —CH$_2$CH$_2$—. In certain embodiments, C and D are each, independently pyrimidinyl, each optionally substituted with 1, 2 or 3 independently selected Rg groups.

Also disclosed herein are compounds of Formula IVa, or a salt, ester, solvate, hydrate or prodrug thereof:

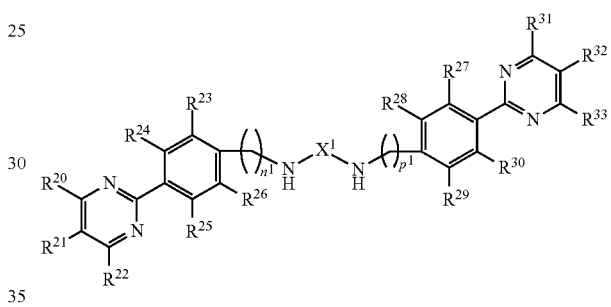

wherein $R^{20}$—$R^{33}$ are each independently hydrogen, halogen, or $C_{1-6}$ haloalkyl; and $n^1$, $X^1$, and $p^1$ are as described in connection with formula II. In certain embodiments, at least one of $R^{20}$—$R^{33}$ is halogen, preferably fluorine. In certain embodiments, $R^{21}$ and $R^{22}$ are each fluorine.

Figure 1B:
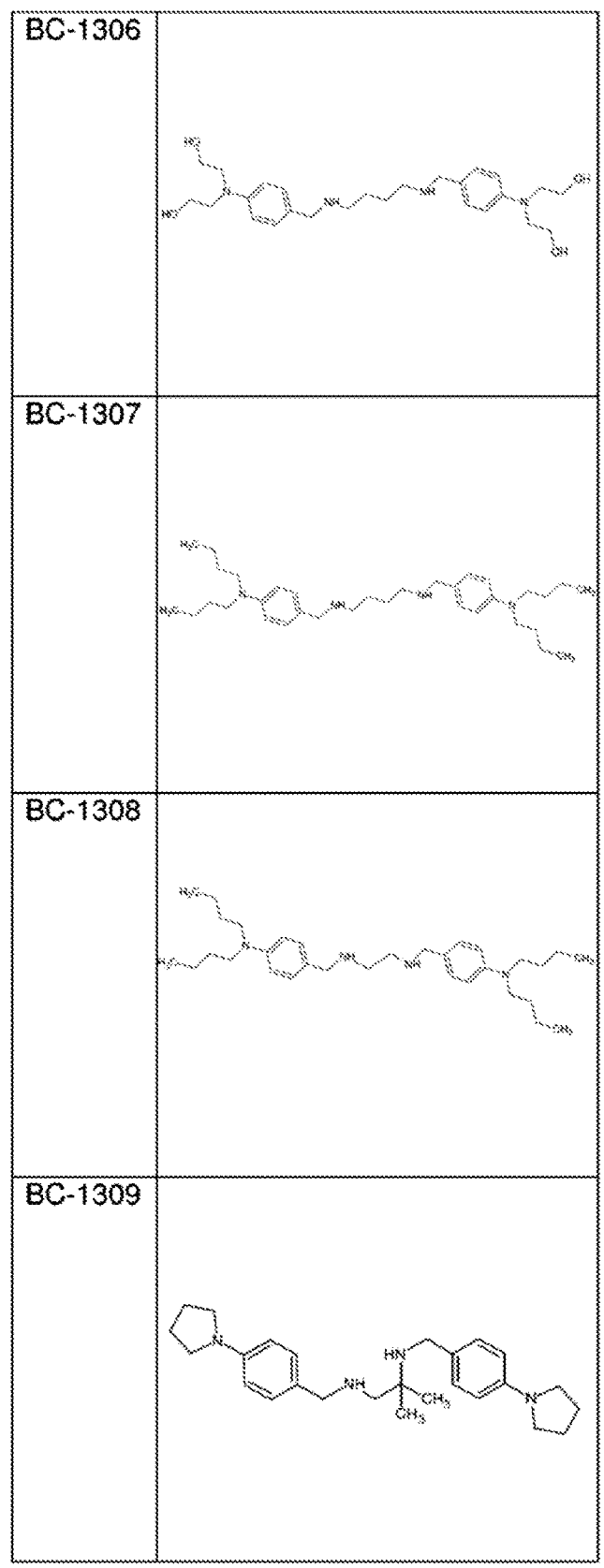
Figure 1C:
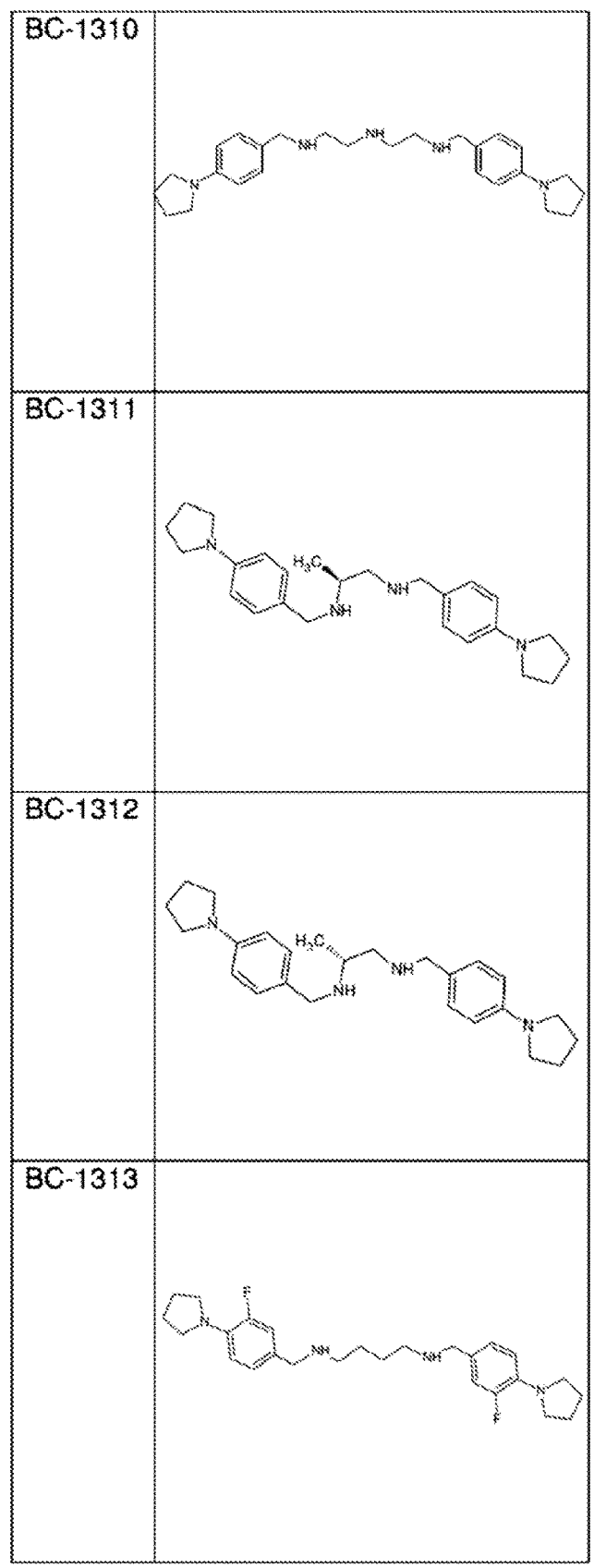
Figure 1D:
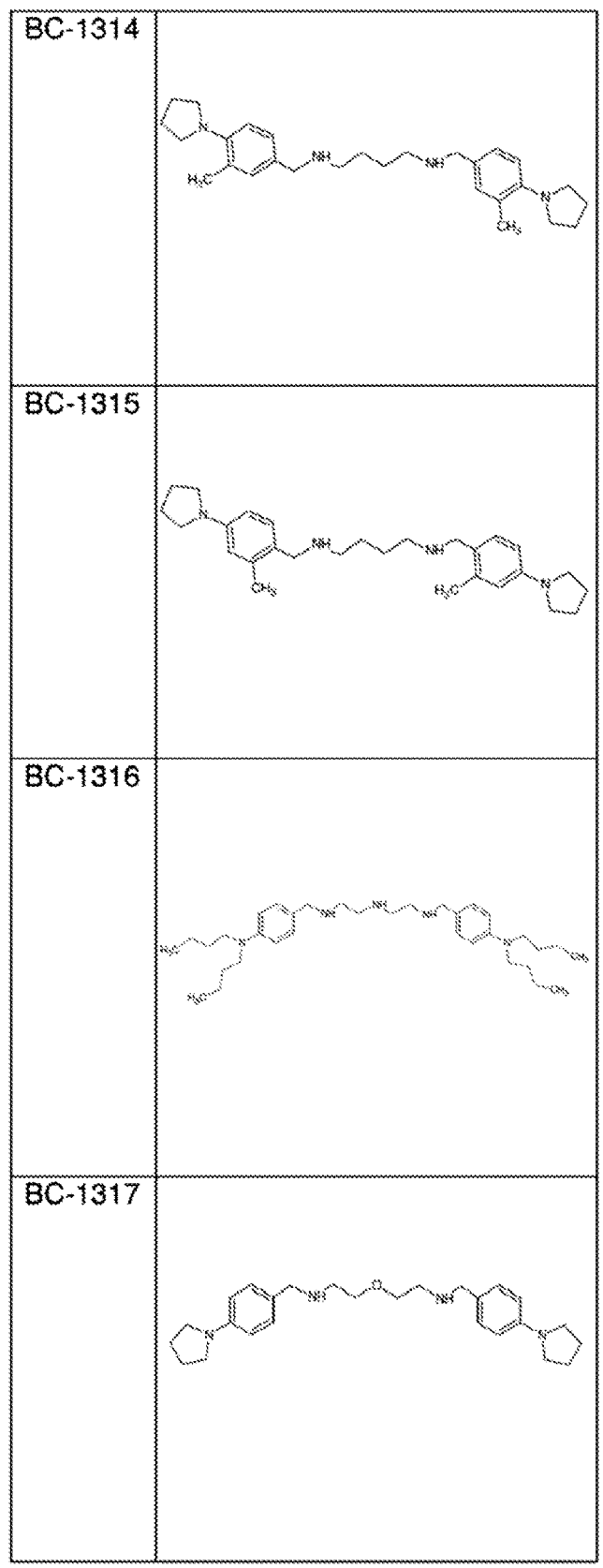
Figure 1E:
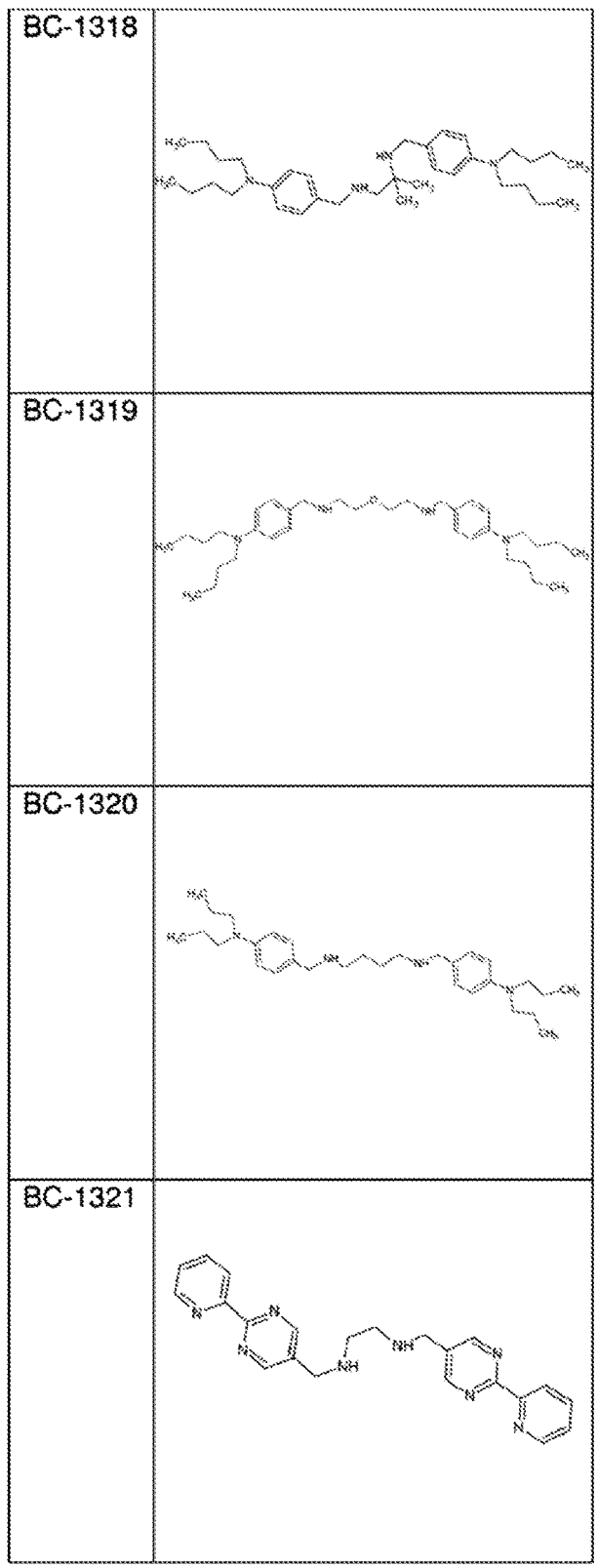
Figure 1F:
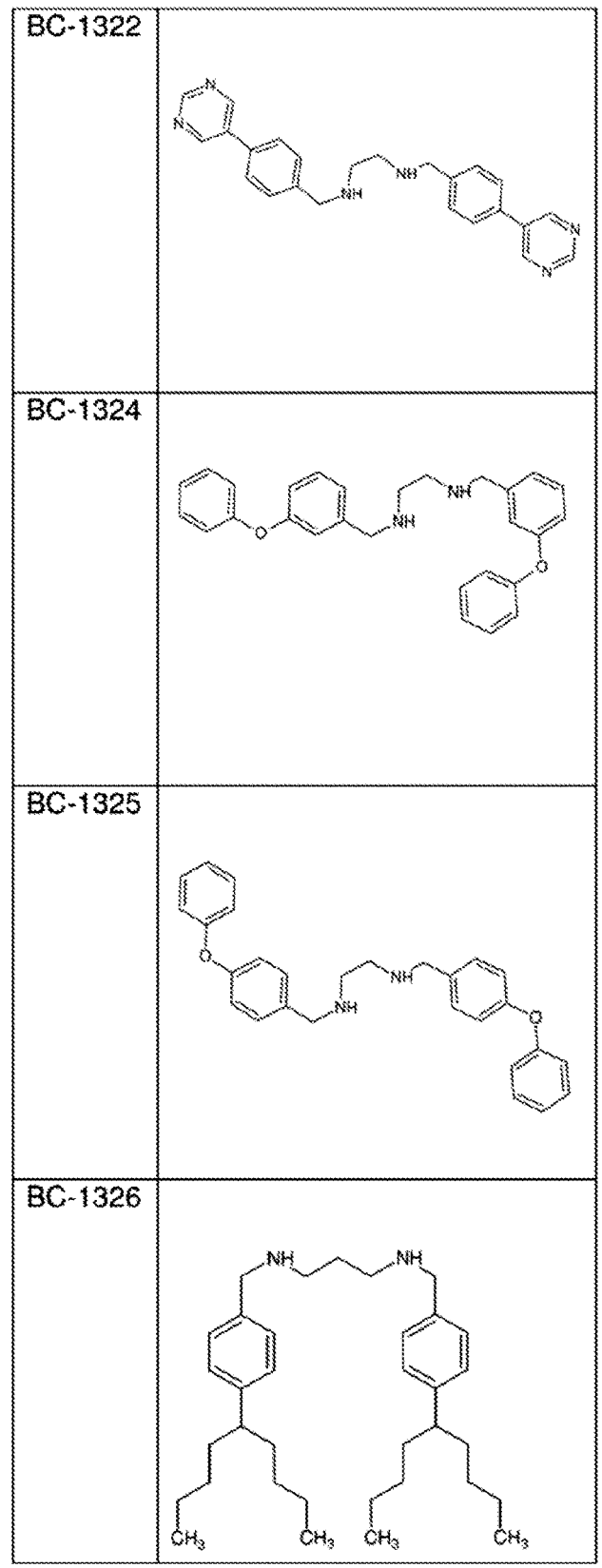
Figure 1G:
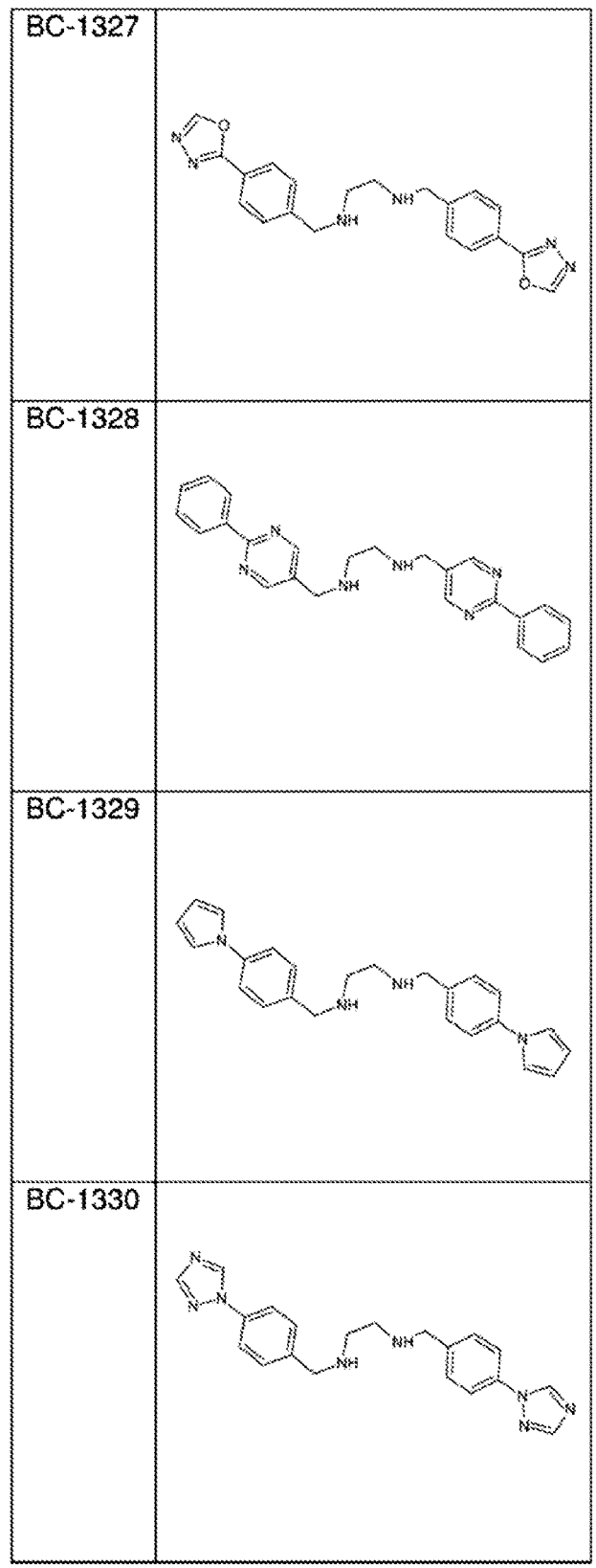
Figure 1H:
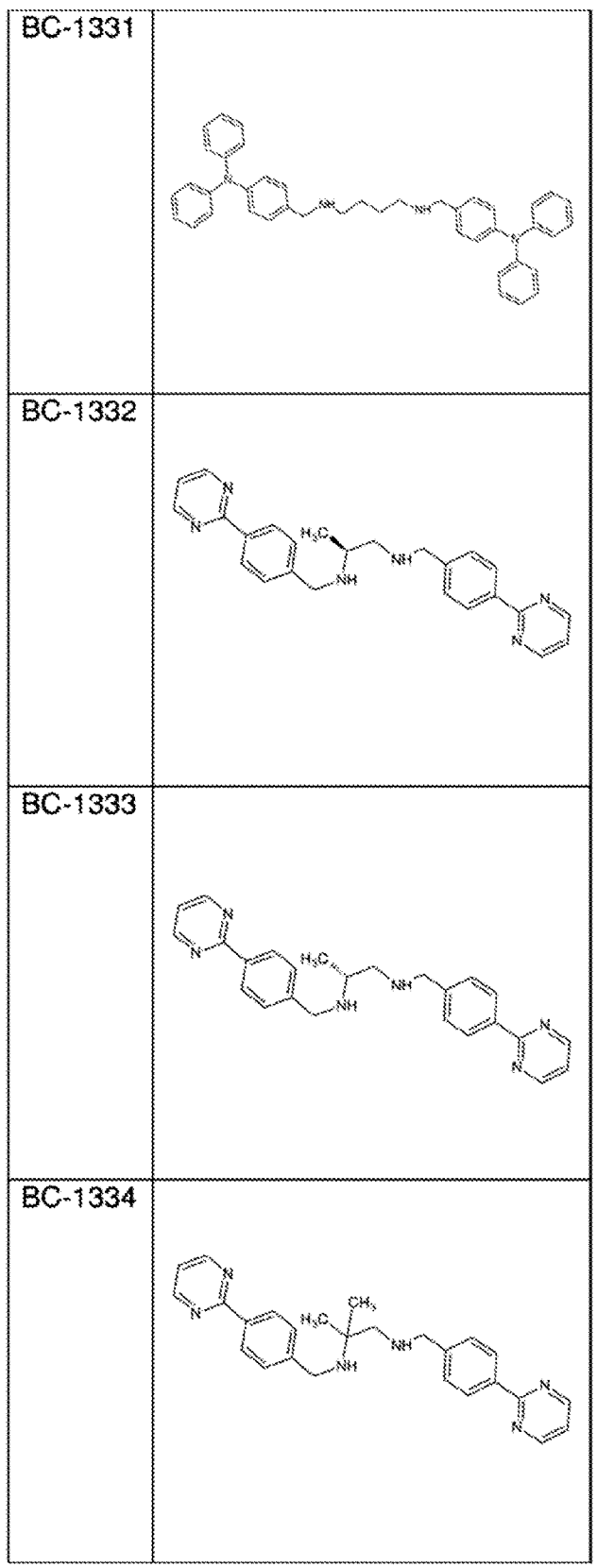
Figure 1I:
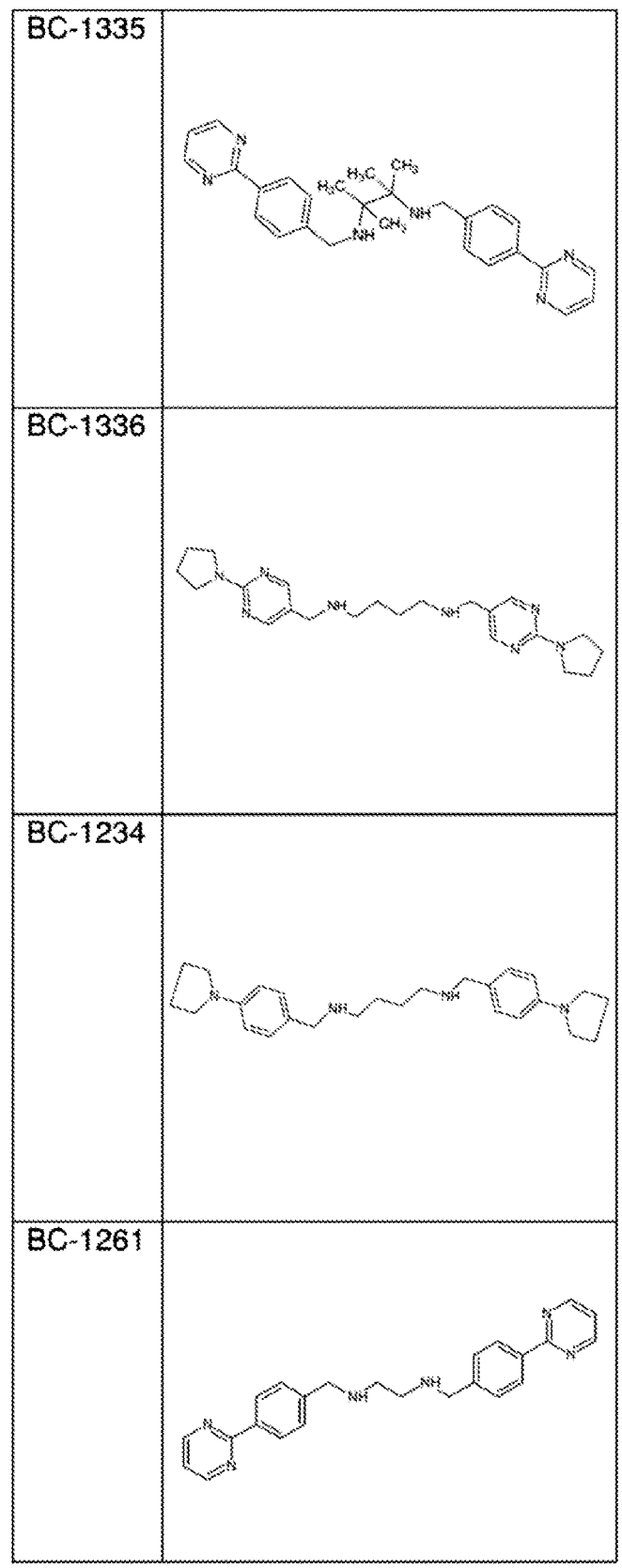
Figure 2B:
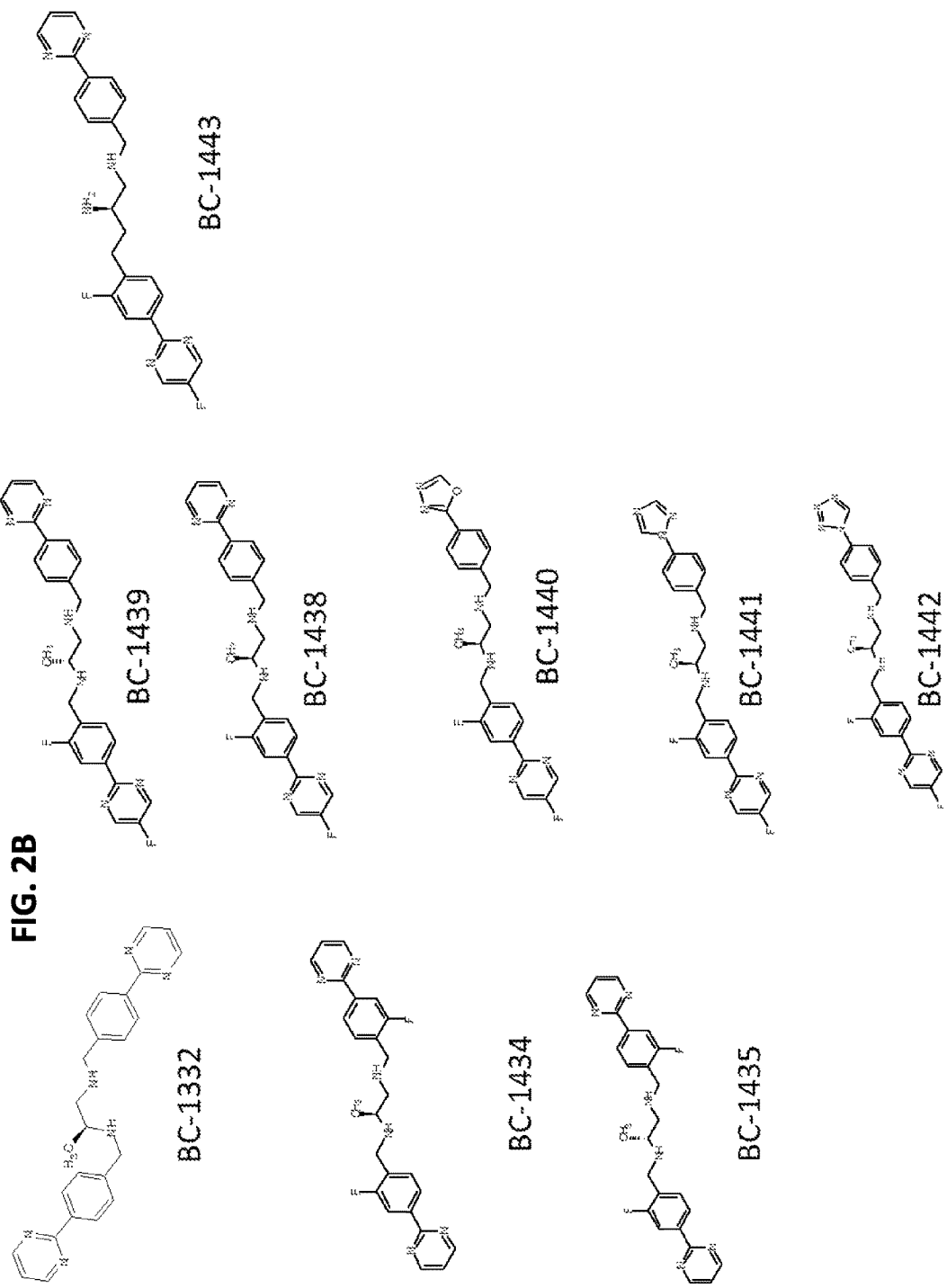
Figure 3:
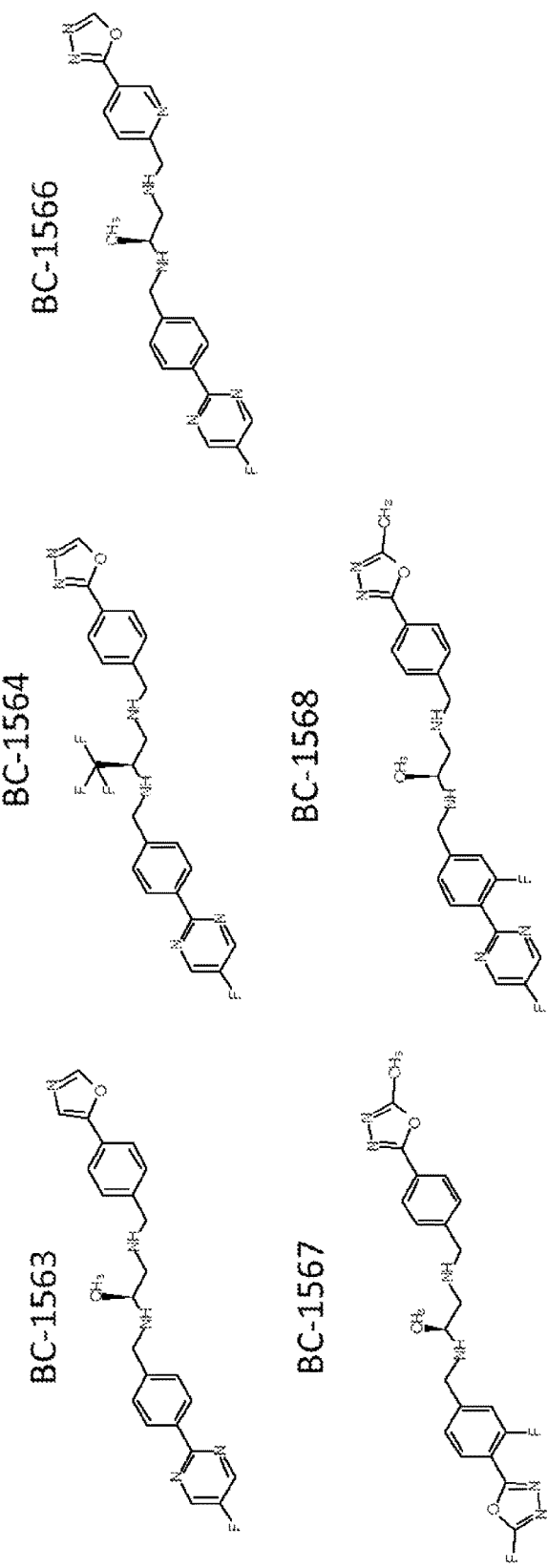
FIG. 3 shows further compounds presently disclosed herein.
Figure 4:
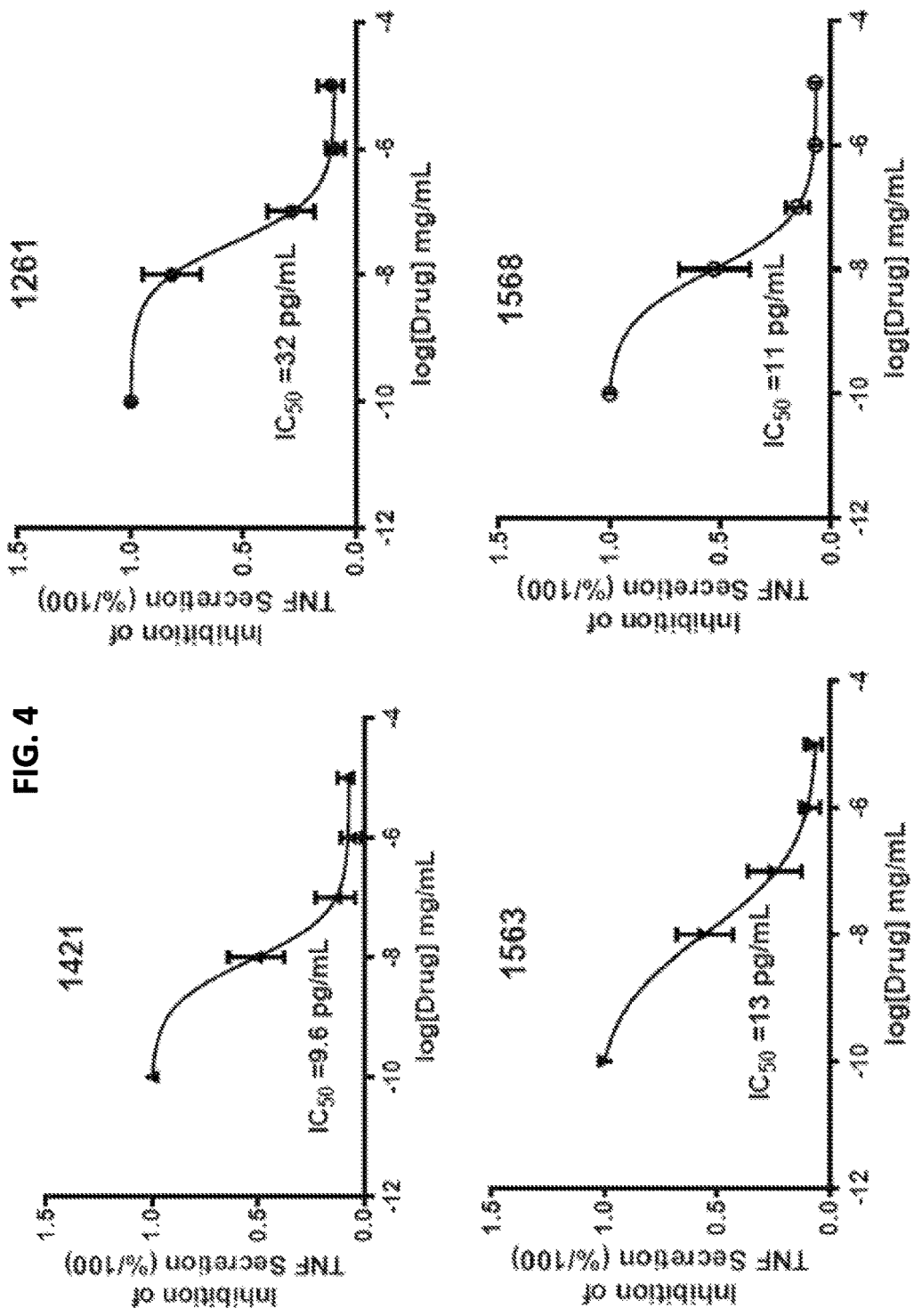

Examples of the compounds encompassed by the Formula II are provided in TABLE 2 and in FIGS. 2-3:

TABLE 2

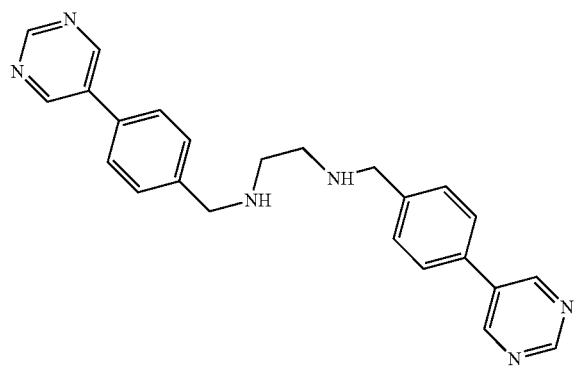 [SMILES: c1ncc(-c2ccc(CNCCNCc3ccc(-c4cncnc4)cc3)cc2)cn1]

201

TABLE 2-continued
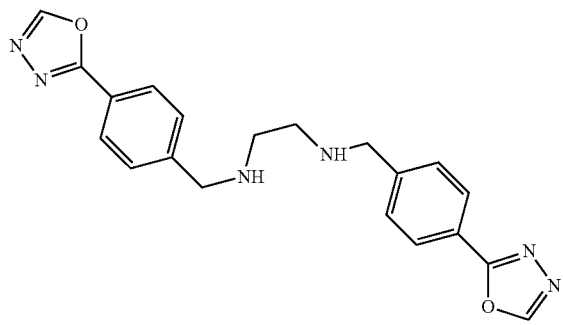 [SMILES: c1nnc(-c2ccc(CNCCNCc3ccc(-c4nnco4)cc3)cc2)o1]
202
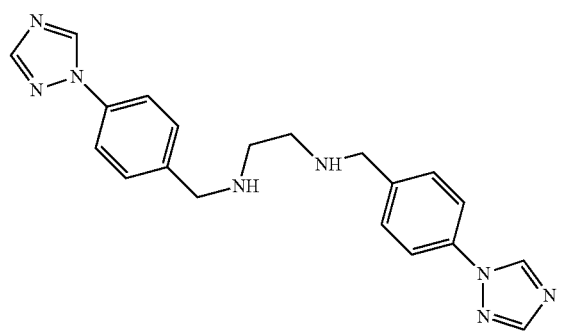 [SMILES: c1ncn(-c2ccc(CNCCNCc3ccc(-n4cncn4)cc3)cc2)n1]
203
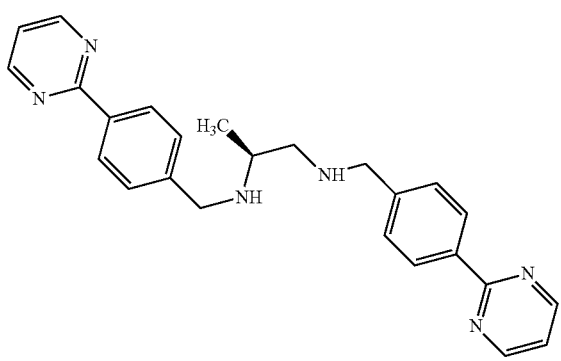 [SMILES: C[C@@H](CNCc1ccc(-c2ncccn2)cc1)NCc1ccc(-c2ncccn2)cc1]
204
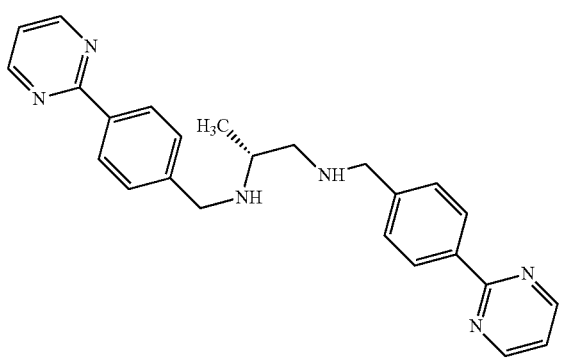 [SMILES: C[C@H](CNCc1ccc(-c2ncccn2)cc1)NCc1ccc(-c2ncccn2)cc1]
205

TABLE 2-continued
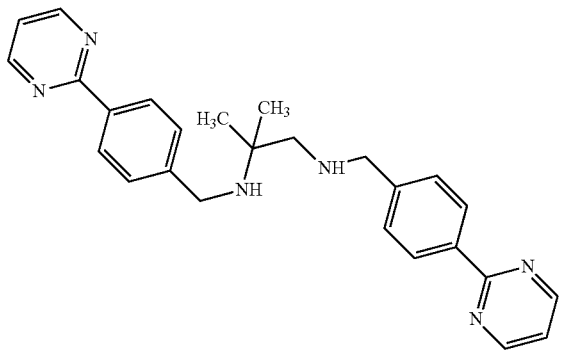 [SMILES: CC(C)(CNCc1ccc(-c2ncccn2)cc1)NCc1ccc(-c2ncccn2)cc1]
206
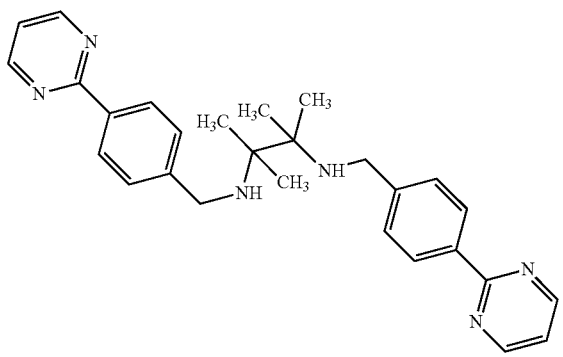 [SMILES: CC(C)(NCc1ccc(-c2ncccn2)cc1)C(C)(C)NCc1ccc(-c2ncccn2)cc1]
207
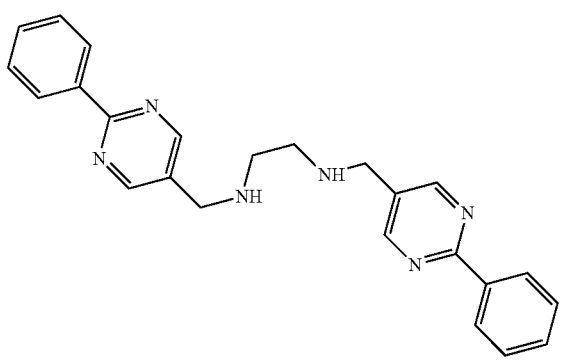 [SMILES: c1ccc(-c2ncc(CNCCNCc3cnc(-c4ccccc4)nc3)cn2)cc1]
208
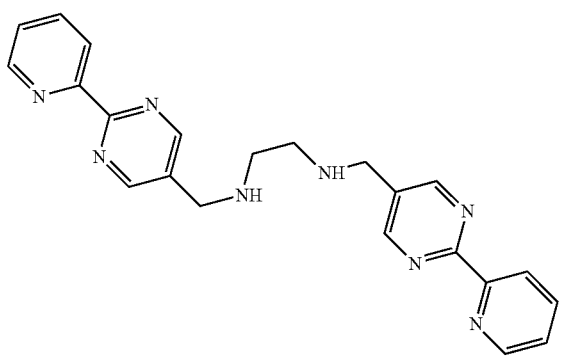 [SMILES: c1ccc(-c2ncc(CNCCNCc3cnc(-c4ccccn4)nc3)cn2)nc1]
209

TABLE 2-continued

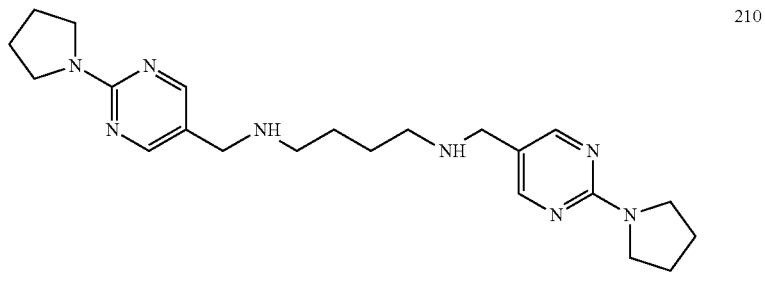
210

Still other embodiments are directed to compounds of Formula III, or a salt, ester, solvate, hydrate or prodrug thereof:

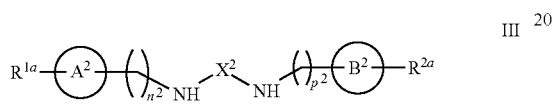
III where:
$X^2$ is a branched or unbranched $C_{1-10}$ alkyl, $(CH_2)_s$—NH—$(CH_2)_t$, $(CH_2)_s$—O—$(CH_2)_t$, or $(CH_2)_s$—$C(NH_2)$—$(CH_2)_v$—NH—$(CH_2)_t$, where s, t and v are each, independently an integer from 1 to 5;
$A^2$ and $B^2$ are each, independently, $C_{6-10}$aryl, $C_{6-10}$aryl-$C_{1-6}$alkyl, $C_{3-9}$ heteroaryl, or $C_{3-9}$heteroaryl-$C_{1-6}$alkyl, each optionally substituted with 1, 2 or 3 independently selected $R^g$ groups;
$R^{1a}$ and $R^{2a}$ are each, independently, $C_{1-10}$ alkyl, $C_{1-10}$ alkenyl, $C_{1-10}$ alkynyl, $C_{3-7}$ cycloalkyl, $C_{3-7}$ cycloalkyl-$C_{1-6}$alkyl, $C_{3-7}$ heterocycloalkyl, or $C_{3-7}$ heterocycloalkyl-$C_{1-6}$ alkyl, each of which can be optionally substituted with 1, 2 or 3 independently selected $R^g$ groups;
each $R^g$ is, independently, halogen, $C_{1-6}$ alkyl, $C_{1-6}$ haloalkyl, hydroxyl, $C_{1-6}$ alkoxy, $C_{1-6}$ haloalkoxy, amino, $C_{1-6}$alkylamino, or di-$C_{1-6}$alkylamino; and
$n^2$ and $p^2$ are each, independently, integers from 1 to 10.

In various embodiments, $A^2$ and $B^2$ may each, independently, be a 6-membered heteroaryl that can be substituted with one or more Rg groups such as those described above. For Example, $A^2$ and $B^2$ may be any pyridine or pyrimidine with heteroatoms in any configuration.

Each of $R^{1a}$ and $R^{2a}$ can be substituted at any position on $A^2$ and $B^2$, respectively. For example, $R^{1a}$ and $R^{2a}$ can be positioned in the ortho (o), meta (m), or para (p) position on $A^2$ and $B^2$ relative to the diamine connector portion of the molecule. In certain embodiments, each of $R^{1a}$ and $R^{2a}$ may be in para position.

In some embodiments, $R^{1a}$, $R^{2a}$, or both $R^{1a}$ and $R^{2a}$ are 6-membered cycloalkyl, 6-membered heterocycloalkyl, 5-membered cycloalkyl, or 5-membered heterocycloalkyl. In certain embodiments, these cycloalkyl and heterocycloalkyl can be saturated, i.e., unsubstituted, and in other embodiments, each of $R^1$ and $R^2$ may be substituted with one or more $R^g$ groups. When $R^{1a}$ or $R^{2a}$ are heterocycloalkyl the heteroatom may be positioned anywhere on the cyclic ring, and in some embodiments, the heteroatom may form a bond to the phenyl on the base structure. For example, the nitrogen of a pyrrolidine may bond to a carbon of the phenyl ring of the based structure as well as bonding to the 2 position and 5 position carbons of the pyrrolidine ring. Such heteroatoms that form a bond to the phenyl of the base structure will be referred to herein as a "linker heteroatom." Examples, of linker heteroatom containing $R^1$ and $R^2$ groups include, but are not limited to:

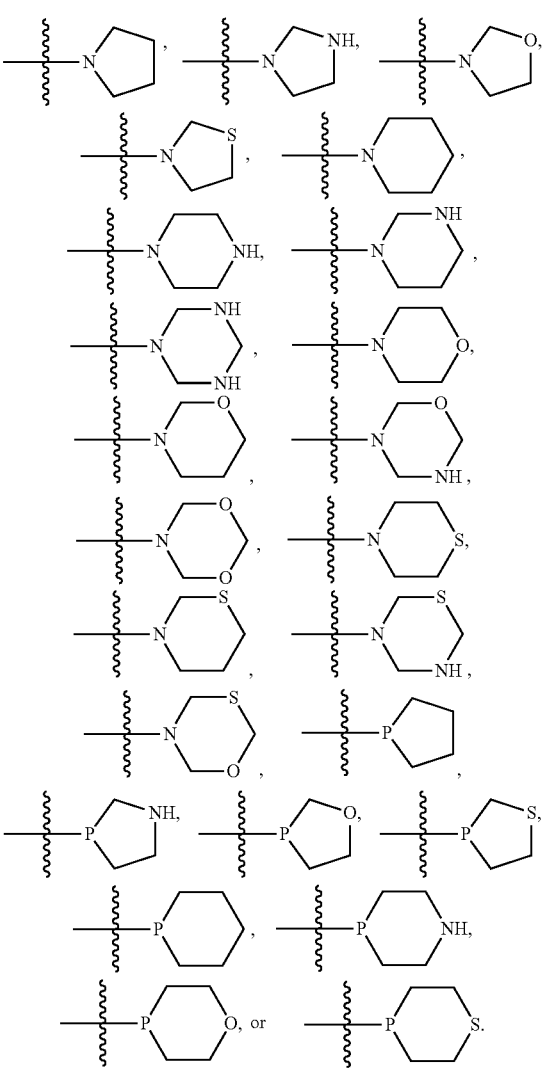

In particular embodiments, each of $R^{1a}$ and Rea may be pyrrolidine or piperidine, and in certain embodiments, both $R^{1a}$ and Rea may be either pyrrolidine or piperidine.

In some embodiments, $R^{1a}$, $R^{2a}$, or both $R^{1a}$ and $R^{2a}$ can be a tertiary amine. For example, in particular embodiments, $R^{1a}$, $R^{2a}$, or both $R^{1a}$ and $R^{2a}$ can be or general structure —$NR^{3a}R^{4a}$ where each of $R^{3a}$ and $R^{4a}$ can each, independently, be a $C_{1-10}$ alkyl, $C_{1-10}$ alkenyl, $C_{1-10}$ alkynyl $C_{3-10}$ aryl, $C_{3-10}$ aryl-$C_{1-6}$alkyl, $C_{3-10}$ heteroaryl, $C_{3-10}$ heteroaryl-$C_{1-6}$alkyl, $C_{3-7}$ cycloalkyl, $C_{3-7}$ cycloalkyl-$C_{1-6}$alkyl, $C_{3-7}$ heterocycloalkyl, or $C_{3-7}$ heterocycloalkyl-$C_{1-6}$ alkyl each of which can be unsubstituted or substituted with one or more halogen, $C_{1-6}$ alkyl, $C_{1-6}$haloalkyl, hydroxyl, $C_{1-6}$ alkoxy, $C_{1-6}$ haloalkoxy, amino, $C_{1-6}$ olkylamino, or di-$C_{1-6}$ olkylamino In certain embodiments, $R^{3a}$ and $R^{4a}$ can each, independently, be an unsubstituted $C_{1-10}$ alkyl, $C_{2-6}$ alkyl, or a $C_4$ alkyl, and in some embodiments, $R^{3a}$ and $R^{4a}$ can each, independently, be an unsubstituted $C_{6-8}$ aryl, or $C_{6-8}$ heteroaryl.

In certain embodiments, $R^{1a}$, $R^{2a}$, or both $R^{1a}$ and $R^{2a}$ can be a secondary amine having a branched or unbranched $C_{1-10}$ alkyl, $C_{1-10}$ alkenyl, $C_{1-10}$ alkynyl that can be unsubstituted or substituted with one or more halogen, $C_{1-6}$ alkyl, $C_{1-6}$haloalkyl, hydroxyl, $C_{1-6}$ alkoxy, $C_{1-6}$ haloalkoxy, amino, $C_{1-6}$alkylamino, or di-$C_{1-6}$alkylamino. In particular embodiments, $R^{3a}$ and $R^{4a}$ may be, for example, 3-aminononane, 4-aminononane, 5-aminononane, 3-aminooctane, 4-aminooctane, 2-aminoheptane, 3-aminoheptane, 4-aminoheptane, 2-aminohexane, 3-aminohexane, 2-aminopentane, 3-aminopentane, and the like and substituted versions thereof.

In some embodiments, $R^{1a}$, $R^{2a}$, or both $R^{1a}$ and $R^{2a}$ can be a branched $C_{1-10}$ alkyl, $C_{1-10}$ alkenyl, $C_{1-10}$ alkynyl that can be unsubstituted or substituted with one or more halogen, $C_{1-6}$ alkyl, $C_{1-6}$ haloalkyl, hydroxyl, $C_{1-6}$ alkoxy, $C_{1-6}$haloalkoxy, amino, $C_{1-6}$alkylamino, or di-$C_{1-6}$alkylamino In certain embodiments, $R^{1a}$, $R^{2a}$, or both $R^{1a}$ and $R^{2a}$ can be a branched $C_{1-10}$ alkyl. For example, in particular embodiments, each $R^{1a}$, $R^{2a}$, or both $R^{1a}$ and $R^{2a}$ can be 2-nonane, 4-nonane, 5-nonane, 3-octane, 4-octane, 2-heptane, 3-heptane, 4-heptane, 2-hexane, 3-hexane, 2-pentane, 3-aminopentane, and the like and substituted versions thereof.

Various embodiments include any combination of different $R^{1a}$ and $R^{2a}$ described above. For example, in some embodiments, $R^{1a}$ can be a cycloalkyl or heterocycloalkyl, and $R^{2a}$ can be a tertiary amine, secondary amine, or branched $C_{1-10}$ alkyl. In other embodiments, $R^{1a}$ can be a tertiary amine or secondary amine, and $R^{2a}$ can be a branched $C_{1-10}$ alkyl. Embodiments of the invention embrace all combinations of $R^{1a}$ and $R^{2a}$ described above.

In certain embodiments, $X^2$ may —$(CH_2)_s$—NH—$(CH_2)_t$— or —$(CH_2)_s$—O—$(CH_2)_t$—, where s and t are each, independently an integer from 1 to 3, and in particular embodiments, s and t may be 1 or 2. Thus, in some embodiments, $X^2$ may be —$CH_2$—NH—$CH_2$— or —$CH_2$—O—$CH_2$—.

Where $X^2$ is $C_{1-10}$ alkyl, the $C_{1-10}$ alkyl may be branched or unbranched, and in certain embodiments, the $C_{1-10}$ alkyl may be branched. While the size and character of the branches may vary among embodiments, in certain embodiments, each branch point may include be a methyl, ethyl, propyl, or butyl. Such branches may occur at one or more places on the alkyl chain linking the amines of the diamine linker. For example, a $C_3$-alkyl, $C_4$-alkyl, or a $C_5$-alkyl chain connecting the amines may include two separate methyl, ethyl, or propyl branches on adjacent or non-adjacent carbons, and in other embodiments, two methyl, ethyl, or propyl branches may extend from a single carbon on a $C_3$-alkyl, $C_4$-alkyl, or a $C_5$-alkyl chain connecting the amines. Examples of $X^2$ encompassed by the definition above include, but are not limited to, —$CH(CH_3)CH_2$—, —$CH(CH_3)CH(CH_3)$—, —$CH_2C(CH_3)(CH_3)CH_2$—, —$C(CH_3)(CH_3)$—, —$CH_2C(CH_3)(CH_3)$—, and the like. Thus, in various embodiments, X may be $C_{1-8}$ alkyl, $C_{1-6}$ alkyl, $C_{1-5}$ alkyl, or $C_{1-6}$ alkyl.

In various embodiments, $n^2$ and $p^2$ may be the same or different. For example, in some embodiments, $n^2$ and $p^2$ may, independently be integers from 1 to 8, 1 to 6, or 2 to 10. In particular embodiment, $n^2$ and $p^2$ may be the same and may be 1 to 3, and in certain embodiments, $n^2$ and $p^2$ may be 1.

In some embodiments, the compounds described above may be in free base or salt form. The terms "pharmaceutically acceptable salt" refers to salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in Handbook of Pharmaceutical Salts, Properties, Selection and Use, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like. Particular examples of amine bases (and their corresponding ammonium ions) for use in the present compounds include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl) amine, 2-hydroxy-tert-butylamine, tris(hydroxymethyl) methylamine, N,N-dimethyl-N-(2-hydroxyethyl)amine, tri-(2-hydroxyethyl)amine and N-methyl-D-glucamine For additional examples of "pharmacologically acceptable salts," see Berge et al., *J. Pharm. Sci.* 66:1 (1977).

In other embodiments, the compounds described above may be in ester form. "Pharmaceutically acceptable esters" includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include C1-C22 fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or aralkylsulphonyl (for example, methanesulphonyl); or amino acid esters (for example, L-valyl or L-isoleucyl).

Still other embodiments include prodrugs of the compounds described above. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. For a general discussion of prodrugs involving esters, see Svensson and Tunek, Drug Metabolism Reviews 165 (1988).

A prodrug form of a compound may be administered in an inactive form or a form having reduced activity that is transformed into an active or more active form of the drug by an enzymatic or chemical process. For example, in some embodiments, a prodrug form of a compound such as those described above may include one or more metabolically cleavable groups that can be removed by solvolysis, hydrolysis, or physiological metabolisms to release the pharmaceutically active form of the compound. In other embodiments, prodrugs may include acid derivatives of the compounds of the invention. Acid derivatives are well known in the art and include, but are not limited to, esters or double esters such as, for example, (acyloxy) alkyl esters or ((alkoxycarbonyl)oxy)alkyl esters prepared by reaction of an acid on the parent molecule with a suitable alcohol. Without wishing to be bound by theory, the compounds of the invention may have activity in both their acid and acid derivative forms. However, the acid derivative form may exhibit enhanced solubility, tissue compatibility or delayed release in the mammalian organism (see, e.g., Bundgard, H., Design of Prodrugs, pp. 7-9, 21-24, Elsevier, Amsterdam 1985). In other embodiments, prodrugs may include an amide and can be prepared by reacting a parent compound containing an acid with an amine, and in yet other embodiments, simple aliphatic or aromatic esters derived from acidic groups pendent on a compound of this invention may be prepared as prodrugs.

Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Yet other embodiments include solvates or hydrates of the described above. In some cases, hydration of a compound may occur during manufacture of the compounds or compositions including the compounds as a consequence of the method for preparing the compound or as a result of a specific step used to create a hydrate or solvate of the compound. In other cases, hydration may occur over time due to the hygroscopic nature of the compounds. Such hydrated compounds whether intentionally prepared or naturally produced are encompassed by the invention.

Further embodiments are directed to pharmaceutical compositions including one or more of the compounds described above or pharmaceutically acceptable salts, pharmaceutically acceptable esters of the compounds described above or solvates, hydrates or prodrugs of any of the compounds described above. In some embodiments, such compounds may be administered neat and, therefore, the pharmaceutical composition may only include one or more of the compounds described above or salts, esters, solvates, hydrates, or prodrugs thereof. In other embodiments, the compounds, salts, esters, solvates, hydrates, or prodrugs thereof may be combined with at least one pharmaceutically acceptable carriers, excipient, or diluent. Examples of carriers are well known to those skilled in the art and can be prepared in accordance with acceptable pharmaceutical procedures, such as, for example, those described in *Remington's Pharmaceutical Sciences*, 17th edition, ed. Alfonoso R. Gennaro, Mack Publishing Company, Easton, Pa. (1985), the entire disclosure of which is incorporated by reference herein for all purposes. The term "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

In some embodiments, pharmaceutical compositions may include one or more compound or salt, ester, solvate, hydrate, or prodrug thereof and a solid carriers for oral or parenteral administration. In certain embodiments, such pharmaceutical compositions may further include one or more additional components such as flavoring agents, lubricants, solubilizers, suspending agents, fillers, glidants, compression aids, binders or tablet-disintegrating agents, or various encapsulating materials. Oral formulations may be in any conventionally used oral form, including tablets, capsules, buccal forms, troches, lozenges, oral liquids, suspensions, or solutions. In powders, the carrier can be a finely divided solid, which is an admixture with a finely divided compound or salt, ester, solvate, hydrate, or prodrug thereof. In tablets, the compound or salt, ester, solvate, hydrate, or prodrug thereof can be mixed with a carrier having the appropriate compression properties and compacted in the shape and size desired. In various embodiments, the powders and tablets can contain up to 99 wt. % of the compound or salt, ester, solvate, hydrate, or prodrug thereof, and in some embodiments, the powder or tablet may include from about 10 wt. % to about 100 wt. %, about 15 wt. % to about 95 wt. %, about 20 wt. % to about 90 wt. %, about 25 wt. % to about 85 wt. %, or about 30 wt. % to about 75 wt. % compound or salt, ester, solvate, hydrate, or prodrug thereof or any individual concentration or range encompassed by these example ranges.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine Oral formulations herein can utilize standard delay or time-release formulations to alter the absorption of the compound. The oral formulation can also consist of administering a compound disclosed herein in water or fruit juice, containing appropriate solubilizers or emulsifiers as needed.

Capsules can contain mixtures of one or more compound or salt, ester, solvate, hydrate, or prodrug thereof and one or more inert fillers, diluents, or combinations thereof such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Liquid carriers can be used in preparing solutions, suspensions, emulsions, syrups, elixirs, and for inhaled delivery. Any of the compounds or salts, esters, solvates, hydrates, or prodrugs thereof described above can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). Liquid pharmaceutical compositions, which are sterile solutions or suspensions, can be utilized by, for example, intravenous, intramuscular, intraperitoneal or subcutaneous injection. For parenteral administration, the carrier can be an oily ester such as ethyl oleate and isopropyl myristate. Compositions for oral administration can be in either liquid or solid form. The liquid carrier for pressurized compositions can be halogenated hydrocarbon or other pharmaceutically acceptable propellants.

In some embodiments, the compound or salt, ester, solvate, hydrate, or prodrug thereof can be encapsulates with lipid formulations or formulated as nanocapsules. Lipid formulations and nanocapsules can be prepared by methods known in the art.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils. These preparations typically contain a preservative to inhibit the growth of microorganisms.

The pharmaceutical compositions of various embodiments can be prepared in unit dosage form such that each unit has one dose of the compound or salt, ester, solvate, hydrate, or prodrug thereof or a fraction of a dose of the compound or salt, ester, solvate, hydrate, or prodrug thereof, i.e., a sub-divided dose. For example, each tablets, capsules, powders, solutions, suspensions, emulsions, granules, or suppositories of the pharmaceutical composition may include a particular amount of the compound or salt, ester, solvate, hydrate, or prodrug thereof that provides a single dose or two or more units of the pharmaceutical composition can be combined to provide a single dose of the compound or salt, ester, solvate, hydrate, or prodrug thereof. Unit dosage forms can be packaged in, for example, powder packets, vials, ampoules, prefilled syringes, or sachets containing liquids. Alternatively, the unit dosage form can be a capsule or tablet itself. In various embodiments, each unit dose can contain from about 0.5 mg to about 500 mg of compound or salt, ester, solvate, hydrate, or prodrug thereof. In particular embodiments, each unit dose may include from about 0.75 mg to about 400 mg, about 1 mg to about 300 mg, about 2 mg to about 250 mg, about 5 mg to about 200 mg, about 10 to about 150 mg, or about 20 to about 100 mg of compound or salt, ester, solvate, hydrate, or prodrug thereof or any individual amount or range encompassed by these example ranges. The amount of compound or salt, ester, solvate, hydrate, or prodrug thereof in each unit dose can be selected to allow for variability in administration, for example, a patient may be instructed to take, 1 or 2 or 3 or 4 or more unit doses of the compound or salt, ester, solvate, hydrate, or prodrug thereof per day to achieve an effective amount, and the amount in each unit dose may allow for ease of ingestion, for example, a single tablet having a large amount of the compound or salt, ester, solvate, hydrate, or prodrug thereof may be more difficult to swallow than two or more smaller unit doses.

In particular embodiments, the compounds or salts, esters, solvates, hydrates, or prodrugs thereof can be combined with one or more additional therapeutic agents in a single pharmaceutical composition. Any therapeutic known in the art can be combined with the compounds or salts, esters, solvates, hydrates, or prodrugs thereof described above, and such additional therapeutics can be chosen to mitigate symptoms or otherwise aid in healing either independently or when combined with the compounds or salts, esters, solvates, hydrates, or prodrugs thereof described above. In particular embodiments, such agents may include, but are not limited to, another anti-inflammatory agent, an antimicrobial agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin, or an anti-vascular hyperproliferation compound, and the like and combinations thereof.

Additional embodiments are directed to methods for treating a patient with one or more of the compounds or salts, esters, solvates, hydrates, or prodrugs thereof described above. In general, such methods may include the step of administering the compound or salt, ester, solvate, hydrate, or prodrug thereof to a patient in need of treatment. In some embodiments, such methods may further include co-administering an additional therapeutic agent with the compounds or salts, esters, solvates, hydrates, or prodrugs thereof described above. Such additional agents include, but are not limited to, other anti-inflammatory agents, antimicrobial agents, matrix metalloprotease inhibitors, lipoxygenase inhibitors, cytokine antagonists, immunosuppressants, anti-cancer agents, anti-viral agents, cytokines, growth factors, immunomodulators, prostaglandins, anti-vascular hyperproliferation compounds, and the like and combinations thereof. In some embodiments, the compounds or salts, esters, solvates, hydrates, or prodrugs thereof described above and the additional agent may be combined such that administering can be carried out concurrently in, for example, a single oral dose or injection. In other embodiments, the compounds or salts, esters, solvates, hydrates, or prodrugs thereof described above and the additional agent may be administered in separate unit doses either concurrently or at different times throughout the course of treatment.

In some embodiments, the patient may be administered an effective amount of the compound or salt, ester, solvate, hydrate, or prodrug thereof to provide relief from inflammation.

In one embodiment the compounds or pharmaceutical compositions disclosed herein may be used for treating inflammatory disorders, particularly inflammatory disorders that are mediated by cytokine release, especially a cytokine storm. For example, the compounds or pharmaceutical compositions disclosed herein may be used for treating inflammatory disorders that underlie numerous human diseases characterized by a highly activated immune system that leads to secretion of large amounts of circulating pro-inflammatory cytokines after infection with virulent pathogens, in response to host cell injury, or related irritants that activate receptors on immune effector cells (T-cells, macrophages, etc.). A central feature of these infectious disorders is the burst in cytokine release, i.e. cytokine storm, from pro-inflammatory cells including macrophages, lymphocytes, and PMNs. Under many conditions, the cytokine storm is exaggerated (hypercytokinemia) and results in a fatal immune reaction with constant activation of immune effector cells that produce sustained and supraphysiologic levels of TNFα, IL-β, and IL-6 that leads to profound tissue injury. The compounds disclosed herein may inhibit the release of pro-inflammatory cytokines (e.g., TNFα, IL-β, and/or IL-6). In certain embodiments, the compounds disclosed herein are panreactive to numerous injurious cytokines. The compounds disclosed herein inhibit inflammation and prevent tissue damage (e.g., lung damage, particularly lung damage from bacterial infection) in a subject. For example, the compounds disclosed herein may inhibit hypercytokinemia, and/or may prevent or diminish supra-physiologic levels of TNFα, IL-β, and/or IL-6 or related injurious molecules.

Inflammatory disorders that may be treated by the compounds or pharmaceutical compositions disclosed herein include any disorder possessing an inflammatory component. Illustrative inflammatory disorders include acute and chronic inflammation disorders such as asthma, chronic obstructive lung disease, pulmonary fibrosis, pneumonitis (including hypersensitivity pneumonitis and radiation pneumonitis), pneumonia, cystic fibrosis, psoriasis, arthritis/rheumatoid arthritis, rhinitis, pharyngitis, cystitis, prostatitis, dermatitis, allergy including hayfever, nephritis, conjunctivitis, encephalitis, meningitis, opthalmitis, uveitis, pleuritis, pericarditis, myocarditis, atherosclerosis, human immunodeficiency virus related inflammation, diabetes, osteoarthritis, psoriatic arthritis, inflammatory bowel disease (Crohn's disease, ulcerative colitis)/colitis, sepsis, vasculitis, bursitis, connective tissue disease, autoimmune diseases such as systemic lupus erythematosis (SLE), polymyalgia rheumatica, scleroderma, Wegener's granulomatosis, temporal arteritis, vasculitis, cryoglobulinemia, and multiple sclerosis, viral or influenza-induced inflammation, or edema. The compounds or compositions disclosed herein may be particularly effective for treating sepsis, pneumonia, influenza-induced inflammation, edema, neuropathy, colitis, arthritis, Crohn's disease, diabetes, skin, eye and ear inflammation (e.g., psoriasis, uveitis/opthalmitis, external otitis), systemic lupus erythematosis (SLE), and systemic lupus erythematosis (SLE). The compounds disclosed herein may be useful for treating inflammation and tissue damage induced by pathogenic infection with, for example, *Pseudomonas aeruginosa, Staphylococcus aureus, Streptococcus pneumoniae, Haemophilus influenza*, or *Escherichia*

*coli*. The compounds disclosed herein may be especially effective for treating sepsis or pneumonia.

In certain embodiments the compounds or pharmaceutical compositions disclosed herein may be used for treating other FBXO3-mediated disorders or injuries such as, for example, malaria, toxic lung exposure, cancer, Alzheimer's, or a burn-related injury. Illustrative cancers include leukemia, lymphoma, bronchogenic carcinoma, adenocarcinoma of the breast, colon, ovary, thyroid, pancreas, stomach, and prostate, squamous cell cancer, small cell cancer, melanoma, sarcoma, and metastatic cancer. Since an FBXO3 inhibitor up-regulates FBXL2, other substrates of FBXL2 such as cyclin D2/3, Aurora B protein will be degraded upon FBXO3 inhibitor treatment. Since Cyclin D2/3 and Aurora B are well-described oncoproteins, thus FBXO3 inhibitor may inhibit cancer proliferation through inhibiting cyclins and Aurora B protein.

In certain embodiments, the compounds or pharmaceutical compositions disclosed herein can be administered to a patient in need of treatment for a respiratory injury or disease. The respiratory injury or disease may be, for example, acute or chronic bronchitis, emphysema, respiratory infections (pneumonia, pleurisy), flu (including influenza), post-lung transplant rejection including acute and chronic rejection and bronchiolitis obliterans, acute lung injury or the acute respiratory distress syndrome, pulmonary fibrosis, asthma, cystic fibrosis, or bronchiectasis.

In certain embodiments, the compounds or pharmaceutical compositions disclosed herein can be administered to a patient in need of treatment for myopathy, steroid-induced myopathy, muscular dystrophy, amyotrophic lateral sclerosis (ALS), muscle weakness, critical illness myopathy, muscle atrophy, muscle wasting, rhabdomyolysis, dermatomyositis, myositis, mitochondrial myopathy, chronic obstructive lung disease, organ transplant rejection, psoriasis, myasthenia gravis, Addison's disease, celiac disease, Graves' disease, Hashimoto's thyroiditis, or pernicious anemia.

In certain embodiments the compound(s) and composition(s) disclosed herein may be administered to a subject for muscle building in the subject (i.e., use as a muscle building supplement).

An effective dose can vary depending upon the particular compound, the mode of administration, and severity of the condition being treated. The dosage to be administered in the treatment of a specific individual typically must be subjectively determined by the attending physician who can base the recommended dosage on the size, health, age, and response pattern of the patient and presence of other conditions associated with the patient. Higher or lower concentrations can be selected based on the mode of delivery, for example, trans-epidermal, rectal, oral, pulmonary, intraosseous, or intranasal delivery versus intravenous or subcutaneous or intramuscular delivery. Dosage can also be adjusted based on the release rate of the administered formulation, for example, of an intrapulmonary spray versus powder, sustained release oral versus injected particulate or transdermal delivery formulations, and so forth. In therapeutic applications, any compound or salt, ester, solvate, hydrate, or prodrug thereof described above can be administered to a patient already suffering from a disease in an amount sufficient to at least partially ameliorate the symptoms of the disease.

In various embodiments, an effective dose can contain from about 0.5 mg to about 500 mg of compound or salt, ester, solvate, hydrate, or prodrug thereof. In particular embodiments, effective dose may include from about 0.75 mg to about 400 mg, about 1 mg to about 300 mg, about 2 mg to about 250 mg, about 5 mg to about 200 mg, about 10 to about 150 mg, or about 20 to about 100 mg of compound or salt, ester, solvate, hydrate, or prodrug thereof or any individual amount or range encompassed by these example ranges. In other embodiments, an effective amount may be determined based on the weight of the patient. For example, administering may include from about 0.5 mg/kg to about 500 mg/kg of the compounds described above or salts, esters, solvates, hydrates, or prodrugs thereof per kg of body weight, and in some embodiments, from about 0.75 mg/kg to about 400 mg/kg, about 1 mg/kg to about 300 mg/kg, about 2 mg/kg to about 250 mg/kg, about 5 mg/kg to about 200 mg/kg, about 10 mg/kg to about 150 mg/kg, or about 20 mg/kg to about 100 mg/kg may be administered to a patient. In still other embodiments, an effective amount may be based on the plasma concentration of the compound or salt, ester, solvate, hydrate, or prodrug thereof after administration. For example, in some embodiments, sufficient compound or salt, ester, solvate, hydrate, or prodrug thereof may be administered to produce a peak plasma concentration of from about 1μg/mL to about 250 μg/mL, and in other embodiments, a sufficient amount of a pharmaceutical composition may be administered to produce a peak plasma concentration of about 2 μg/mL to about 200 μg/mL, about 3 μg/mL to about 150 μg/mL, about 5 μg/mL to about 100 μg/mL, about 5 μg/mL to about 75 μg/mL, or any individual value or range encompassed by these example ranges.

In certain embodiments, the methods described above may include repeating the step of administering. For example, a patient may receive or be instructed to ingest or otherwise self-administer a pharmaceutical composition containing one or more of the compounds or salts, esters, solvates, hydrates, or prodrugs thereof described above once per day for a prescribed time period or two or more times per day for a prescribed period of time. Repeated administration can be carried out for any time period. For example, repeating one or more daily administration of the compounds or salts, esters, solvates, hydrates, or prodrugs thereof described above can be carried out for 3 days to about 1 year, 1 week to about 6 months, 2 weeks to about 3 months, or any time period encompassed by these example ranges.

Administering can be carried out in any manner, for example, administration can be carried out orally, via implants, parenterally (including intravenous, intraperitoneal and subcutaneous injections) either by bolus injection or infusion, rectally, vaginally, and transdermally, and so on, using any of the pharmaceutical compositions described above. In embodiments in which the compounds or salts, esters, solvates, hydrates, or prodrugs thereof described above are administered parenterally, solutions, dispersions, or suspensions can be prepared in water suitably mixed with a surfactant such as hydroxyl-propylcellulose. In some embodiments, such dispersions or suspensions can be prepared in glycerol, liquid polyethylene glycols, and mixtures thereof in oils.

In some cases, it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compound or salt, ester, solvate, hydrate, or prodrug thereof described above dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compound or salt, ester, solvate, hydrate, or prodrug thereof described above intermixed with lactose or other inert powders that are acceptable for intrabronchial use, and can be administered by, for example, an aerosol dispenser or a device that breaks or punctures a capsule encasing the solid composition and delivers the solid composition for inhalation, i. e. , blister packs. In some embodiments, inhaled compositions encompassed by the invention may include one or more additional inhaled therapeutic compounds. For example, in certain embodiments, the inhaled compositions may include compounds as disclosed herein, and one or more additional therapeutic compound such as, for example, bronchodilators such as β2 agonists (SABA/LABA) such as salmeterol, terbutaline, salbutamol, levosalbutamol, pirbuterol, bambuterol, fenoterol, metalproterenol, and formoterol, other bronchodilators such as epinephrine, racemic epinephrine, ephedrine, clenbuterol, indacaterol, vilanterol, and theophylline; corticosteroids such as beclomethasone, budesonide, ciclesonide, flunisolide, fluticasone and triamcinolone, anticholinergics such as ipratropium and tiotropium, anti-inflammatories such as cromolyn and nedocromil, and the like and various combinations thereof. The aerosol composition can include, by way of illustration, one or more compound or salt, ester, solvate, hydrate, or prodrug thereof described above, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

In certain embodiments, the compounds or compositions disclosed herein may be administered via intratracheal delivery, with or without co-administration of a bronchodilator such as β2 agonists (SABA/LABA) such as salmeterol, terbutaline, salbutamol, levosalbutamol, pirbuterol, bambuterol, fenoterol, metalproterenol, and formoterol, other bronchodilators such as epinephrine, racemic epinephrine, ephedrine, clenbuterol, indacaterol, vilanterol, and theophyllines; corticosteroids such as beclomethasone, budesonide, ciclesonide, flunisolide, fluticasone and triamcinolone, anticholinergics such as ipratropium and tiotropium, anti-inflammatories such as cromolyn and nedocromil, and the like and various combinations thereof.

Compounds described herein can be administered transdermally, i.e., administered across the surface of the body and the inner linings of bodily passages including epithelial and mucosal tissues. Administering transdermally can be carried out by applying any of the compounds or salts, esters, solvates, hydrates, or prodrugs thereof to a surface of the body in, for example, lotions, creams, foams, patches, suspensions, solutions, and suppositories (rectal and vaginal). In some embodiments, transdermal administration can be accomplished through the use of a transdermal patch containing a compound and a carrier that is inert to the compound, non-toxic to the skin, and combine with the compound to allow the compound to be absorbed into the blood stream for systemic delivery. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Additional embodiments are directed to methods for making the compounds or salts, esters, solvates, hydrates, or prodrugs thereof described above. Synthetic methods for the compounds described above may vary among embodiments and can encompass any number of steps, utilize various catalysts, solvents, purification procedures, and so on while falling within the scope of the invention. For example, as illustrated in Scheme I below in some embodiments, the compounds of the invention can be made by combining an aldehyde containing benzene with a alkylene diamine in a solvent such as anhydrous ethanol and heating this solution under reflux until the solvent has evaporated resulting in formation of a Schiff base. The Schiff base can then be isolated and washed before being dissolved in a second solvent such as absolute methanol to create a second solution to which a reducing agent such as sodium borohydride can be added which reduces the Schiff base to secondary amine The secondary amine containing compound can be isolated and washed or purified to produce the compounds of the invention.

Scheme I

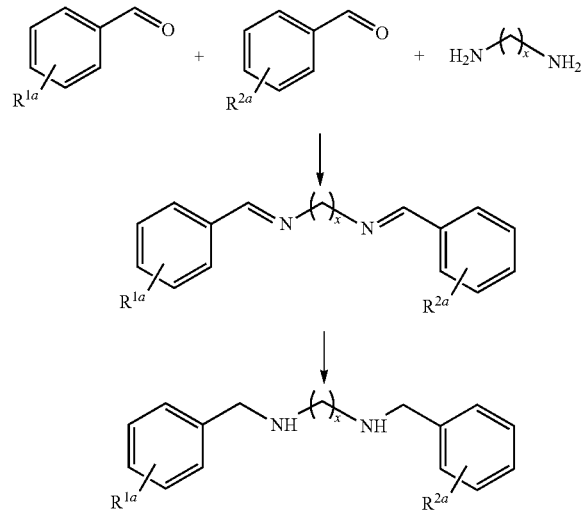

In Scheme I, each $R^{1a}$ and $R^{2a}$ may, independently, be a amine, $C_{1-10}$ alkyl, $C_{1-10}$ alkenyl, $C_{1-10}$ alkynyl, $C_{3-7}$ cycloalkyl, $C_{3-7}$ cycloalkyl-$C_{1-6}$alkyl, $C_{3-7}$ heterocycloalkyl, $C_{3-7}$ heterocycloalkyl-$C_{1-6}$ alkyl each of which may be substituted with one or more $R^g$ groups as described above with reference to $R^1$ and $R^2$ in Formulae I and Ia. In particular embodiments, $R^{1a}$ and $R^{2a}$ can be any of the 6-membered cycloalkyl, 6-membered heterocycloalkyl, 5-membered cycloalkyl, 5-membered heterocycloalkyl, tertiary amine, or secondary amine, described above, and in certain embodiments, $R^{1a}$ and $R^{2a}$ may be the same. As in Formulae I and Ia, X may be $C_{1-10}$ alkyl, $(CH_2)_s$—NH—$(CH_2)_t$, $(CH_2)_s$—O—$(CH_2)_t$, where s and t are each, independently an integer from 1 to 5. Additionally, while the benzaldehyde is represented as an aldehyde containing benzene in Scheme I, any aldehyde containing benzene can be used. For example, 2-phenylacetaldehyde, 3-phenylpropanal, 4-phenylbutanal, and the like compounds substituted with an $R^{1a}$ or $R^{2a}$ substituent can be used in various embodiments.

In particular embodiments, methods for making the compounds of the invention may further include the step of preparing a salt form of the compound prepared as described above. In such embodiments, the method may include dissolving an isolated form of the secondary amine in a solution and adding an ionizing compound to the solution. Various ionizing compounds are known in the art and include, but are not limited to, hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. For example, in certain embodiments, the secondary amine containing compound may be dissolved in water and concentrated hydrochloric acid or sodium acetate may be added to the solution until the salt form of the compound crystallizes out of the solution. Such method may further include the steps of isolating the crystalline compound, washing the crystals, and redissolving or compounding the crystals.

Methods for making pharmaceutical compositions may include the steps of dissolving the compounds produced as described above in sterile a solution, such as water, saline, Ringer's solution, or an appropriate oil. In other embodiments, methods for making pharmaceutical compositions may include combining or compounding solid, powdered, or crystalline forms of the compounds produced as described above with powdered carriers and excipients, and pressing the mixtures into tablets. In still other embodiments, methods for making pharmaceutical compositions may include the step of forming microparticles or nanoparticles including the compounds produced as described above and encapsulating these microparticles or nanoparticles in a capsule or tablet. In further embodiments, such methods may further include incorporating one or more additional components such as flavoring agents, lubricants, solubilizers, suspending agents, fillers, glidants, compression aids, binders or tablet-disintegrating agents, or various encapsulating materials as discussed above into the various pharmaceutical compositions, and in certain embodiments, such additional agents may be added before pressing the mixtures into tablets or forming or encapsulating microparticles or nanoparticles.

Certain embodiments are disclosed in the following numbered paragraphs:

1. A compound of general Formula I:

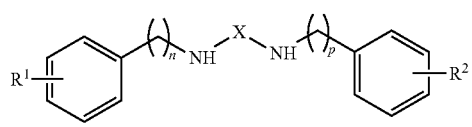

I or salt, ester, solvate, hydrate, or prodrug thereof;
wherein:
X is $C_{1-10}$ alkyl, $(CH_2)_s$—NH—$(CH_2)_t$, $(CH_2)_s$—O—$(CH_2)_t$, or $(CH_2)_s$—C($NH_2$) $(CH_2)_v$—NH—$(CH_2)_t$, wherein s, t and v are each, independently, an integer from 1 to 5;
$R^1$ and $R^2$ are each, independently, amine, $C_{1-10}$ alkyl, $C_{1-10}$ alkenyl, $C_{1-10}$ alkynyl, $C_{3-7}$ cycloalkyl, $C_{3-7}$ cycloalkyl-$C_{1-6}$alkyl, $C_{3-7}$ heterocycloalkyl, or $C_{3-7}$ heterocycloalkyl-$C_{1-6}$ alkyl; and
n and p are each, independently, integers from 1 to 10.

2. The compound of paragraph 1, wherein $R^1$ and $R^2$ are the same.
3. The compound of paragraph 1, wherein $R^1$ and $R^2$ are in para configuration.
4. The compound of paragraph 1, wherein $R^1$ and $R^2$ are each, independently, selected from the group consisting of 6-membered cycloalkyl, 6-membered heterocycloalkyl, 5-membered cycloalkyl, and 5-membered heterocycloalkyl.
5. The compound of paragraph 1, wherein $R^1$ and $R^2$ are each, independently, substituted with at least one $R^g$ group selected from the group consisting of halogen, $C_{1-6}$ alkyl, $C_{1-6}$ haloalkyl, hydroxyl, $C_{1-6}$ alkoxy, $C_{1-6}$ haloalkoxy, amino, $C_{1-6}$alkylamino, and di-$C_{1-6}$alkylamino
6. The compound of paragraph 1, wherein $R^1$ and $R^2$ are each, independently, comprise a linker heteroatom.
7. The compound of paragraph 1, wherein $R^1$ and $R^2$ are each, independently, selected from the group consisting of:

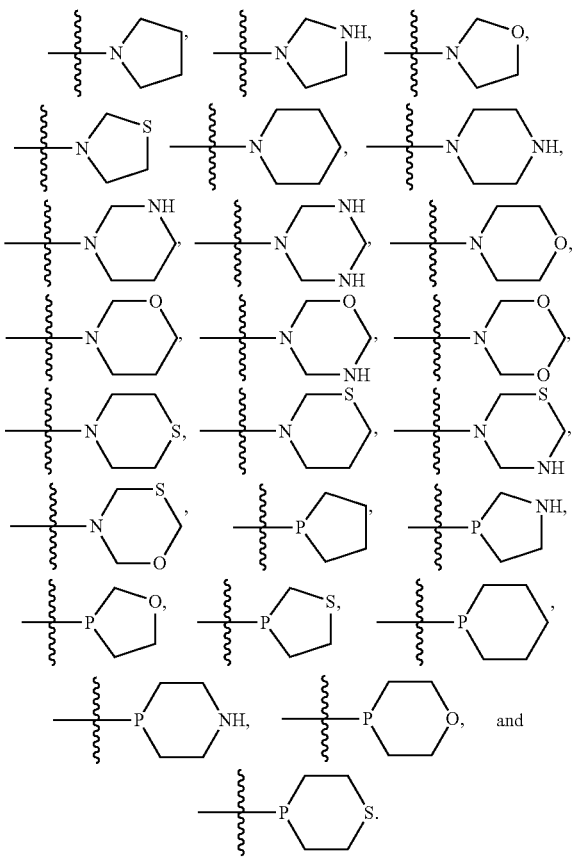

8. The compound of paragraph 1, wherein each $R^1$ and $R^2$ is, independently, selected from the group consisting of pyrrolidine and piperidine.

9. The compound of paragraph 1, wherein each $R^1$ and $R^2$ is, independently, a tertiary amine 10. The compound of paragraph 1, wherein each $R^1$ and $R^2$ is, independently, of formula —$NR^3R^4$ wherein each $R^3$ and $R^4$ is, independently, selected from the group consisting of $C_{1-10}$ alkyl, $C_{1-10}$ alkenyl, and $C_{1-10}$ alkynyl.

11. The compound of paragraph 10, wherein R3 and R4 are, independently substituted with at least one substituent selected from the group consisting of halogen, $C_{1-6}$ alkyl, $C_{1-6}$ haloalkyl, hydroxyl, $C_{1-6}$ alkoxy, $C_{1-6}$ haloalkoxy, amino, $C_{1-6}$alkylamino, and di-$C_{1-6}$alkylamino 12. The compound of paragraph 1, wherein each $R^1$ and $R^2$ is, independently, a secondary amine.

13. The compound of paragraph 12, wherein the secondary amine comprises a branched $C_{1-10}$ alkyl, $C_{1-10}$ alkenyl, or $C_{1-10}$ alkynyl.

14. The compound of paragraph 13, wherein the branched $C_{1-10}$ alkyl, $C_{1-10}$ alkenyl, and $C_{1-10}$ alkynyl is substituted with at least one substituent selected from the group consisting of halogen, $C_{1-6}$ alkyl, $C_{1-6}$ haloalkyl, hydroxyl, $C_{1-6}$ alkoxy, $C_{1-6}$ haloalkoxy, amino, $C_{1-6}$alkylamino, and di-$C_{1-6}$alkylamino 15. The compound of paragraph 1, wherein X is selected from the group consisting of $(CH_2)_s$—NH—$(CH_2)_t$— or —$(CH_2)_s$—O—$(CH_2)_t$—, wherein s and t are each, independently an integer from 1 to 3.

16. The compound of paragraph 1, wherein X is selected from the group consisting of —$CH_2$—NH—$CH_2$— and —$CH_2$—O—$CH_2$—.

17. The compound of paragraph 1, wherein X is a branched $C_{1-10}$ alkyl.

18. The compound of paragraph 1, wherein X is selected from the group consisting of —$CH(CH_3)CH_2$—, —$CH(CH_3)CH(CH_3)$—, —$CH_2C(CH_3)(CH_3)CH_2$—, —$C(CH_3)(CH_3)$—, and —$CH_2C(CH_3)(CH_3)$—.

19. The compound of paragraph 1, wherein the compound is of Formula Ia:

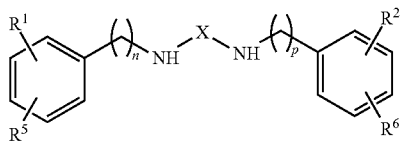

wherein:
X is $C_{1-10}$ alkyl, $(CH_2)_s$—NH—$(CH_2)_t$, $(CH_2)_s$—O—$(CH_2)_t$, or $(CH_2)_s$—C($NH_2$)—$(CH_2)_v$—NH—$(CH_2)_t$, wherein s, t and v are each, independently, an integer from 1 to 5;

$R^1$ and $R^2$ are each, independently, amine, $C_{1-10}$ alkyl, $C_{1-10}$ alkenyl, $C_{1-10}$ alkynyl, $C_{3-7}$ cycloalkyl, $C_{3-7}$ cycloalkyl-$C_{1-6}$alkyl, $C_{3-7}$ heterocycloalkyl, or $C_{3-7}$ heterocycloalkyl-$C_{1-6}$ alkyl; and n and p are each, independently, integers from 1 to 10; and $R^5$ and $R^6$ are each, independently, selected from the group consisting of halogen, $C_{1-6}$ alkyl, $C_{1-6}$ haloalkyl, hydroxyl, $C_{1-6}$ alkoxy, $C_{1-6}$haloalkoxy, amino, $C_{1-6}$alkylamino, and di-$C_{1-6}$alkylamino 20. A pharmaceutical composition comprising:
a compound of general Formula I:

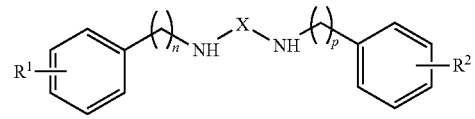

or salt, ester, solvate, hydrate, or prodrug thereof;
wherein:
X is $C_{1-10}$ alkyl, $(CH_2)_s$—NH—$(CH_2)_t$, $(CH_2)_s$—O—$(CH_2)_t$, or $(CH_2)_s$—C($NH_2$)—$(CH_2)_v$—NH—$(CH_2)_t$, where s, t and v are each, independently, an integer from 1 to 5;

$R^1$ and $R^2$ are each, independently, amine, $C_{1-10}$ alkyl, $C_{1-10}$ alkenyl, $C_{1-10}$ alkynyl, $C_{3-7}$ cycloalkyl, $C_{3-7}$ cycloalkyl-$C_{1-6}$alkyl, $C_{3-7}$ heterocycloalkyl, or $C_{3-7}$ heterocycloalkyl-$C_{1-6}$ alkyl; and n and p are each, independently, integers from 1 to 10; and a pharmaceutically acceptable carrier, excipient, or diluent.

21. The pharmaceutical composition of paragraph 20, wherein the carrier is selected from the group consisting of carrier water, ethanol, polyol, glycerol, propylene glycol, liquid polyethylene glycol, vegetable oils, nut oils, and mixtures thereof.

22. The pharmaceutical composition of paragraph 20, further comprising at least one flavoring agent, binding agent, lubricant, disintegrant, surface modifying agent, surfactant, suspending agent, stabilizing agent, fillers, glidant, compression aid, disintegrating agent, encapsulating material, or combinations thereof.

23. The pharmaceutical composition of paragraph 20, further comprising at least one anti-inflammatory agents, antimicrobial agents, matrix metalloprotease inhibitors, lipoxygenase inhibitors, cytokine antagonists, immunosuppressants, anti-cancer agents, anti-viral agents, cytokines, growth factors, immunomodulators, prostaglandins, anti-vascular hyperproliferation compounds, and combinations thereof.

24. The pharmaceutical composition of paragraph 20, wherein the compound of Formula I or salt, ester, solvate, hydrate, or prodrug thereof comprises about 15 wt. % to about 95 wt. % of a total weight of the pharmaceutical composition.

25. The pharmaceutical composition of paragraph 20, wherein the pharmaceutical composition is in unit dose form.

26. The pharmaceutical composition of paragraph 25, wherein each unit dose comprises about 0.5 mg to about 500 mg of the compound of Formula I or salt, ester, solvate, hydrate, or prodrug thereof.

27. A method for treating a disease or condition comprising:
administering to a patient in need of treatment a pharmaceutical composition comprising a compound of general Formula I:

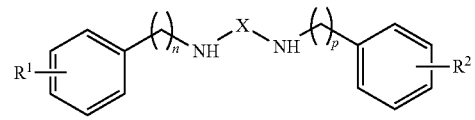

or salt, ester, solvate, hydrate, or prodrug thereof; wherein:

X is $C_{1-10}$ alkyl, $(CH_2)_s$—NH—$(CH_2)_t$, $(CH_2)_s$—O—$(CH_2)_t$, or $(CH_2)_s$—$C(NH_2)$—$(CH_2)_v$—NH—$(CH_2)_t$, where s, t and v are each, independently, an integer from 1 to 5;

$R^1$ and $R^2$ are each, independently, amine, $C_{1-10}$ alkyl, $C_{1-10}$ alkenyl, $C_{1-10}$ alkynyl, $C_{3-7}$ cycloalkyl, $C_{3-7}$ cycloalkyl-$C_{1-6}$alkyl, $C_{3-7}$ heterocycloalkyl, $C_{3-7}$ heterocycloalkyl-$C_{1-6}$ alkyl; and n and p are each, independently, integers from 1 to 10; and a pharmaceutically acceptable carrier, excipient, or diluent.

28. The method of paragraph 27, wherein the compound of Formula I or salt, ester, solvate, hydrate, or prodrug thereof is administered in an effective amount.

29. The method of paragraph 28, wherein an effective amount comprises from about 0.5 mg to about 500 mg of the Formula I or salt, ester, solvate, hydrate, or prodrug thereof.

30. The method of paragraph 28, wherein an effective amount comprises about 0.5 mg/kg to about 500 mg/kg of compound per kg of patient body weight.

31. The method of paragraph 27, wherein administering comprises oral administration, administration via implants, parenteral injection, intravenous injection, intraperitoneal injection, subcutaneous injection, bolus injection, infusion, rectal administration, vaginal administration, transdermal administration, inhalation, and combinations thereof.

32. The method of paragraph 27, further comprising administrating at least one anti-inflammatory agents, antimicrobial agents, matrix metalloprotease inhibitors, lipoxygenase inhibitors, cytokine antagonists, immunosuppressants, anti-cancer agents, anti-viral agents, cytokines, growth factors, immunomodulators, prostaglandins, anti-vascular hyperproliferation compounds, and combinations thereof.

33. The method of paragraph 27, wherein the disease or condition is an inflammatory disorder.

34. The method of paragraph 27, wherein the disease or condition is a respiratory injury or disease.

35. A compound of Formula II, or a salt, ester, solvate, hydrate or prodrug thereof:

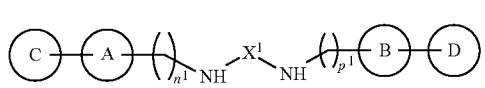

II where:

$X^1$ is a branched or unbranched $C_{1-10}$ alkyl, $(CH_2)_s$—NH—$(CH_2)_t$, $(CH_2)_s$—O—$(CH_2)_t$, or $(CH_2)_s$—$C(NH_2)$—$(CH_2)_v$—NH—$(CH_2)_t$, where s, t and v are each, independently an integer from 1 to 5;

A and B are each, independently, $C_{6-10}$aryl, $C_{6-10}$aryl-$C_{1-6}$alkyl, $C_{3-9}$ heteroaryl, or $C_{3-9}$heteroaryl-$C_{1-6}$alkyl, each optionally substituted with 1, 2 or 3 independently selected $R^g$ groups;

C and D are each, independently, $C_{3-7}$ cycloalkyl, $C_{3-7}$ cycloalkyl-$C_{1-6}$alkyl, $C_{3-7}$ heterocycloalkyl, $C_{3-7}$ heterocycloalkyl-$C_{1-6}$ alkyl, $C_{6-0}$aryl, $C_{6-10}$aryl-$C_{1-6}$alkyl, $C_{3-9}$ heteroaryl, or $C_{3-9}$heteroaryl-$C_{1-6}$alkyl, each optionally substituted with 1, 2 or 3 independently selected $R^g$ groups;

each $R^g$ is, independently, halogen, $C_{1-6}$ alkyl, $C_{1-6}$haloalkyl, hydroxyl, $C_{1-6}$ alkoxy, $C_{1-6}$haloalkoxy, amino, $C_{1-6}$alkylamino, or di-$C_{1-6}$alkylamino; and $n^1$ and $p^1$ are each, independently, integers from 1 to 10.

36. A compound of Formula III, or a salt, ester, solvate, hydrate or prodrug thereof:

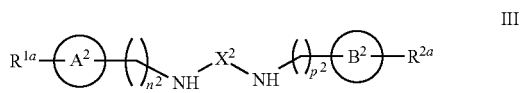

III where:

$X^2$ is a branched or unbranched $C_{1-10}$ alkyl, $(CH_2)_s$—NH—$(CH_2)_t$, $(CH_2)_s$—O—$(CH_2)_t$, or $(CH_2)_s$—$C(NH_2)$—$(CH_2)_v$—NH—$(CH_2)_t$, where s, t and v are each, independently an integer from 1 to 5;

$A^2$ and $B^2$ are each, independently, $C_{6-10}$aryl, $C_{6-10}$aryl-$C_{1-6}$alkyl, $C_{3-9}$ heteroaryl, or $C_{3-9}$heteroaryl-$C_{1-6}$alkyl, each optionally substituted with 1, 2 or 3 independently selected $R^g$ groups;

$R^{1a}$ and $R^{2a}$ are each, independently, $C_{1-10}$ alkyl, $C_{1-10}$ alkenyl, $C_{1-10}$ alkynyl, $C_{3-7}$ cycloalkyl, $C_{3-7}$ cycloalkyl-$C_{1-6}$alkyl, $C_{3-7}$ heterocycloalkyl, or $C_{3-7}$ heterocycloalkyl-$C_{1-6}$ alkyl, each of which can be optionally substituted with 1, 2 or 3 independently selected $R^g$ groups;

each $R^g$ is, independently, halogen, $C_{1-6}$ alkyl, $C_{1-6}$ haloalkyl, hydroxyl, $C_{1-6}$ alkoxy, $C_{1-6}$ haloalkoxy, amino, $C_{1-6}$alkylamino, or di-$C_{1-6}$alkylamino; and $n^2$ and $p^2$ are each, independently, integers from 1 to 10.

EXAMPLES

Although the present invention has been described in considerable detail with reference to certain preferred embodiments thereof, other versions are possible. Therefore, the spirit and scope of the appended claims should not be limited to the description and the preferred versions contained within this specification. Various aspects of the present invention will be illustrated with reference to the following non-limiting examples.

Example 1

Compound Synthesis

Compound 204: (S)-(−)-1,2-Diaminopropane DiHCl (0.005 mol, 0.74 g) was added to anhydrous ethanol (30 ml) containing 0.01 mol of Triethylamine 4-(pyrimidin-2-yl) benzaldehyde (0.01 mol, 1.85 g) was later added to the solution. The resulting solution was refluxed and stirred for 1 h. Solvent were then removed through rotary evaporation. The resulting Schiff base was then added to 30 ml of absolute methanol. A 10% solution of sodium borohydride (0.01 mol) was dissolved in absolute methanol and added to the Schiff base. When the dropwise addition of sodium borohydride was complete, the reaction solution was refluxed for an additional 15 min Solvent was then removed through rotary evaporation and 20 ml cold water was added to liberate the secondary amine The precipitation of Compound 204 were collected, washed with water and dried.

Compound 205: (R)-(+)-1,2-Diaminopropane DiHCl (0.005 mol, 0.74 g) was added to anhydrous ethanol (30 ml) containing 0.01 mol of Triethylamine 4-(pyrimidin-2-yl) benzaldehyde (0.01 mol, 1.85 g) was later added to the solution. The resulting solution was refluxed and stirred for 1 h. Solvent were then removed through rotary evaporation.

The resulting Schiff base was then added to 30 ml of absolute methanol. A 10% solution of sodium borohydride (0.01 mol) was dissolved in absolute methanol and added to the Schiff base. When the dropwise addition of sodium borohydride was complete, the reaction solution was refluxed for an additional 15 min Solvent was then removed through rotary evaporation and 20 ml cold water was added to liberate the secondary amine The precipitation of Compound 205 were collected, washed with water and dried.

Compound 206: 2-Methyl-1,2-propanediamine (0.005 mol, 0.44 g) was added to anhydrous ethanol (30 ml). 4-(pyrimidin-2-yl)benzaldehyde (0.01 mol, 1.85 g) was later added to the solution. The resulting solution was refluxed and stirred for 1h. Solvent were then removed through rotary evaporation. The resulting Schiff base was then added to 30 ml of absolute methanol. A 10% solution of sodium borohydride (0.01 mol) was dissolved in absolute methanol and added to the Schiff base. When the dropwise addition of sodium borohydride was complete, the reaction solution was refluxed for an additional 15 min. Solvent was then removed through rotary evaporation and 20 ml cold water was added to liberate the secondary amine The precipitation of Compound 206 were collected, washed with water and dried.

Compound 207: 2,3-Diamino-2,3-dimethylbutane Dihydrochloride (0.005 mol, 0.95 g) was added to anhydrous ethanol (30 ml) containing 0.01 mol of Triethylamine 4-(pyrimidin-2-yl)benzaldehyde (0.01 mol, 1.85 g) was later added to the solution. The resulting solution was refluxed and stirred for 1h. Solvent were then removed through rotary evaporation. The resulting Schiff base was then added to 30 ml of absolute methanol. A 10% solution of sodium borohydride (0.01 mol) was dissolved in absolute methanol and added to the Schiff base. When the dropwise addition of sodium borohydride was complete, the reaction solution was refluxed for an additional 15 min. Solvent was then removed through rotary evaporation and 20 ml cold water was added to liberate the secondary amine The precipitation of Compound 207 were collected, washed with water and dried.

Compound 210: 1,4-Diaminobutane (0.005 mol, 0.44 g) was added to anhydrous ethanol (30 ml). 2-pyrrolidin-1-ylpyrimidine-5-carbaldehyde (0.01 mol, 1.77 g) was later added to the solution. The resulting solution was refluxed and stirred for 1 h. Solvent were then removed through rotary evaporation. The resulting Schiff base was then added to 30 ml of absolute methanol. A 10% solution of sodium borohydride (0.01 mol) was dissolved in absolute methanol and added to the Schiff base. When the dropwise addition of sodium borohydride was complete, the reaction solution was refluxed for an additional 15 min. Solvent was then removed through rotary evaporation and 20 ml cold water was added to liberate the secondary amine The precipitation of Compound 201 were collected, washed with water and dried.

Example 2

Peripheral blood mononuclear cells (PBMC) (0.2 ml at 0.3×106/ml) were treated with lipopolysaccharide (LPS) (50 ng/ml) for 16 hours concurrently with each compound tested at different concentrations. TNFα cytokine release was monitored by ELISA. These concentrations were used to calculate the IC50.

U937 monocytes (0.2 ml at 0.3×106/ml) were treated with each compound at different concentrations for 16 hours. The cells were then stained with Trypan blue to identify dead cells, and to calculate the LC50. Combined values were used to generate therapeutic indexes (TI)=LC50/IC50.

The results are presented in Table 3:

TABLE 3

| Compound | IC50 | LC50 |
|---|---|---|
| Compound 201 | +++ | + |
| Compound 202 | +++ | + |
| Compound 203 | ++ | + |
| Compound 204 | +++ | + |
| Compound 205 | +++ | + |
| Compound 206 | +++ | + |
| Compound 207 | ++ | + |
| Compound 208 | ++ | ++ |
| Compound 209 | ++ | ++ |
| Compound 210 | +++ | +++ |

For IC50,
"+": >20 ug/ml,
"++": 2-20 ug/ml,
"+++": <2 ug/ml
For LC50,
"+": >100 ug/ml,
"++": 10-100 ug/ml,
"+++": 1-10 ug/ml,
"++++": <1 ug/ml

Example 3

Synthesis of $N^1,N^2$-bis(3-fluoro-4-(pyrimidin-2-yl)benzyl)ethane-1,2-diamine (BC-1421)

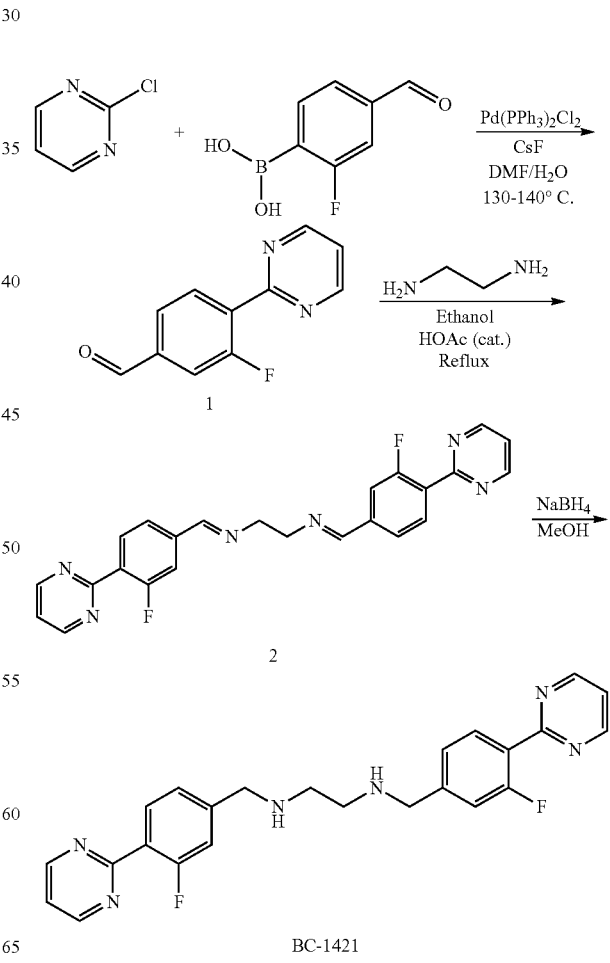

BC-1421

Step 1. Synthesis of
3-fluoro-4-(pyrimidin-2-yl)benzaldehyde
(Intermediate 1)

A mixture of 2-chloropyrimidine (572.5 mg, 5.0 mmol), (2-fluoro-4-formylphenyl)boronic acid (839.5 mg, 5.0 mmol), CsF (1.52 g, 10 mmol) and Pd(PPh$_3$)$_2$Cl$_2$ (350 mg, 0.5 mmol) in DME/H2O (1:1, 20 mL) was heated in a sealed tube at 130-140° C. (oil bath) for 1 h. It underwent changes from a suspension to a near solution and back to a suspension. After cooling to room temperature, the reaction was diluted with ethyl acetate (50 mL) and vacuum filtered. The solid was washed with ethyl acetate (5 mL). The filtrate was extracted with ethyl acetate (100 mL). The organic layer was washed with water (30 mL), brine (30 mL) and dried over anhydrous sodium sulfate. Removal of solvent in vacuo afforded the crude as a light brown solid. It was purified by flash column (silica gel, hexane/ethyl acetate, 3:1, v/v) to obtain the intermediate 1 as a white solid (0.7 g, 69% yield).

Step 2. Synthesis of (N$^1$E,N$^2$E)-N$^1$,N$^2$-bis(3-fluoro-4-(pyrimidin-2-yl)benzylidene)ethane-1,2-diamine
(Intermediate 2)

A mixture of the intermediate 1 (677 mg, 3.35 mmol) and ethane-1,2-diamine (100.7 mg, 1.68 mmol) was heated at reflux in absolute ethanol (15 ml) containing 1 drop of glacial acetic acid. After completion of reaction, the mixture was cooled to room temperature. The solid was collected by vacuum filtration and dried to obtain the intermediate 2 as a white solid (0.64 g, 89% yield).

Step 3. Synthesis of N$^1$,N$^2$-bis(3-fluoro-4-(pyrimidin-2-yl)benzyl)ethane-1,2-diamine (BC-1421)

To a suspension of the intermediate 2 (0.64 g, 1.5 mmol) in methanol (10 mL) was added solid NaBH$_4$ (113.5 mg, 3.0 mmol). The reaction was heated at reflux. After ca 10 min, it turned into a clear solution. Additional portion of solid NaBH$_4$ (50 mg) was added and the reaction was heated at reflux until completion. After cooling to room temperature, it was concentrated in vacuo. The residue was mixed with water (25 mL) and extracted with ethyl acetate (50 mL×2). The organic layer was washed with water (25 mL×2) and dried over anhydrous sodium sulfate. Removal of solvent in vacuo afforded the crude as a light yellow oil which was purified by flash column (silica gel, toluene/2-propanol/NH4OH=79:20:1, v/v/v) to obtain BC-1421 as a clear oil. It was dissolved in dichloromethane (1 mL) which was evaporated by gently blowing nitrogen to obtain a solid. After drying under high vacuum, pure BC-1421 was obtained (219.5 mg, 34% yield). $^1$H NMR (400 MHz, DMSO-d$_6$) δ 8.91 (d, 4H), 7.94 (t, 2H), 7.46 (t, 2H), 7.30 (m, 4H), 3.75 (s, 4H), 2.61 (s, 4H); LCMS m/z 433.1 [M+H]$^+$, 217.1 [M+2H]$^{2+}$/2.

Synthesis of (S)-N$^2$-(2-fluoro-4-(5-fluoropyrimidin-2-yl)benzyl)-N$^1$-(4-(5-methyl-1,3,4-oxadiazol-2-yl)benzyl)propane-1,2-diamine (BC-1568)

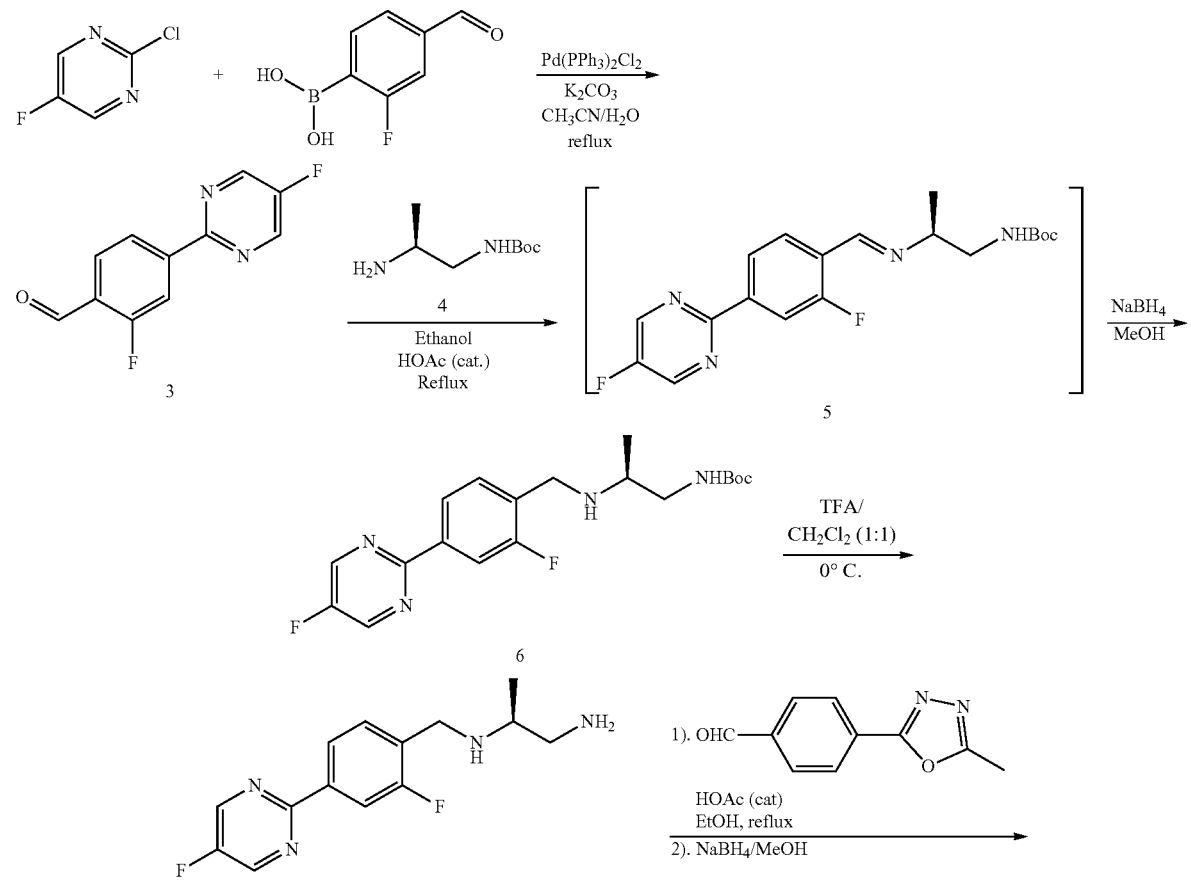

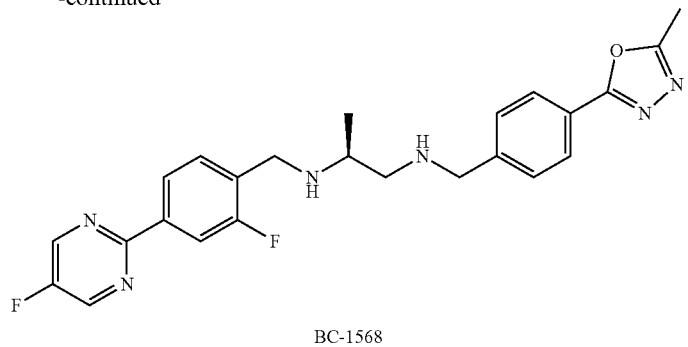

BC-1568

Step 1. Synthesis of 2-fluoro-4-(5-fluoropyrimidin-2-yl)benzaldehyde (Intermediate 3)

A mixture of 2-chloro-5-fluoropyrimidine (789 mg, 5.95 mmol), (2-fluoro-4-formylphenyl)boronic acid (1.0 g, 5.95 mmol), potassium carbonate (1.65 g, 11.9 mmol), acetonitrile (30 mL) and water (30 mL) in a 250 mL 3-necked round-bottomed flask was degassed by bubbling nitrogen for 15 min followed by addition of Pd(Ph$_3$)$_2$Cl$_2$ (209 mg, 0.298 mmol). The reaction was heated at reflux for 5 h. After cooling to room temperature, it was concentrated in vacuo to remove acetonitrile. Brown solid formed in the aqueous solution was collected by vacuum filtration, washed with water and dried. It was purified by flash column (silica gel, hexane/ethyl acetate 3:1, v/v) to obtain the intermediate 3 as an off-white solid (1.0 g, 77% yield).

Step 2. Synthesis of (S)-tert-butyl (2-((2-fluoro-4-(5-fluoropyrimidin-2-yl)benzyl)amino)propyl)carbamate (Intermediate 6)

A mixture of the intermediate 3 (0.40 g, 1.82 mmol) and (S)-tert-butyl (2-aminopropyl)carbamate (intermediate 4, 0.32 g, 1.82 mmol, prepared according to literature: Pittelkow, M. et al *Synthesis* 2002, 2195-2202) in absolute ethanol (5 mL) containing 1 drop of glacial acetic acid was heated at reflux for two hours. After cooling to room temperature, solvent was removed in vacuo. The residue was dissolved in methanol (10 mL), cooled in an ice-water bath, treated with solid sodium borohydride (173 mg, 4.57 mmol) for 20 min. It was quenched by addition of water (20 mL). The mixture was extracted with ethyl acetate (25 mL×3). The organic layer was dried over anhydrous sodium sulfate. Removal of solvent in vacuo afforded the crude which was purified by flash column (silica gel, dichloromethane/methanol/NH4OH=97:3;0.1) to obtain intermediate 6 as an oil (0.5 g).

Step 3. Synthesis (S)-N$^2$-(2-fluoro-4-(5-fluoropyrimidin-2-yl)benzyl)propane-1,2-diamine (Intermediate 7)

The intermediate 6 (0.5 g) was dissolved in dichloromethane (5 mL) and treated with TFA (5 mL) at room temperature for 1h. It was concentrated in vacuo. The residue was dissolved in 2 N HCl (10 mL), washed with dichloromethane (20 mL×2). The aqueous phase was basified to pH 14 with 10 N NaOH and extracted with dichloromethane (25 mL×5). The organic layer was dried over anhydrous sodium sulfate. Removal of solvent in vacuo afforded the intermediate 7 as an oil (0.4 g).

Step 4. Synthesis of (S)-N$^2$-(2-fluoro-4-(5-fluoropyrimidin-2-yl)benzyl)-N$^1$-(4-(5-methyl-1,3,4-oxadiazol-2-yl)benzyl)propane-1,2-diamine (BC-1568)

A mixture of the intermediate 7 (0.4 g, 1.44 mmol) and 4-(5-methyl-1,3,4-oxadiazol-2-yl)benzaldehyde (250 mg, 1.33 mmol) in absolute ethanol (10 mL) containing 2 drops of glacial acetic acid was heated at reflux overnight. After cooling to room temperature, it was concentrated in vacuo. The residue was dissolved in methanol (10 mL), cooled in an ice-water bath, and treated with solid sodium borohydride (74 mg, 1.96 mmol) for 10 min. It was quenched with water (5 mL), extracted with dichloromethane (50 mL×2). The organic layer was dried over anhydrous sodium sulfate. Removal of solvent in vacuo afforded the crude which was purified by flash column (silica gel, dichloromethane/MeOH/NH4OH=97:3:0.1) to obtain a light yellow oil (ca 300 mg). It was dissolved I 1N HCl (10 mL) and lyophilized to obtain an off-white powder which contained a single polar impurity (ca 15% by HPLC). The material was dissolved in water (70 mL), basified with 10 N NaOH and extracted with dichloromethane (50 mL×3). The organic layer was dried over anhydrous sodium sulfate. Removal of solvent in vacuo afforded an oil which was further purified by flash column (silica gel, dichloromethane/MeOH/NH4OH=97:3:0.1) to obtain an oil which slowly solidified upon standing to give 167.4 mg of BC-1568. $^1$H NMR (400 MHz, DMSO-d$_6$) δ 9.00 (s, 2H), 7.90 (m, 3H), 7.50 (m, 2H), 7.30 (m, 2H), 3.60-3.80 (m, 4H), 2.65 (m, 1H), 2.55 (s, 3H), 2.40 (m, 2H), 0.98 (d, 3H); LCMS m/z 451.2 [M+H]+.

Synthesis of (S)-N$^2$-(4-(5-fluoropyrimidin-2-yl)benzyl)-N$^1$-(4-(oxazol-5-yl)benzyl)propane-1,2-diamine (BC-1563), (S)-N$^1$-((5-(1,3,4-oxadiazol-2-yl)pyridin-2-yl)methyl)-N$^2$-(4-(5-fluoropyrimidin-2-yl)benzyl)propane-1,2-diamine (BC-1566) and (S)-N$^2$-(4-(5-fluoropyrimidin-2-yl)benzyl)-N$^1$-(4-(4-methyloxazol-5-yl)benzyl)propane-1,2-diamine (BC-1567)

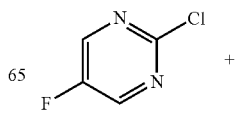

+

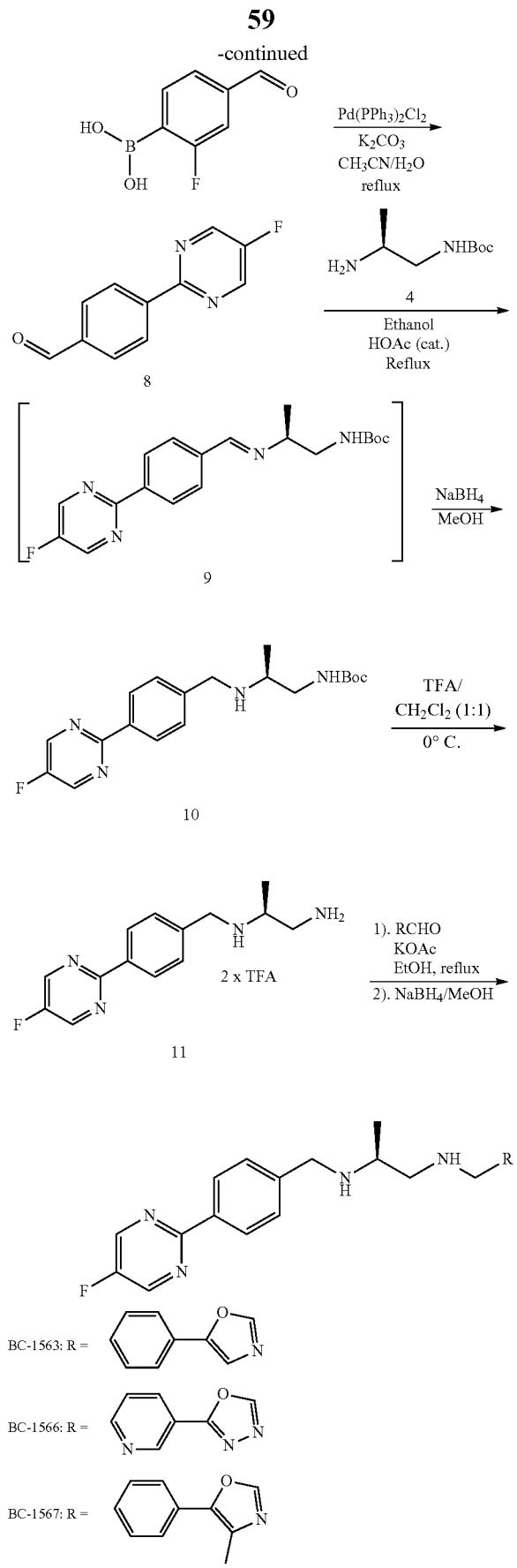

Synthesis of (S)-N²-(4-(5-fluoropyrimidin-2-yl)benzyl)propane-1,2-diamine di-TFA Salt (the Common Intermediate 11)

Step 1. Synthesis of the aldehyde Intermediate 8

A mixture of 2-chloro-5-fluoropyrimidine (2.65 g, 20 mmol), (4-formylphenyl)boronic acid (3.0 g, 20 mmol), potassium carbonate (5.53 g, 40 mmol), acetonitrile (100 mL) and water (100 mL) in a 250 mL 3-necked round-bottomed flask was degassed by bubbling nitrogen for 15 min followed by addition of Pd(Ph$_3$)$_2$Cl$_2$ (702 mg, 1.0 mmol). The reaction was heated at reflux for 5 h. After cooling to room temperature, it was concentrated in vacuo to remove acetonitrile. Brown solid formed in the aqueous solution was collected by vacuum filtration, washed with water and dried. It was purified by flash column (silica gel, hexane/ethyl acetate 3:1, v/v) to obtain the intermediate 8 as an off-white solid (3.76 g, 93% yield).

Step 2. Synthesis of (S)-tert-butyl (2-((4-(5-fluoropyrimidin-2-yl)benzyl)amino)propyl)carbamate (Intermediate 10)

A mixture of the intermediate 8 (2.40 g, 11.87 mmol) and (S)-tert-butyl (2-aminopropyl)carbamate (intermediate 4, 2.07 g, 11.87 mmol) in absolute ethanol (50 mL) containing 5 drops of glacial acetic acid was heated at reflux for two hours. After cooling to room temperature, solvent was removed in vacuo. The residue was dissolved in methanol (100 mL), cooled in an ice-water bath, treated with solid sodium borohydride (449 mg, 11.87 mmol) for 10 min. It was quenched by addition of water (50 mL). The mixture was extracted with ethyl acetate (80 mL×3). The organic layer was washed with brine (50 mL) and dried over anhydrous sodium sulfate. Removal of solvent in vacuo afforded the crude as a brown oil which was purified by flash column (silica gel, dichloromethane/methanol/NH4OH=97:3;0.1) to obtain the intermediate 10 as a light brown oil (2.1 g, 49% yield).

Step 3. Synthesis of the Common Intermediate 11

The intermediate 10 (2.1 g) was dissolved in dichloromethane (25 mL) at 0° C. followed by addition of TFA (10 mL). The reaction was stirred at room temperature for 40 min. It was concentrated in vacuo to dryness. The residue was further dried by blowing air until a viscous oil was obtained at which point the TFA odor was no longer detected. The residue was triturated in water (20 mL) to obtain a tan solid which was filtered, washed with water and dried to obtain the first crop of product (1.08 g). The filtrate was lyophilized to obtain the second crop of product as a white solid (1.7 g).

Synthesis of (S)-N²-(4-(5-fluoropyrimidin-2-yl)benzyl)-N¹-(4-(oxazol-5-yl)benzyl)propane-1,2-diamine (BC-1563)

A mixture of the intermediate 11 (342 mg, 0.7 mmol) and potassium acetate (151 mg, 1.54 mmol) in absolute ethanol (5 mL) was stirred at 80° C. for 5 min followed by addition of 4-(oxazol-5-yl)benzaldehyde (131 mg, 0.756 mmol). The reaction was heated at reflux for 1 h. It was concentrated in vacuo to obtain a light brown solid which was dissolved in methanol (10 mL). The solution was cooled in an ice-water bath for 5 min followed by addition of solid sodium borohydride (26.5 mg, 0.7 mmol). It was stirred at 0° C. for 10 min and quenched by addition of water (10 mL). Methanol was removed in vacuo. The residue was basified with 10 N NaOH and extracted with dichloromethane (50 mL×2). The organic layer was dried over anhydrous sodium sulfate. Removal of solvent in vacuo afforded the crude product as a brown oil which was purified by flash column (silica gel, dichloromethane/methanol/NH4OH=97:3:0.1) to obtain BC-1563 as a white solid (96.4 mg, 33% yield). $^1$H NMR (400 MHz, DMSO-$d_6$) δ 8.94 (s, 2H), 8.40 (s, 1H), 8.25 (d, 2H), 7.63 (d, 2H), 7.62 (s, 1H), 7.45 (d, 2H), 7.38 (d, 2H), 3.60-3.80 (m, 4H), 2.70 (m, 1H), 2.40 (m, 2H), 0.98 (d, 3H); LCMS m/z 418.1 [M+H]+.

Synthesis of (S)-N¹-((5-(1,3,4-oxadiazol-2-yl)pyridin-2-yl)methyl)-N²-(4-(5-fluoropyrimidin-2-yl)benzyl)propane-1,2-diamine (BC-1566)

Compound BC-1566 was prepared in the same fashion as described for BC-1563 by reacting the intermediate 11 with 5-(1,3,4-oxadiazol-2-yl)picolinaldehyde in 31% yield. $^1$H NMR (400 MHz, DMSO-d6) δ 9.39 (s, 1H), 9.06 (s, 1H), 8.94 (s, 2H), 8.32 (d, 1H), 8.23 (d, 2H), 7.64 (d, 1H), 7.46 (d, 2H), 3.60-3.85 (m, 4H), 2.70 (m, 1H), 2.45 (m, 2H), 0.99 (d, 3H); LCMS nik 420.1 [M+H]+.

Synthesis of (S)-N²-(4-(5-fluoropyrimidin-2-yl)benzyl)-M-(4-(4-methyloxazol-5-yl)benzyl)propane-1,2-diamine (BC-1567)

Compound BC-1567 was prepared in the same fashion as described for BC-1563 by reacting the intermediate 11 with 4-(4-methyloxazol-5-yl)benzaldehyde in 70% yield. $^1$H NMR (400 MHz, DMSO-$d_6$) δ 8.94 (s, 2H), 8.29 (s, 1H), 8.24 (d, 2H), 7.52 (d, 2H), 7.45 (d, 2H), 7.39 (d, 2H), 3.60-3.85 (m, 4H), 2.70 (m, 1H), 2.40 (m, 2H), 2.32 (s, 3H), 0.98 (d, 3H); LCMS m/z 432.1 [M+H]+.

Synthesis of (R)-N¹-(4-(1,3,4-oxadiazol-2-yl)benzyl)-3,3,3-trifluoro-N²-(4-(5-fluoropyrimidin-2-yl)benzyl)propane-1,2-diamine (BC-1564)

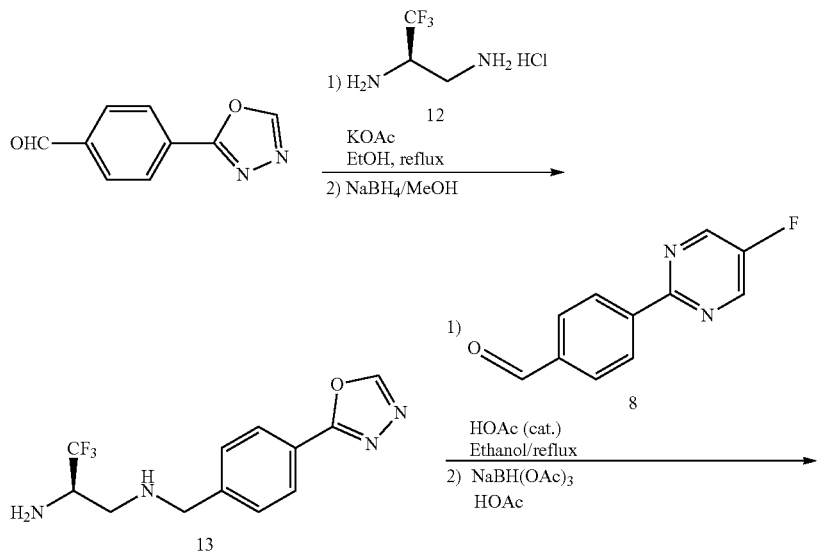

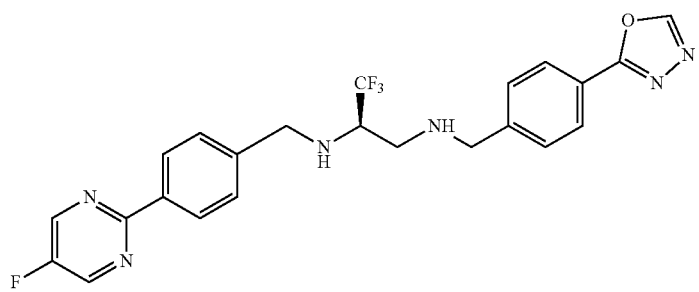

BC-1564

Step 1. Synthesis of (R)-N¹-(4-(1,3,4-oxadiazol-2-yl)benzyl)-3,3,3-trifluoropropane-1,2-diamine (Intermediate 13)

A mixture of (R)-3,3,3-trifluoropropane-1,2-diamine hydrochloride 12 (271 mg, 1.65 mmol) and potassium acetate (178 mg, 1.82 mmol) in absolute ethanol (5 mL) was stirred at 80° C. for 5 min followed by addition of 4-(1,3,4-oxadiazol-2-yl)benzaldehyde (287.4 mg, 1.65 mmol). The reaction was heated at reflux for 5 h to obtain a lightly colored suspension. It was concentrated in vacuo. The residue was suspended in methanol (20 mL), cooled in ice-water bath, and treated with solid sodium borohydride in portions (62 mg×4). It was quenched with water (20 mL), extracted with dichloromethane (50 mL×3). The organic layer was dried over anhydrous sodium sulfate. Removal of solvent in vacuo afforded a light yellow oil which was purified by flash column (silica gel, ethyl acetate/hexanes 1:1 to dichloromethane/methanol/NH4OH=97:3:0.1) to obtain the intermediate 13 as a clear oil. It was solidified into a white solid upon standing (170 mg, 36% yield).

Step 2. Synthesis of (R)-N¹-(4-(1,3,4-oxadiazol-2-yl)benzyl)-3,3,3-trifluoro-N²-(4-(5-fluoropyrimidin-2-yl)benzyl)propane-1,2-diamine (BC-1564)

A mixture of the intermediate 8 (113 mg, 0.56 mmol) and the intermediate 13 (160 mg, 0.56 mmol) in absolute ethanol (5 mL) containing 1 drop of glacial acetic acid was heated at reflux for 4 h. It was concentrated in vacuo. The residue was dissolved in acetic acid (5 mL), treated with solid NaBH(OAc)₃ in three portions (170 mg, 33 mg, 34 mg). After completion of the reaction, it was diluted with water (10 mL), neutralized with 10 N NaOH to pH 4, and extracted with dichloromethane (50 mL×3). The organic layer was dried over anhydrous sodium sulfate. Removal of solvent in vacuo afforded the crude product as a light brown oil. It was purified by flash column (silica gel, hexane/ethyl acetate=3:2) to obtain BC-1564 as a solid (57.7 mg, 22% yield). ¹H NMR (400 MHz, DMSO-d₆) δ 9.31 (s, 1H), 8.94 (s, 2H), 8.25 (d, 2H), 7.91 (d, 2H), 7.47 (d, 4H), 3.90 (m, 2H), 3.69 (s, 2H), 2.60-2.80 (m, 3H); LCMS m/z 473.1 [M+H]⁺.

In view of the many possible embodiments to which the principles of the disclosed compounds, compositions, and methods may be applied, it should be recognized that the illustrated embodiments are only preferred examples of the invention and should not be taken as limiting the scope of the invention.

What is claimed is:

1. A compound, or a salt, ester, solvate, hydrate or prodrug thereof, having a structure of:

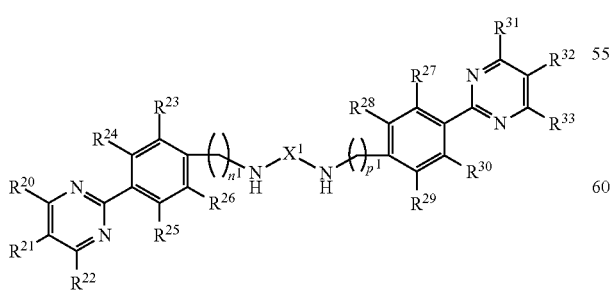

wherein $X^1$ is a branched or unbranched $C_{1-10}$ alkyl, $(CH_2)_s$—NH—$(CH_2)_t$, $(CH_2)_s$, —O—$(CH_2)_t$, or $(CH_2)_s$—C(NH_2)—$(CH_2)_v$—NH—$(CH_2)_t$, wherein s, t and v are each, independently an integer from 1 to 5;

$n^1$ and $p^1$ are each, independently, integers from 1 to 10;

$R^{20}$—$R^{33}$ are each independently hydrogen, halogen, or $C_{1-6}$ haloalkyl, provided at least one of $R^{20}$—$R^{33}$ is halogen.

2. The compound of claim 1, wherein at least one of $R^{20}$—$R^{33}$ is fluorine.

3. The compound of claim 1, wherein $R^{25}$ and $R^{30}$ are fluorine.

4. The compound of claim 2, wherein $X^1$ is a branched or unbranched $C_{1-10}$ alkyl.

5. The compound of claim 1, wherein $R^{26}$ and $R^{29}$ are fluorine.

6. The compound of claim 1, wherein $R^{21}$ and $R^{22}$ are each fluorine.

7. The compound of claim 1, wherein $X^1$ is a branched $C_{1-10}$ alkyl.

8. The compound of claim 1, wherein $X^1$ is —CH(CH₃)CH₂—.

9. A compound, or a salt, ester, solvate, hydrate or prodrug thereof, having a structure of:

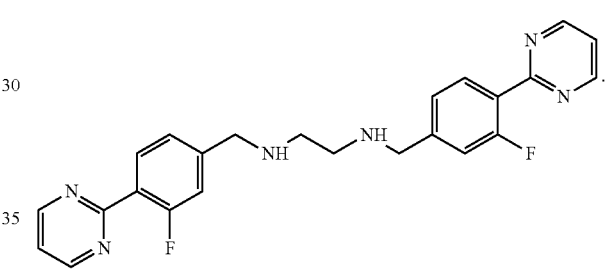

10. A compound of structure:

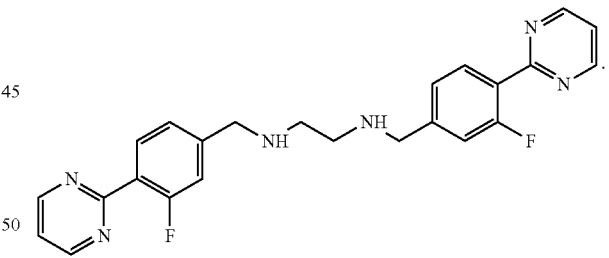

11. A pharmaceutical composition comprising:
a compound of claim 1; and
a pharmaceutically acceptable carrier, excipient, or diluent.

12. A pharmaceutical composition comprising:
a compound of claim 9; and
a pharmaceutically acceptable carrier, excipient, or diluent.

13. A pharmaceutical composition comprising:
a compound of claim 10; and
a pharmaceutically acceptable carrier, excipient, or diluent.

14. A compound of structure:
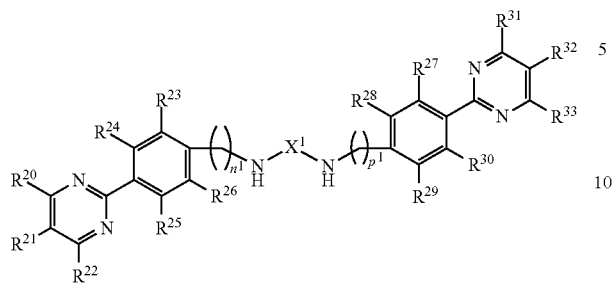
wherein $X^1$ is a branched or unbranched $C_{1-10}$ alkyl, $(CH_2)_s-NH-(CH_2)_t, (CH_2)_s-O-(CH_2)_t$, or $(CH_2)_s-C(NH_2)-(CH_2)_v-NH-(CH_2)_t$, where s, t and v are each, independently an integer from 1 to 5; $n^1$ and $p^1$ are each, independently, integers from 1 to 10; $R^{20}-R^{33}$ are each independently hydrogen, halogen, or $C_{1-6}$ haloalkyl, provided at least one of $R^{20}-R^{33}$ is halogen.
* * * * *

UNITED STATES PATENT AND TRADEMARK OFFICE
CERTIFICATE OF CORRECTION

PATENT NO. : 10,487,076 B2
APPLICATION NO. : 15/533978
DATED : November 26, 2019
INVENTOR(S) : Chen et al.

Page 1 of 1

It is certified that error appears in the above-identified patent and that said Letters Patent is hereby corrected as shown below:

In the Specification

Column 1, Lines 14-18, Acknowledgment of Government Support:
"This invention was made with government support under HL116472, UH2HL123502, HL081784, HL068135, HL096376, HL098174, and HL097376 awarded by the National Institutes of Health. The government has certain rights in the invention"

Should read --This invention was made with government support under HL068135, HL081784, HL096376, HL097376, HL098174, HL116472, and HL123502 awarded by the National Institutes of Health. The government has certain rights in the invention.--

Signed and Sealed this
Eighth Day of July, 2025

Coke Morgan Stewart
*Acting Director of the United States Patent and Trademark Office*